(12) United States Patent
Lu et al.

(10) Patent No.: US 7,485,419 B2
(45) Date of Patent: Feb. 3, 2009

(54) BIOSENSORS BASED ON DIRECTED ASSEMBLY OF PARTICLES

(75) Inventors: Yi Lu, Champaign, IL (US); Juewen Liu, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 306 days.

(21) Appl. No.: 10/756,825

(22) Filed: Jan. 13, 2004

(65) Prior Publication Data

US 2009/0011402 A1 Jan. 8, 2009

(51) Int. Cl.
*C12Q 1/68* (2006.01)
(52) U.S. Cl. .......................................... 435/6
(58) Field of Classification Search ................ None
See application file for complete search history.

(56) References Cited

U.S. PATENT DOCUMENTS

| | | |
|---|---|---|
| 4,703,017 A | 10/1987 | Campbell et al. |
| 4,855,240 A | 8/1989 | Rosenstein et al. |
| 5,459,040 A | 10/1995 | Hammock et al. |
| 5,472,881 A | 12/1995 | Beebe et al. |
| 5,580,967 A | 12/1996 | Joyce |
| 5,593,835 A | 1/1997 | Rando et al. |
| 5,631,148 A | 5/1997 | Urdea |
| 5,663,064 A | 9/1997 | Burke et al. |
| 5,807,718 A | 9/1998 | Joyce et al. |
| 5,807,967 A | 9/1998 | Snow et al. |
| 5,910,408 A | 6/1999 | Szostak et al. |
| 5,989,813 A | 11/1999 | Gerdes |
| 6,040,138 A | 3/2000 | Lockhart et al. |
| 6,110,462 A | 8/2000 | Barbas et al. |
| 6,287,765 B1 | 9/2001 | Cubicciotti |
| 6,316,194 B1 | 11/2001 | Karn et al. |
| 6,361,944 B1 * | 3/2002 | Mirkin et al. ................. 435/6 |
| 6,451,535 B1 | 9/2002 | Jenne et al. |
| 6,485,982 B1 | 11/2002 | Charlton |
| 6,541,617 B1 | 4/2003 | Bamdad et al. |
| 6,630,306 B1 | 10/2003 | Breaker |
| 6,706,474 B1 | 3/2004 | Lu et al. |
| 6,818,455 B2 | 11/2004 | May et al. |

(Continued)

FOREIGN PATENT DOCUMENTS

EP 121970 10/1984

(Continued)

OTHER PUBLICATIONS

Cuenoud and Szostak (1995) Nature vol. 375: pp. 611-614.*

(Continued)

*Primary Examiner*—Teresa E Strzelecka
*Assistant Examiner*—Suchira Pande
(74) *Attorney, Agent, or Firm*—Evan Law Group LLC

(57) ABSTRACT

A sensor system for detecting an effector or cofactor comprises (a) a nucleic acid enzyme; (b) a substrate for the nucleic acid enzyme, comprising a first polynucleotide; (c) a first set of particles comprising a second polynucleotide at least partially complementary to the substrate, where the polynucleotide is attached to the particles at its 3' terminus; and (d) a second set of particles comprising a third polynucleotide at least partially complementary to the substrate, where the polynucleotide is attached to the particles at its 5' terminus.

27 Claims, 9 Drawing Sheets

U.S. PATENT DOCUMENTS

| | | | |
|---|---|---|---|
| 6,849,414 | B2 | 2/2005 | Guan et al. |
| 6,890,719 | B2 * | 5/2005 | Lu et al. ................. 435/6 |
| 7,192,708 | B2 | 3/2007 | Lu et al. |
| 2003/0215810 | A1 | 11/2003 | Lu et al. |
| 2004/0018515 | A1 | 1/2004 | Diener et al. |
| 2004/0126882 | A1 | 7/2004 | Ellington et al. |
| 2004/0175693 | A1 | 9/2004 | Lu et al. |
| 2005/0136500 | A1 | 6/2005 | Yang et al. |
| 2005/0282186 | A1 | 12/2005 | Lu et al. |
| 2006/0019406 | A1 | 1/2006 | Wei et al. |
| 2006/0094026 | A1 | 5/2006 | Lu et al. |
| 2006/0166222 | A1 | 7/2006 | Lu et al. |
| 2007/0037171 | A1 | 2/2007 | Lu et al. |
| 2007/0269821 | A1 | 11/2007 | Mazumdar et al. |

FOREIGN PATENT DOCUMENTS

| | | |
|---|---|---|
| EP | 1219708 | 7/2002 |
| EP | 1 312 674 | 5/2003 |
| GB | 2339280 | 1/2000 |
| WO | WO 96/17086 | 6/1996 |
| WO | WO 97/09342 | 3/1997 |
| WO | WO 98/04740 | 2/1998 |
| WO | WO 98/27104 | 6/1998 |
| WO | WO 98/39484 | 9/1998 |
| WO | WO 98/49346 | 11/1998 |
| WO | WO98/49346 * | 11/1998 |
| WO | WO 99/13338 | 3/1999 |
| WO | WO 99/27351 | 6/1999 |
| WO | WO 99/47704 | 9/1999 |
| WO | WO 00/26226 | 5/2000 |
| WO | WO 00/58505 | 10/2000 |
| WO | WO 01/00876 | 1/2001 |
| WO | WO 01/23548 | 4/2001 |
| WO | WO 01/24696 | 4/2001 |
| WO | WO 01/27612 A2 | 4/2001 |
| WO | WO 01/27612 A3 | 4/2001 |
| WO | WO 01/51665 | 7/2001 |
| WO | WO 01/73123 | 10/2001 |
| WO | WO 02/00006 | 1/2002 |
| WO | WO 02/22882 | 3/2002 |
| WO | WO 02/098364 | 12/2002 |
| WO | WO 03/062422 | 7/2003 |
| WO | WO 03/068963 | 8/2003 |
| WO | WO 03/094838 | 11/2003 |
| WO | WO 03/095648 | 11/2003 |
| WO | 2004/081235 | 9/2004 |
| WO | WO 2004/081235 A1 * | 9/2004 |
| WO | WO 2005/095967 | 10/2005 |
| WO | WO 2005/100602 | 10/2005 |
| WO | WO 2006/048164 | 5/2006 |
| WO | WO 2006/052419 | 5/2006 |
| WO | WO 2006/078660 | 7/2006 |
| WO | WO 2007/106118 | 9/2007 |
| WO | WO 2007/109500 | 9/2007 |

OTHER PUBLICATIONS

Fraunedorf and Jaeschke (2001) Biorganic & Medicinal Chemistry vol. 9: 2521-2524.*

Li and Lu (2000) J. Am. Chem. Soc. 122: 10466-10467.*

Abstract of Joyce, G., "Design and catalytic activity of enzyumic DNA molecules"., (1998).

Aggarwal, S.K., et al., "Determiniation of lead in urine and whole blood by stable isotope dilution gas chromatography-mass spectrometry"., Clinical Chemistry, vol. 40, No. 8, pp. 1494-1502, (1994).

Alivisatos, A.P., et al., "Organization of 'nanocrystal molecules' using DNA"., Nature, vol. 382, pp. 609-611, (1996).

Allara, D. et al., "Spontaneously organized molecular assemblies. 1.Formation, dynamics and physical properties on n-alkanoic acids adsorbed from solution on an oxidized aluminum surface"., Langmuir, vol. 1, No. 1. pp. 45-52, (1985).

Andreola, M-L., et al., "DNA aptamers selected against the HIV-1 RNase H display in vitro antiviral activity"., Biochemistry, vol. 40, No. 34, pp. 10087-10094, (2001).

Bain, C. D., et al., "Modeling organic surfaces with self-assembled monolayers"., Angew. Chem. Int. Ed. Engl., vol. 28, No. 4, pp. 506-512, (1989).

Bannon, D.I., et al., "Graphite furnace atomic absorption spectroscopic measurement of blood lead in matrix-matched standards"., Clinical Chemistry, vol. 40, No. 9, pp. 1730-1734, (1994).

Been, M.D., et al., "Self-cleaving ribozymes of hepatitis delta virus RNA"., Eur. J. Biochem., vol. 247, pp. 741-753, (1997).

Berens, C., et al., "A tetracycline-binding RNA aptamer"., Bioorganic & Medicinal Chemistry, vol. 9, pp. 2549-2556, (2001).

Biroccio, A., et al., "Selection of RNA aptamers that are specific and high-affinity ligands of the hepatitis C virus RNA-dependent RNA polymerase"., Journal of Virology, vol. 76, No. 8, pp. 3688-3696, (2002).

Blake, D.A., et al., "Antibody-based sensors for heavy metal ions"., Biosensors & Bioelectronics, vol. 16, pp. 799-809, (2001).

Blank, M., et al., "Systematic evolution of a DNA aptamer binding to rat brain tumor microvessles. Selective targeting of endothelial regulatory protein pigpen"., Journal of Biological Chemistry, vol. 276, No. 19, pp. 16464-16468, (2001).

Bock, L.C., et al., "Selection of single-stranded DNA molecules that bind and inhibit human thrombin"., Nature, vol. 355, pp. 564-566, (1992).

Bogden, J.D., et al., "Soil contamination from lead in paint chips"., Bulletin of Environmental Contamination & Toxicology, vol. 14, No. 3, pp. 289-294, (1975).

Boiziau, C., et al., "DNA aptamers selected against the HIV-1 trans-activation-responsive RNA element form RNA-DNA kissing complexes"., Journal of Biological Chemistry, vol. 274, No. 18, pp. 12730-12737, (1999).

Bowins, R.J., et al., "Electrothermal isotope dilution inductively coupled plasma mass spectrometry method for the determination of sub-ng ml$^{-1}$ levels of lead in human plasma"., Journal of Analytical Atomic Spectrometry, vol. 9, pp. 1233-1236, (1994).

Breaker, R.R., "Catalytic DNA: in training and seeking employment"., Nature Biotechnology, vol. 17, pp. 422-423, (1999).

Breaker, R.R., "DNA aptamers and DNA enzymes" Current Opinion in Chemical Biology, vol. 1, pp. 26-31, (1997).

Breaker, R.R., "DNA enzymes"., Nature Biotechnology, vol. 15, pp. 427-431, (1997).

Breaker, R.R., "Molecular Biology: Making Catalytic DNAs"., Science, vol. 290, issue 5499, pp. 2095-2096, (2000).

Breaker, R.R., et al., "A DNA enzyme that cleaves RNA"., Chemistry & Biology, vol. 1, No. 4, pp. 223-229, (1994).

Breaker, R.R., et al., "A DNA enzyme with Mg$^{2+}$-dependent RNA phosphoesterase activity"., Chemistry & Biology, vol. 2, No. 10, pp. 655-660, (1995).

Breaker, R.R., et al., "Engineered allosteric ribozymes as biosensor components"., Current Opinion in Biotechnology, vol. 13, pp. 31-39, (2002).

Brody, E.N., et al., "Aptamers as therapeutic and diagnostic agents"., Reviews in Molecular Biotechnology, vol. 74, pp. 5-13, (2000).

Broude, N.E., "Stem-loop oligonucleotides: a robust tool for molecular biology and biotechnology", Trends in Biotechnology, vol. 20, No. 6, pp. 249-256, (2002).

Brown, A.K., et al., "A lead-dependent DNAzyme with a two-step mechanism"., Biochemistry, vol. 42, No. 23, pp. 7152-7161, (2003).

Bruesehoff, P.J., et al., "Improving metal ion specificity during In Vitro selection of catalytic DNA"., Combinatorial Chemistry & High Throughput Screening, vol. 5, pp. 327-335, (2002).

Bruno, J.G., et al., "In vitro selection of DNA aptamers to anthrax spores with electrochemiluminescence detection"., Biosensors & Bioelectronics, vol. 14, pp. 457-464, (1999).

Bruno, J.G., et al., "Use of magnetic beads in selection and detection of biotoxin aptamers by electrochemiluminescence and enzymatic methods"., BioTechniques, vol. 32, No. 1, pp. 178-180, pp. 182-183, (2002).

Brust, M., et al., "Novel gold-dithiol nano-networks with non-metallic electronic properties"., Advanced Materials, vol. 7, No. 9, pp. 795-797, (1995).

Burdette, S.C., et al., "Fluorescent Sensors for $Zn^{2+}$ Based on a Fluorescein Platform: Synthesis, Properties and Intracellular Distribution"., J. Am. Chem. Soc., vol. 123, No. 32, pp. 7831-7841, (2001).

Burgstaller, P., et al., "Isolation of RNA aptamers for biological cofactors by in vitro selection"., Angew. Chem. Int. Ed. Engl, vol. 33, No. 10, pp. 1084-1087, (1994).

Burgstaller, P., et al., "Structural probing and damage selection of citrulline- and arginine-specific RNA aptamers identify base positions required for binding"., Nucleic Acids Research, vol. 23, No. 23, pp. 4769-4776, (1995).

Burke, D.H., et al., "A Novel Acidophilic RNA Motif That Recognizes Coenzyme A"., Biochemistry, vol. 37, No. 13, pp. 4653-4663, (1998).

Burke, D.H., et al., "RNA aptamers to the adenosine moiety of S-adenosyl methionine: structural inferences from variations on a theme and the reproducibility of SELEX"., Nucleic Acids Research, vol. 25, No. 10, pp. 2020-2024, (1997).

Burke, D.H., et al., "RNA aptamers to the peptidyl transferase inhibitor chloramphenicol"., Chemistry & Biology, vol. 4, No. 11, pp. 833-843, (1997).

Burmeister, J., et al., "Cofactor-assisted self-cleavage in DNA libraries with a 3'-5'-phosphoramidate bond"., Angew. Chem. Int. Ed. Engl., vol. 36, No. 12, pp. 1321-1324, (1997).

Burwell Jr., R.L., "Modified silica gels as adsorbents and catalysts"., Chemical Technology, 4, pp. 370-377, (1974).

Cadwell, R.C., et al., "Mutagenic PCR"., PCR Methods and Applications, vol. 3, pp. S136-S140, (1994).

Cadwell, R.C., et al., "Randomization of genes by PCR mutagenesis"., PCR Methods and Applications, vol. 2, pp. 28-33, (1992).

Cake, K.M., et al., "In vivo x-ray fluorescence of bone lead in the study of human lead metabolism: serum lead, whole blood lead, bone lead, and cumulative exposure"., Advances in X-Ray Analysis, vol. 38, pp. 601-606, (1995).

Camara Rica, C., et al., "Determination of trace concentrations of lead and nickel in human milk by electrothermal atomisation atomic absorption spectrophotometry and inductively coupled plasma emission spectroscopy"., The Science of the Total Environment, vol. 22, pp. 193-201, (1982).

Cao, Y.W., et al., "DNA-modified core-shell Ag/Au nanoparticles"., J. Am. Chem. Soc., vol. 123, No. 32, pp. 7961-7962, (2001).

Carmi, N., et al., "Cleaving DNA with DNA"., Proc. Natl. Acad. Sci. USA, vol. 95, pp. 2233-2237, (1998).

Carmi, N., et al., "In vitro selection of self-cleaving DNAs"., Chemistry & Biology, vol. 3, No. 12, pp. 1039-1046, (1996).

Cech, T.R., "Structure and mechanism of the large catalytic RNAs: group I and group II introns and ribonuclease P"., The RNA World, pp. 239-269, Cold Spring Harbor Laboratory Press, Cold Spring Harbor, New York, (1993).

Cech, T.R., et al., "Group I ribozymes: substrate recognition, catalytic strategies, and comparative mechanistic analysis"., Nucleic Acids and Molecular Biology, vol. 10, pp. 1-17, (1996).

Chaloin, L., et al., "Endogenous expression of a high-affinity pseudoknot RNA aptamer suppresses replication of HIV-1"., Nucleic Acids Research, vol. 30, No. 18, pp. 4001-4008, (2002).

Chapman, K.B., et al., "In vitro selection of catalytic RNAs"., Current Opinion in Structural Biology, vol. 4, pp. 618-622, (1994).

Chartrand, P., et al., "Effect of structural modifications on the activity of the leadzyme"., Biochemistry, vol. 36, No. 11, pp. 3145-3150, (1997).

Chen, J., et al., "Synthesis from DNA of a molecule with the connectivity of a cube"., Nature, vol. 350, pp. 631-633, (1991).

Chen, C-T., et al., "A highly selective fluorescent chemosensor for lead ions"., J. Am. Chem. Soc., vol. 124, pp. 6246-6247, (2002).

Chen, J-H., et al., "A specific quadrilateral synthesized from DNA branched junctions"., J. Am. Chem. Soc., vol. 111, No. 16, pp. 6402-6407, (1989).

Chen, L., et al., "Crystal structure of a four-stranded intercalated DNA: $d(C_4)$"., Biochemistry, vol. 33, No. 46, pp. 13540-13546, (1994).

Chinnapen, D.J.F., et al., "Hemin-stimulated docking of cytochrome c to a hemin—DNA aptamer complex"., Biochemistry, vol. 41, No. 16, pp. 5202-5212, (2002).

Ciesiolka, J., et al., "Selection of an RNA domain that binds $Zn^{2+}$"., RNA, vol. 1, pp. 538-550, (1995).

Ciesiolka, J., et al., "Small RNA-divalent domains"., RNA, vol. 2, pp. 785-793, (1996).

Conaty, J., et al., "Selected classes of minimised hammerhead ribozyme have very high cleavage rates at low $Mg^{2+}$ concentration"., Nucleic Acids Research, vol. 27, No. 11, pp. 2400-2407, (1999).

Conn, M.M., et al., "Porphyrin Metalation Catalyzed by a Small RNA Molecule"., J. Am. Chem. Soc, vol. 118, No. 29, pp. 7012-7013, (1996).

Connell, G.J., et al., "RNAs with dual specificity and dual RNAs with similar specificity"., Science, New Series, vol. 264, issue 5162, pp. 1137-1141, (1994).

Connell, G.J., et al., "Three small ribooligonucleotides with specific arginine sites"., Biochemistry, vol. 32, No. 21, pp. 5497-5502, (1993).

Cuenoud, B., et al., "A DNA metalloenzyme with DNA ligase activity"., Nature, vol. 375, pp. 611-614, (1995).

Czarnik, A.W., "Desperately seeking sensors"., Chemistry & Biology, vol. 2, No. 7, pp. 423-428, (1995).

Dai, X., et al., "Cleavage of an amide bond by a ribozyme"., Science, New Series, vol. 267, issue 5195, pp. 237-240, (1995).

Davis, J.H., et al., "Isolation of high-affinity GTP aptamers from partially structured RNA libraries"., Proc. Natl. Acad. Sci. USA, vol. 99, No. 18, pp. 11616-11621, (2002).

Davis, K.A., et al., "Staining of cell surface human CD4 with 2'-F-pyrimidine-containing RNA aptamers for flow cytometry"., Nucleic Acids Research, vol. 26, No. 17, pp. 3915-3924, (1998).

Definition of the world "ion" printed from Merriam-Webster online dictionary (www.m-w.com) on Jun. 30, 2004.

Definition of the word "particle" printed from Merriam-Webster online dictionary (www.m-w.com) on Jun. 29, 2004.

Deo, S., et al., "A Selective, Ratiometric Fluorescent Sensor for $Pb^{2+}$"., J. Am. Chem. Soc., vol. 122, No. 1, pp. 174-175, (2000).

Derose, V.J., "Two Decades of RNA Catalysis"., Chemistry & Biology, vol. 9, pp. 961-969, (2002).

Didenko, V.V., "DNA probes using fluorescence resonance energy transfer (FRET): Designs and applications"., BioTechniques, vol. 31, pp. 1106-1121, (2001). We have reference, but we are missing pp. 1119-1121.

Dounda, J.A., et al., "The Chemical Repertoire of Natural Ribozymes"., Nature, vol. 418, pp. 222-228, (2002).

Dubois, L.H., et al., "Synthesis, structure, and properties of model organic surfaces"., Annu. Rev. Phys. Chem., vol. 43, pp. 437-463, (1992).

Earnshwa, D.J., et al., "Modified oligoribonucleotides as site-specific probes of RNA structure and function"., Biopolymers (Nucleic Acid Sciences), vol. 48, pp. 39-55, (1998).

Ekland, E.H., et al., "RNA-catalyzed RNA polymerization using nucleoside triphosphates"., Nature, vol. 382, pp. 373-376, (1996).

Ekland, E.H., et al., "Structurally complex and highly active RNA ligases derived from random RNA sequences"., Science, vol. 269, issue 5222, pp. 364-370, (1995).

Elghanian, R., et al., "Selective colorimetric detection of polynucleotides based on the distance-dependent optical properties of gold nanoparticles"., Science, vol. 277, pp. 1078-1081, (1997).

Ellington, A.D., et al., "Aptamers as potential nucleic acid pharmaceuticals"., Biotechnology Annual Review, vol. 1, pp. 185-214, (1995).

Ellington, A.D., et al., "In vitro selection of RNA molecules that bind specific liagnds"., Nature, vol. 346, pp. 818-822, (1990).

Ellington, A.D., et al., "Selection in vitro of single-stranded DNA molecules that fold into specific ligand-binding structures"., Nature, vol. 355, pp. 850-852, (1992).

Famulok, M., "Molecular Recognition of Amino Acids by RNA-Aptamers: An L-Citrulline Binding RNA Motif and Its Evolution into an L-Arginine Binder"., J. Am. Chem. Soc., vol. 116, No. 5, pp. 1698-1706, (1994).

Famulok, M., "Oligonucleotide aptamers that recognize small molecules", Current Opinion in Structural Biology, vol. 9, pp. 324-329, (1999).

Famulok, M., et al., "In Vitro Selection Analysis of Neomycin Binding RNAs with a Mutagenized Pool of Variants of the 16S rRNA Decoding Region"., Biochemistry, vol. 35, No. 14, pp. 4265-4270, (1996).
Famulok, M., et al., "Stereospecific recognition of tryptophan agarose by in vitro selected RNA"., J. Am. Chem. Soc., vol. 114, No. 10, pp. 3990-3991, (1992).
Faulhammer, D., et al., "Characterization and Divalent Metal-ion Dependence of in Vitro Selected Deoxyribozymes which Cleave DNA/RNA Chimeric Oligonucleotides"., J. Mol. Biol., vol. 269, pp. 188-202, (1997).
Faulhammer, D., et al., "The $Ca^{2+}$ ion as a cofactor for a novel RNA-cleaving deoxyribozyme"., Angew. Chem., Int. Ed. Engl., vol. 35, No. 23/24, pp. 2837-2841, (1996).
Feldman, B.J., et al., "Determination of lead in blood by square wave anodic stripping voltammetry at a carbon disk ultramicroelectrode"., Analytical Chemistry, vol. 66, No. 13, pp. 1983-1987, (1994).
Ferguson, A., et al., "A novel strategy for selection of allosteric ribozymes yields riboreporter™ sensors for caffeine and aspartame"., Nucleic Acids Research, vol. 32, No. 5, pp. 1756-1766, (2004).
Fodor, S.P.A., et al., "Light-directed, spatially addressable parallel chemical synthesis"., Science, New Series, vol. 251, issue 4995, pp. 767-773, (1991).
Frank, D.N., et al., "In vitro selection for altered divalent metal specificity in the RNase P RNA"., Proc. Natl. Acad. Sci. USA, vol. 94, pp. 14355-14360, (1997).
Frens, G., et al., "Controlled Nucleation for the regulation of the particle size in monodisperse gold suspensions", Nature Physical Science, vol. 241, pp. 20-22, (1973).
Fukusaki, E-I., et al., "DNA aptamers that bind to chitin"., Bioorganic & Medicinal Chemistry letters, vol. 10, pp. 423-425, (2000).
Geiger, A., et al., "RNA aptamers that bind L-arginine with sub-micromolar dissociation constants and high enantioselectivity"., Nucleic Acids Research, vol. 24, No. 6, pp. 1029-1036, (1996).
Geyer, C.R., et al., "Evidence for the metal-cofactor independence of an RNA phosphodiester-cleaving DNA enzyme"., Chemistry & Biology, vol. 4, No. 8, pp. 579-593, (1997).
Geyer, C.R., et al., "Lanthanide Probes for a Phosphodiester-cleaving, Lead-dependent, DNAzyme", J. Mol. Biol., vol. 275, pp. 483-489, (1998).
Giver, L., et al., "Selection and design of high-affinity RNA ligands for HIV-1 Rev"., Gene, vol. 137, pp. 19-24, (1993).
Giver, L., et al., "Selective optimization of the Rev-binding element of HIV-1".,Nucleic Acids Research, vol. 21, No. 23, pp. 5509-5516, (1993).
Godwin, H.A., et al., "A Flourescent Zinc Probe Based on Metal-Induced Peptide Folding"., J. Am. Chem. Soc., vol. 118, pp. 6514-6515, (1996).
Grabar, K., et al., "Preparation and characterization of Au colloid Monolayers"., Analytical chemistry, vol. 67, No. 4, pp. 735-743, (1995).
Granadillo, V.A., et al., "The influence of the bood levels of lead, aluminum and vanadium upon the arterial hypertension"., Clinica Chimica Acta, vol. 233, pp. 47-59, (1995).
Grate, D., et al., "Laser-mediated, site-specific inactivation of RNA transcripts"., Proc. Natl. Acad. Sci. USA, vol. 96, pp. 6131-6136, (1999).
Guschin, D., et al., "Manual manufacturing of oligonucleotide, DNA, and protein microchips"., Analytical Biochemistry, vol. 250, pp. 203-211, (1997).
Haller, A.A., et al., "In vitro selection of a 7-methyl-guanosine binding RNA that inhibits translation of capped mRNA molecules"., Proc. Natl. Acad. Sci. USA, vol. 94, pp. 8521-8526, (1997).
Harada, K., et al., "Identification of two novel arginine binding DNAs"., The EMBO Journal, vol. 14, No. 23, pp. 5798-5811, (1995).
Hartig, J.S., et al., "Reporter ribozymes for real-time analysis of domain-specific interactions in biomolecules: HIV-1 reverse transcriptase and the primer-template complex"., Angew. Chem. Int. Ed., vol. 41, No. 22, pp. 4263-4266, (2002).

He, X-x., et al., "Bioconjugated nanoparticles for DNA protection from cleavage"., J. Am. Chem. Soc., vol. 125, No. 24, pp. 7168-7169, (2003).
Hennrich, G., et al., "Redox switchable fluorescent probe selective for either Hg(II) or Cd(II) and Zn(II)" J. Am. Chem. Soc., vol. 121, No. 21, pp. 5073-5074, (1999).
Hesselberth, J., et al., "In vitro selection of nucleic acids for diagnostic applications"., Reviews in Molecular Biotechnology, vol. 74, pp. 15-25, (2000).
Hesselberth, J.R., et al., "Simultaneous detection of diverse analytes with an aptazyme ligase array", Analytical Biochemistry vol. 312, pp. 106-112, (2003).
Ho, H-A., et al., "Optical sensors based on hybrid aptamer/conjugated polymer complexes"., J. Am. Chem. Soc., vol. 126, No. 5, pp. 1384-1387, (2004).
Hock, B., "Antibodies for immunosensors, A review"., Analytica Chimica Acta, vol. 347, pp. 177-186, (1997).
Hofmann, H.P., et al., "$Ni^{2+}$-binding RNA motifs with an asymmetric purine-rich internal loop and a G-A base pair"., RNA, vol. 3, pp. 1289-1300, (1997).
Holeman, L.A., et al., "Isolation and characterization of fluorophore-binding RNA aptamers"., Folding & Design, vol. 3, pp. 423-431, (1998).
Hoogstraten, C.G., et al., "NMR solution structure of the lead-dependent ribozyme: Evidence for dynamics in RNA catalysis"., J. Mol. Biol., vol. 284, pp. 337-350, (1998).
Hoogstraten, C.G., et al., "Structural analysis of metal ion ligation to nucleotides and nucleic acids using pulsed EPR spectroscopy"., J. Am. Chem. Soc., vol. 124, No. 5, pp. 834-842, (2002).
Huizenga, D.E., et al., "A DNA aptamer that binds adenosine and ATP"., Biochemistry, vol. 34, No. 2, pp. 656-665, (1995).
Iler, R.K., "The Chemistry of Silica: Solubility, Polymerization, Colloid and Surface Properties, and Biochemistry, Chapter 6, The surface chemistry of silica"., pp. 622-729, A Wiley-Interscience Publication, New York, (1979).
Illangasekare, M., et al., "Small-molecule-substrate interactions with a self-aminoacylating ribozyme"., J. Mol. Biol., vol. 268, pp. 631-639, (1997).
Imperiali, B., et al., "Peptide platforms for metal ion sensing"., Proc. SPIE-The international society for optical engineering, vol. 3858, pp. 135-143, (1999).
International Search Report dated Jan. 15, 2003 for corresponding PCT application No. PCT/US01/20557.
International Search Report dated Aug. 1, 2003 for corresponding PCT application No. PCT/US03/08483.
Iqbal, S.S., et al., "A review of molecular recognition technologies for detection of biological threat agents"., Biosensors & Bioelectronics, vol. 15, pp. 549-578, (2000).
Jagner, D., et al., "Determination of lead in microliter amounts of whole blood by stripping potentiometry"., Electroanalysis, vol. 6, pp. 285-291, (1994).
Jayasena, S.D., "Aptamers: an emerging class of molecules that rival antibodies in diagnostics"., Clinical Chemistry, vol. 45, No. 9, pp. 1628-1650, (1999).
Jenison, R., et al., "Interference-based detection of nucleic acid targets on optically coated silicon"., Nature Biotechnology, vol. 19, pp. 62-65, (2001).
Jenison, R.D., et al., "High-resolution molecular discrimination by RNA"., Science, vol. 263, pp. 1425-1429, (1994).
Jenne, A., et al., "Rapid Identification and Characterization of Hammerhead-Ribozyme Inhibitors Using Fluorescence-Based Technology"., Nature Biotechnology, vol. 19, pp. 56-61, (2001).
Jenne, A., et al., "Real-time Characterization of Ribozymes by Fluorescence Resonance Energy Transfer (FRET)"., Angewandte Chemie. International Edition, vol. 38, No. 9, pp. 1300-1303, (1999).
Jhaveri, S., et al., "In vitro selection of signaling aptamers"., Nature Biotechnology, vol. 18, pp. 1293-1297, (2000).
Jhaveri, S.D., et al., "Designed signaling aptamers that transduce molecular recognition to changes in fluorescence intensity"., J. Am. Chem. Soc., vol. 122, No. 11, pp. 2469-2473, (2000).
Jin, R., et al., "What controls the melting properties of DNA-linked gold nanoparticle assemblies?"., J. Am. Chem. Soc., vol. 125, No. 6, pp. 1643-1654, (2003).

Joos, B., et al., "Covalent attachment of hybridizable oligonucleotides to glass supports"., Analytical Biochemistry, vol. 247, pp. 96-101, (1997).

Josephson, L., et al., "Magnetic nanosensors for the detection of oligonucleotide sequences"., Angewandte Chemie. International Edition, vol. 40, No. 17, pp. 3204-3206, (2001).

Joyce, G.F., "Appendix 3: Reactions Catalyzed by RNA and DNA Enzymes". The RNA World, vol. 37, pp. 687-690, Cold Spring Harbor Laboratory Press, Cold Spring Harbor, New York, (1999).

Joyce, G.F., "In vitro evolution of nucleic acids"., Current Opinin in Structural Biology, vol. 4, pp. 331-336, (1994).

Katahira, M., et al., "Two metal-binding sites in a lead ribozyme bound to competitively by $Pb^{2+}$ and $Mg^{2+}$: Induced structural changes as revealed by NMR"., European Journal of Biochemistry, vol. 255, pp. 727-733, (1998).

Kato, T., et al., "In vitro selection of DNA aptamers which bind to cholic acid"., Biochimica et Biophysica Acta, vol. 1493, pp. 12-18, (2000).

Kawakami, J., et al., "In vitro selection of aptamers that act with $Zn^{2+}$"., Journal of Inorganic Biochemistry, vol. 82, pp. 197-206, (2000).

Khan, R., et al., "Interaction of retroviral nucleocapsid proteins with transfer $RNA^{Phe}$: a lead ribozyme and $^1H$ NMR study"., Nucleic Acids Research, vol. 24, No. 18, pp. 3568-3575, (1996).

Khosraviani, M., et al., "Detection of heavy metals by immunoassay: Optimization and validation of a rapid, portable assay for ionic cadmium"., Environ. Sci. Technol., vol. 32, No. 1, pp. 137-142, (1998).

Kiga, D., et al., "An RNA aptamer to the xanthine/guanine base with a distinctive mode of purine recognition"., Nucleic Acids Research, vol. 26, No. 7, pp. 1755-1760, (1998).

Kim, M.H., et al., "Activation and repression of the activity of a lead ribozyme by the combination of $Pb^{2+}$ and $Mg^{2+1}$"., J. Biochem., vol. 122, No. 5, pp. 1062-1067, (1997).

Klußmann, S., et al., "Mirror-image RNA that binds D-adenosine"., Nature Biotechnology, vol. 14, pp. 1112-1115, (1996).

Kohama, T., et al., "Molecular Cloning and Functional Characterization of Murine Sphingosine Kinase", The Journal of Biological Chemistry, vol. 273, No. 37, pp. 23722-23728, (1998).

Koizumi, M., et al., "Allosteric selection of ribozymes that respond to the second messengers cGMP and cAMP"., Nature Structural Biology, vol. 6, No. 11, pp. 1062-1071, (1999).

Koizumi, M., et al., "Molecular Recognition of cAMP by an RNA Aptamer"., Biochemistry, vol. 39, No. 30, pp. 8983-8992, (2000).

Koizumi, M., et al., "Allosteric ribozymes sensitive to the second messengers cAMP and cGMP"., Nucleic Acids Symposium Series, No. 42, pp. 275-276, (1999).

Kruger, K., et al., "Self-splicing RNA: autoexcision and autocyclization of the ribosomal RNA intervening sequence of the Tetrahymena"., Cell, vol. 31, pp. 147-157, (1982).

Lato, S.M., et al., "In vitro selection of RNA lectins: Using combinatorial chemistry to interpret ribozyme evolution"., Chemistry & Biology, vol. 2, No. 5, pp. 291-303, (1995).

Lauhon, C.T., et al., "RNA aptamers that bind flavin and nicotinamide redox cofactors"., J. Am. Chem. Soc., vol. 117, No. 4, pp. 1246-1257, (1995).

Lebruska, L.L., "Selection and Characterization of an RNA Decoy for Transcription Factor NF-κB"., Biochemistry, vol. 38, No. 10, pp. 3168-3174, (1999).

Lee, M., et al., "A fiber-optic microarray biosensor using aptamers as receptors"., Analytical Biochemistry, vol. 282, pp. 142-146, (2000).

Lee, S-W., et al., "Ordering of quantum dots using genetically engineered viruses"., Science, vol. 296, pp. 892-895, (2002).

Legault, P., et al., "Order, dynamics and metal-binding in the lead-dependent ribozyme"., J. Mol. Biol., vol. 284, pp. 325-335, (1998).

Lehman, N., et al., "Evolution in vitro of an RNA enzyme with altered metal dependence"., Nature, vol. 361, pp. 182-185, (1993).

Lemieux, S., et al., "Modeling active RNA structures using the intersection of conformational space: application to the lead-activated ribozyme"., RNA, vol. 4, pp. 739-749, (1998).

Levy, M., et al., "ATP-Dependent Allosteric DNA Enzymes"., Chemistry & Biology, vol. 9, pp. 417-426, (2002).

Li, J., et al., "A highly sensitive and selective catalytic DNA biosensor for lead ions"., J. Am. Chem. Soc., vol. 122, No. 42, pp. 10466-10467, (2000).

Li, J., et al., "In vitro selection and characterization of a highly efficient Zn(II)-dependent RNA-cleaving deoxyribozyme"., Nucleic Acids Research, vol. 28, No. 2, pp. 481-488, (2000).

Li, J.J., et al., "Using molecular beacons as a sensitive fluorescence assay for enzymatic cleavage of single-stranded DNA"., Nucleic Acids Research, vol. 28, No. 11, e52, pp. i-vi, (2000).

Li, Y., et al., "A catalytic DNA for porphyrin metallation"., Nature Structural Biology, vol. 3, No. 9, pp. 743-747, (1996).

Li, Y., et al., "Capping DNA with DNA"., Biochemistry, vol. 19, No. 11, pp. 3106-3114, (2000).

Li, Y., et al., "Deoxyribozymes: new players in the ancient game of biocatalysis"., Current Opinion in Structural Biology, vol. 9, pp. 315-323, (1999).

Li, Y., et al., "Phosphorylating DNA with DNA"., Proc. Natl. Acad. Sci. USA, vol. 96, pp. 2746-2751, (1999).

Link, S., et al., "Alloy formation of gold-silver nanoparticles and the dependence of the plasmon absorption on their composition"., J. Phys. Chem. B, vol. 103, No. 18, pp. 3529-3533, (1999).

Liu, H-W., et al., "Determination of cadmium, mercury and lead in seawater by electrothermal vaporization isotope dilution inductively coupled plasma mass spectrometry"., Spectrochimica Acta Part B Atomic Spectroscopy 54, pp. 1367-1375, (1999).

Liu, J., et al., "A colorimetric lead biosensor using DNAzyme-directed assembly of gold nanoparticles", J. Am. Chem. Soc., vol. 125, No. 22, pp. 6642-6643, (2003).

Liu, J., et al., "Accelerated color change of gold nanoparticles assembled by DNAzymes for simple and fast colorimetric $Pb^{2+}$ detection"., J. Am. Chem. Soc., vol. 126, No. 39, pp. 12298-12305, (2004).

Liu, J., et al., "Adenosine-dependent assembly of aptazyme-functionalized gold nanoparticles and its application as a colorimetric biosensor"., Analytical Chemistry, vol. 76, No. 6, pp. 1627-1632, (2004).

Liu, J., et al., "Colorimetric biosensors based on DNAzyme-assembled gold nanoparticles"., Journal of Fluorescence, vol. 14, No. 4, pp. 343-354, (2004).

Liu, J., et al., "Highly dispersible molecular sieve carbon nanoparticles"., Chem. Mater., vol. 16, No. 22, pp. 4205-4207, (2004).

Liu, X., et al., "A fiber-optic evanescent wave DNA biosensor based on novel molecular beacons"., Analytical Chemistry, vol. 71, No. 22, pp. 5054-5059, (1999).

Liu, Z., et al., "Assemblage of signaling DNA enzymes with intriguing metal-ion specificities and pH dependences"., J. Am. Chem. Soc., vol. 125, No. 25, pp. 7539-7545, (2003).

Lohse, P.A., et al., "Ribozyme-catalysed amino-acid transfer reactions"., Nature, vol. 381, pp. 442-444, (1996).

Lorsch, J.R., et al., "In Vitro evolution of new ribozymes with polynucleotide kinase activity"., Nature, vol. 371, pp. 31-36, (1994).

Lorsch, J.R., et al., "In vitro selection of RNA aptamers specific for cyanocobalamin"., Biochemistry, vol. 33, No. 4, pp. 973-982, (1994).

Lott, W.B., et al., "A two-metal ion mechanism operates in the hammerhead ribozyme-mediated cleavage of an RNA substrate"., Proc. Natl. Acad. Sci. USA, vol. 95, pp. 542-547, (1998).

Lu, Y., "New transition-metal-dependent DNAzymes as efficient endonucleases and as selective metal biosensors"., Chem. Eur. J., vol. 8, No. 20, pp. 4589-4596, (2002).

Lu, Y., et al., "New fluorescent and colorimetric DNAzyme biosensors for metal ions", Journal of Inorganic Biochemistry, vol. 96, issue 1, pp. 30, abstract of the 11$^{th}$ International Conference on Biological Inorganic Chemistry; (Jul. 15, 2003).

Majerfeld, I., et al., "An RNA pocket for an aliphatic hydrophobe"., Structural Biology, vol. 1, No. 5, pp. 287-292, (1994).

Majerfeld, I., et al., "Isoleucine:RNA sites with associated coding sequences"., RNA, vol. 4, pp. 471-478, (1998).

Mannironi, C., et al., "In vitro selection of dopamine RNA ligands"., Biochemistry, vol. 36, No. 32, pp. 9726-9734, (1997).

Maoz, R., et al., "Penetration-controlled reaction in organized monolayer assemblies. 1. Aqueous permanganate interaction with monolayer and multilayer films of long-chain surfactants"., Langmuir, vol. 3, No. 6, pp. 1034-1044, (1987).

Marcus, A.H., et al., "Estimating the contribution of lead based paint to soil lead, dust lead, and childhood blood lead"., American Society for Testing and Materials Spec. STP 1226, pp. 12-23, (1995).

Marsh, T.C., et al., "A new DNA nanostructure, the G-wire, imaged by scanning probe microscopy"., Nucleic Acids Research, vol. 23, No. 4, pp. 696-700, (1995).

Matteucci, M.D., et al., "Synthesis of Deoxyoligonucleotides on a polymer support"., J. Am. Chem. Soc., vol. 103, No. 11, pp. 3185-3191, (1981).

Mecklenburg, M., et al., "A Strategy for the broad range detection of compounds with affinity for nucleic acids"., Analytica Chimica Acta, vol. 347, pp. 79-86, (1997).

Mei, S.H.J., et al., "An efficient RNA-cleaving DNA enzyme that synchronizes catalysis with fluorescence signaling"., J. Am. Chem. Soc., vol. 125, No. 2, pp. 412-420, (2003).

Meli, M., et al., "Adenine-aptamer complexes: A bipartite RNA site that binds the adenine nucleic base"., The Journal of Biological Chemistry, vol. 277, No. 3, pp. 2104-2111, (2002).

Mirkin, C.A., et al., "A DNA-based method for rationally assembling nanoparticles into macroscopic materials"., Nature, vol. 382, pp. 607-609, (1996).

Mirkin, S.M., et al., "H-DNA and related structures"., Annu. Rev. Biophys. Biomol. Struct., vol. 23, pp. 541-576, (1994).

Miyawaki, A., et al. "Fluorescent indicators for $Ca^{2+}$ based on green fluorescent proteins and calmodulin"., Nature, vol. 388, pp. 882-887, (1997).

Mucic, R.C., et al., "Synthesis and characterization of DNA with ferrocenyl groups attached to their 5'-termini: electrochemical characterization of a redox-active nucleotide monolayer"., Chem., Commun., pp. 555-557, (1996).

Mullah, B., et al., "Automated synthesis of double dye-labeled oligonucleotides using tetramethylrhodamine (TAMRA) solid supports"., Tetrahedron Letters, vol. 38, No. 33, pp. 5751-5754, (1997).

Nazarenko, I.A., et al., "A closed tube format for amplification and detection of DNA based on energy transfer"., Nucleic Acids Research, vol. 26, No. 12, pp. 2516-2521, (1997).

Nazarenko, I.A., et al., "Defining a Smaller RNA Substrate for Elongation Factor Tu"., Biochemistry, vol. 34, No. 8, pp. 2545-2552, (1995).

Niemeyer, C.M., "Nanoparticles, proteins, and nucleic acids: Biotechnology meets materials science"., Angew. Chem. Int. Edition, vol. 40, pp. 4128-4158, (2001).

Nieuwlandt, D., et al., "In Vitro Selection of RNA Ligands to Substance P"., Biochemistry, vol. 34, No. 16, pp. 5651-5659, (1995).

Nissen, P., et al., "The structural basis of ribosome activity in peptide bond synthesis"., Science, vol. 289, pp. 920-930, (2000).

Nolte, A., et al., "Mirror-design of L-oligonucleotide ligands binding to L-arginine"., Nature Biotechnology, vol. 14, pp. 1116-1119, (1996).

Nutiu, R., et al., "Structure-switching signaling aptamers"., J. Am. Chem. Soc., vol. 125, No. 16, pp. 4771-4778, (2003).

Nuzzo, R.G., et al., "Spontaneously organized molecular assemblies. 3. Preparation and properties of solution adsorbed monolayers of organic disulfides on gold surfaces"., J. Am. Chem. Soc., vol. 109, No. 8, pp. 2358-2368, (1987).

O'Donnell, M.J., et al., "High-Density, Covalent Attachment of DNA to Silicon Wafers for Analysis by MALDI-TOF Mass Spectrometry"., Analytical Chemistry, vol. 69, No. 13, pp. 2438-2443, (1997).

Oehme, I., et al., "Optical sensors for determination of heavy metal ions"., Mikrochim. Acta, vol. 126, pp. 177-192, (1997).

Ohmichi, T., et al., "Role of $Nd^{3+}$ and $Pb^{2+}$ on the RNA cleavage reaction by a small ribozyme"., Biochemistry, vol. 36, No. 12, pp. 3514-3521, (1997).

Ohmichi, T., et al., "Effect of substrate RNA sequence on the cleavage reaction by a short ribozyme"., Nucleic Acids Research, vol. 26, No. 24, pp. 5655-5661, (1998).

Okazawa, A., et al., "In vitro selection of hematoporphyrin binding DNA aptamers"., Bioorganic & Medicinal Chemistry, Letters 10, pp. 2653-2656, (2000).

Ota, N., et al., "Effects of helical structures formed by the binding arms of DNAzymes and their substrates on catalytic activity"., Nucleic Acids Research, vol. 26, No. 14, pp. 3385-3391, (1998).

Pan, T., et al., "A small metalloribozyme with a two-step mechanism"., Nature, vol. 358, pp. 560-563, (1992).

Pan, T., et al., "In vitro selection of RNAs that undergo autolytic cleavage with $Pb^{2+}$"., Biochemistry, vol. 31, No. 16, pp. 3887-3895, (1992).

Pan, T., et al., "Properties of an in vitro selected $Pb^{2+}$ cleavage motif"., Biochemistry, vol. 33, No. 32, pp. 9561-9565, (1994).

Pan, W., et al., "Isolation of virus-neutralizing RNAs from a large pool of random sequences"., Proc. Natl. Acad. Sci. USA, vol. 92, pp. 11509-11513, (1995).

Park, S-J., et al., "Array-based electrical detection of DNA with nanoparticle probes"., Science, vol. 295, pp. 1503-1506, (2002).

Parsons, P.J., et al., "A rapid Zeeman graphite furnace atomic absorption spectrometric method for the determination of lead in blood"., Spectrochimica Acta, vol. 48B, No. 6/7, p. 925-939, (1993).

Pavlov, A.R., et al., "Determination of lead in environmental water samples by a rapid and portable immunoassay"., ANYL, Book of Abstracts, 219th ACS National Meeting, San Francisco, CA, Mar. 26-30, 2000.

Pavlov, V., et al., "Aptamer-functionalized Au nanoparticles for the amplified optical detection of thrombin"., J. Am. Chem. Soc., vol. 126, No. 38, pp. 11768-11769, (2004).

Pearce, D.A., et al., "Peptidyl chemosensors incorporating a FRET mechanism for detection of Ni(II)"., Bioorganic & Medicinal Chemistry, Letters 8, pp. 1963-1968, (1998).

Pease, A.C., et al., "Light-generated oligonucleotide arrays for rapid DNA sequence analysis"., Proc. Natl. Acad. Sci. USA, vol. 91, pp. 5022-5026, (1994).

Piccirilli, J.A., et al., "Aminoacyl esterase activity of the tetrahymena ribozyme"., Science, New Series, vol. 256, issue 5062, pp. 1420-1424, (1992).

Pley, H.W., et al., "Three-dimensional structure of a hammerhead ribozyme"., Nature, vol. 372, pp. 68-74, (1994).

Potyrailo, R.A., et al., "Adapting selected nucleic acid ligands (aptamers) to biosensors"., Analytical Chemistry, vol. 70, No. 16, pp. 3419-3425, (1998).

Prudent, J.R., et al., "Expanding the scope of RNA catalysis"., Science, New Series, vol. 264, issue 5167, pp. 1924-1927, (1994).

Qiao, H., et al., "Transferability of blood lead determinations by furnace atomic absorption spectrophotometry and continuum background correction"., Clinical Chemistry, vol. 41, No. 10, pp. 1451-1454, (1995).

Rabinowitz, M., et al., "Home refinishing, lead paint, and infant blood lead levels"., American Journal of Public Health, vol. 75, No. 4, pp. 403-404, (1985).

Rajendran, M., et al., "Selecting nucleic acids for biosensor applications"., Combinatorial Chemistry and High Throughput Screening, vol. 5, No. 4, pp. 263-270, (2002).

Rakow, N.A., et al., "A colorimetric sensor array for odour visualization"., Nature, vol. 406, pp. 710-713, (2000).

Rink, S.M., et al., "Creation of RNA molecules that recognize the oxidative lesion 7,8-dihydro-8-hydroxy-2'-deoxyguanosine (8-oxodG) in DNA"., Proc. Natl. Acad. Sci. USA, vol. 95, pp. 11619-11624, (1998).

Robertson, M.P., et al., "Design and optimization of effector-activated ribozyme ligases"., Nucleic Acids Research, vol. 28, No. 8, pp. 1751-1759, (2000).

Robertson, M.P., et al., "In vitro selection of an allosteric ribozyme that transduces analytes to amplicons"., Nature Biotechnology, vol. 17, pp. 62-66, (1999).

Roth, A., et al., "An amino acid as a cofactor for a catalytic polynucleotide"., Proc. Natl. Acad. Sci. USA, vol. 95, pp. 6027-6031, (1998).

Roychowdhury-Saha, M., et al., "Flavin Recognition by an RNA Aptamer Targeted toward FAD"., Biochemistry, vol. 41, No. 8, pp. 2492-2499, (2002).

Ruckman, J., et al., "2'-Fluoropyrimidine RNA-based aptamers to the 165-amino acid form of vascular endothelial growth factor ($VEGF_{165}$) Inhibition of receptor binding and VEGF-induced vascular permeability through interactions requiring the exon 7-encoded domain"., The Journal of Biological Chemistry, vol. 273, No. 32, pp. 20556-20567, (1998).

Rurack, K., et al., "A selective and sensitive fluoroionphore for $Hg^{II}$, $Ag^{I}$, and $Cu^{II}$ with virtually decoupled fluorophore and receptor units"., J. Am. Chem. Soc., vol. 122, No. 5, pp. 968-969, (2000).

Rusconi, C.P., et al., "RNA aptamers as reversible antagonists of coagulation factor Ixa"., Nature, vol. 419, pp. 90-94, (2002).

Sabanayagam, C.R., et al., "Oligonucleotide immobilization on micropatterned streptavidin surfaces"., Nucleic Acids Research, vol. 28, No. 8, e33, pp. i-iv, (2000).

Santoro, S.W., et al., "Mechanism and utility of an RNA-cleaving DNA enzyme"., Biochemistry, vol. 37, No. 38, pp. 13330-13342, (1998).

Santoro, S.W., et al., "A general purpose RNA-cleaving DNA enzyme"., Proc. Natl. Acad. Sci. USA, vol. 94, pp. 4264-4266, (1997).

Santoro, S.W., et al., "RNA Cleavage by a DNA Enzyme with Extended Chemical Functionality"., J. Am. Chem. Soc. vol. 122, No. 11, pp. 2433-2439, (2000).

Sassanfar, M., et al., "An RNA motif that binds ATP"., Nature, vol. 364, pp. 550-553, (1993).

Schwartz, J., et al., "The risk of lead toxicity in homes with lead paint hazard"., Environmental Research, vol. 54, No. 1, pp. 1-7, (1991).

Scott, W.G., et al., "The crystal structure of an all-RNA hammerhead ribozyme: A proposed mechanism for RNA catalytic cleavage"., Cell, vol. 81, pp. 991-1002, (1995).

Scott, W.G., "RNA catalysis"., Current Opinion in Structural Biology, vol. 8, pp. 720-726, (1998).

Search results of key word search of medline, Mar. 26, 2000.

Search results of key word search on Chemical Abstracts, Mar. 24, 2000.

Search results of key word search from various databases, Mar. 24, 2000.

Seeman, N.C., et al., "Synthetic DNA knots and catenanes"., New Journal of Chemistry, vol. 17, pp. 739-755, (1993).

Seeman, N.C., et al., "Emulating biology: Building nanostructures from the bottom up"., Proc. Natl. Acad. Sci. vol. 99, suppl. 2, pp. 6451-6455, (2002).

Seeman, N.C., "DNA in a material world"., Nature, vol. 421, pp. 427-431, (2003).

Seetharaman, S., et al., "Immobilized RNA switches for the analysis of complex chemical and biological mixtures"., Nature Biotechnology, vol. 19, pp. 336-341, (2001).

Sen, D., et al., "DNA enzymes"., Current Opinion in Chemical Biology, vol. 2, pp. 680-687, (1998).

Shaiu, W-L., et al., "Atomic force microscopy of oriented linear DNA molecules labeled with 5nm gold spheres"., Nucleic Acids Research, vol. 21, No. 1, pp. 99-103, (1993).

Shaw, S.Y., et al., "Knotting of a DNA chain during ring closure"., Science, New Series, vol. 260, issue 5107, pp. 533-536, (1993).

Shekhtman, E.M., et al., "Stereostructure of replicative DNA catenanes from eukaryotic cells"., New Journal of Chemistry, vol. 17, pp. 757-763, (1993).

Sigurdsson, S.T., et al., "Small ribozymes"., RNA Structure and Function, Cold Spring Harbor Laboratory Press (Monograph 35), pp. 339-375, (1998).

Singh, K.K., et al., "Fluorescence Polarization for Monitoring Ribozyme Reactions in Real-Time"., Biotechniques, vol. 29, No. 2, pp. 344-351, (2000).

Smith, F.W., et al., "Quadruplex structure of oxytricha telomeric DNA oligonucleotides"., Nature, vol. 356, pp. 164-168, (1992).

Smith, J.O., et al., "Molecular recognition of PAN-containing hybrids: Spontaneous assembly of helical cyanine dye aggregates on PNA templates"., J. Am. Chem. Soc., vol. 121, No. 12, pp. 2686-2695, (1999).

Soriaga, M.P., et al., "Determination of the orientation of aromatic molecules adsorbed on platinum electrodes: The effect of solute concentration"., J. Am. Chem. Soc., vol. 104, No. 14, pp. 3937-3945, (1982).

Soukup, G.A., et al., "Engineering precision RNA molecular switches"., Proc. Natl. Acad. Sci. USA, vol. 96, pp. 3584-3589, (1999).

Soukup, G.A., et al., "Allosteric nucleic acid catalysts"., Current Opinion in Structural Biology, vol. 10, pp. 318-325, (2000).

Srisawat, C., et al., "Sephadex-binding RNA ligands: rapid affinity purification of RNA from complex RNA mixtures"., Nucleic Acids Research, vol. 29, No. 2 e4, pp. 1-5, (2001).

Stage-Zimmermann, T.K., et al., "Hammerhead ribozyme kinetics"., RNA, vol. 4, pp. 875-889, (1998).

Stojanovic, M.N., et al., "Aptamer-based colorimetric probe for cocaine"., J. Am. Chem. Soc., vol. 124, No. 33, pp. 9678-9679, (2002).

Stojanovic, M.N., et al., "Aptamer-based folding fluorescent sensor for cocaine"., Journal of the American Chemical Society, vol. 123, No. 21, pp. 4928-4931, (2001).

Stojanovic, M.N., et al., "Fluorescent sensors based on aptamer self-assembly"., Journal of the American Chemical Society, vol. 122, No. 46, pp. 11547-11548, (2000).

Storhoff, J.J., et al., "Programmed materials synthesis with DNA"., Chem. Rev., vol. 99, No. 7, pp. 1849-1862, (1999).

Storhoff, J.J., et al., "What Controls the Optical Properties of DNA-Linked Gold Nanoparticle Assemblies?"., J. Am. Chem. Soc., vol. 122, No. 19, pp. 4640-4650, (2000).

Storhoff, J.J., et al., "One-pot colorimetric differentiation of polynucleotides with single base imperfections using gold nanoparticle probes"., Journal of the American Chemical Society, vol. 120, No. 9, pp. 1959-1964, (1998).

Streicher, B., et al., "Lead cleavage site in the core structure of group I intron-RNA"., Nucleic Acids Research, vol. 21, No. 2, pp. 311-317, (1993).

Sugimoto, N., et al., "Site-specific cleavage reaction catalyzed by leadzyme is enhanced by combined effect of lead and rare earth ions"., FEBS Letters, vol. 393, pp. 97-100, (1996).

Sun, L.Q., et al., "Catalytic nucleic acids: From lab to applications"., Pharmacological Reviews, vol. 52, pp. 325-347, (2000).

Tahan, J.E., et al., "Electrothermal atomic absorption spectrometric determination of Al, Cu, Ge, Pb, V and Zn in clinical samples and in certified environmental reference materials"., Analytica Chimica Acta, vol. 295, pp. 187-197, (1994).

Takagi, Y., et al., "Survey and Summary: Recent advances in the elucidation of the mechanisms of action of ribozymes"., Nucleic Acids Research, vol. 29, No. 9, pp. 1815-1834, (2001).

Tang, J., et al., "Rational design of allosteric ribozymes"., Chemistry & Biology, vol. 4, No. 6, pp. 453-459, (1997).

Tang, J., et al., "Structural diversity of self-cleaving ribozymes"., Proc. Natl. Acad. Sci. USA, vol. 97, No. 11, pp. 5784-5789, (2000).

Tanner, N.K., "Biochemistry of hepatitis delta virus catalytic RNAs"., Ribozymes in the Gene Therapy of Cancer, Chapter 3, pp. 23-38, (1998).

Tao, J., et al., "Arginine-Binding RNAs Resembling TAR Identified by in Vitro Selection"., Biochemistry, vol. 35, No. 7, pp. 2229-2238, (1996).

Tarasow, T.M., et al., "RNA-catalysed carbon-carbon bond formation"., Nature, vol. 389, pp. 54-57, (1997).

Telting-Diaz, M., et al., "Mass-produced ionophore-based fluorescent microspheres for trace level determination of lead ions"., Analytical Chemistry, vol. 74, No. 20, pp. 5251-5256, (2002).

Thompson, R.B., et al., "Determination of Picomolar Concentrations of Metal Ions Using Fluorescence Anisotropy: Biosensing with a "Reagentless" Enzyme Transducer"., Analytical Chemistry, vol. 70, No. 22, pp. 4717-4723, (1998).

Timmons, C.O., et al., "Investigation of Fatty Acid Monolayers on Metals by Contact Potential Measurements", Journal of Physical Chemistry, vol. 69, No. 3, pp. 984-990, (1965).

Tompkins, H.G., et al., "The study of the gas-solid interaction of acetic acid with a cuprous oxide surface using reflection-absorption spectroscopy"., Journal of Colloid and Interface Science, vol. 49, No. 3, pp. 410-421, (1974).

Travascio, P., et al., "A ribozyme and a catalytic DNA with peroxidase activity: active sites versus cofactor-binding sites"., Chemistry & Biology, vol. 6, No. 11, pp. 779-787, (1999).

Tsang, J., et al., "In vitro evolution of randomized ribozymes"., Methods in Enzymology, vol. 267, pp. 410-426, (1996).

Tsien, R.Y., "Fluorescent and photochemical probes of dynamic biochemical signals inside living cells"., Fluorescent Chemosensors for Ion and Molecule Recognition, (ed. Czarnik, A. W.), chapter 9, pp. 130-146, American Chemical Society, (1993).

Tuerk, C., et al., "RNA pseudoknots that inhibit human immunodeficiency virus type 1 reverse transcriptase"., Proc. Natl. Acad. Sci. USA, vol. 89, pp. 6988-6992, (1992).

Tuerk, C., et al., "Systematic evolution of ligands by exponential enrichment: RNA ligands to bacteriophage T4 DNA polymerase"., Science, New Series, vol. 249, issue 4968, pp. 505-510, (1990).

Tyagi, S., et al., "Molecular Beacons: Probes that fluoresce upon hybridization"., Nature Biotechnology, vol. 14, pp. 303-308, (1996).

Tyagi, S., et al., "Multicolor molecular beacons for allele discrimination"., Nature Biotechnology, vol. 16, pp. 49-53, (1998).

Tyagi, S., et al., "Wavelength-shifting molecular beacons"., Nature Biotechnology, vol. 18, pp. 1191-1196, (2000).

Ueyama, H., "A novel potassium sensing in aqueous media with a synthetic oligonucleotide derivative, Fluorescence resonance energy tranfer associated with guanine quarter-potassium ion complex formation"., J. Am. Chem. Soc., vol. 124, No. 48, pp. 14286-14287, (2002).

Uphoff, K.W., et al., "In vitro selection of aptamers: the dearth of pure reason"., Current Opinion in Structural Biology, vol. 6, pp. 281-288, (1996).

Vaish, N.K., et al., "In vitro selection of a purine nucleotide-specific hammerhead-like ribozyme"., Proc. Natl. Acad. Sci. USA, vol. 95, pp. 2158-2162, (1998).

Valadkhan, S., et al., "Splicing-related catalysis by protein-free snRNAs"., Nature, vol. 413, pp. 701-707, (2001).

Vianini, E., et al., "In vitro selection of DNA aptamers that bind L-tyrosinamide"., Bioorganic & Medicinal Chemistry, vol. 9, pp. 2543-2548, (2001).

Walkup, G.K., et al., "Design and Evaluation of a Peptidyl Fluorescent Chemosensor for Divalent Zinc"., J. Am. Chem. Soc., vol. 118, No. 12, pp. 3053-3054, (1996).

Wallace, S.T., et al., In vitro selection and characterization of streptomycin-binding RNAs: recognition discrimination between antibiotics, RNA, vol. 4, pp. 112-123, (1998).

Wallis, M.G., et al., "A novel RNA motif for neomycin recognition"., Chemistry & Biology, vol. 2, No. 8, pp. 543-552, (1995).

Wallis, M.G., et al., "In vitro selection of a viomycin-binding RNA pseudoknot"., Chemistry & Biology, vol. 4, No. 5, pp. 357-366, (1997).

Walter, F., et al., "Folding of the four-way RNA junction of the hairpin ribozyme"., Biochemistry, vol. 37, No. 50, pp. 17629-17636, (1998).

Walter, N.G., et al., "The hairpin ribozyme: structure, assembly and catalysis"., Current Opinion in Chemical Biology, vol. 2, pp. 24-30, (1998).

Wang, D.Y., et al., "A general strategy for effector-mediated control of RNA-cleaving ribozymes and DNA enzymes"., J. Mol. Biol., vol. 318, pp. 33-43, (2002).

Wang, F., et al., "Sphingosine-1-phosphate Inhibits Motility of Human Breast Cancer Cells Independently of Cell Surface Receptors"., Cancer Research, vol. 59, pp. 6185-6191, (1999).

Wang, J., "Survey and Summary: From DNA biosensors to gene chips"., Nucleic Acids Research, vol. 28, No. 16, pp. 3011-3016, (2000).

Wang, K.Y., et al., "A DNA aptamer which binds to and inhibits thrombin exhibits a new structural motif for DNA"., Biochemistry, vol. 32, No. 8, pp. 1899-1904, (1993).

Wang, Y., et al., "Assembly and characterization of five-arm and six-arm DNA branched junctions"., Biochemistry, vol. 30, pp. 5667-5674, (1991).

Wang, Y., et al., "RNA molecules that specifically and stoichiometrically bind aminoglycoside antibiotics with high affinities"., Biochemistry, vol. 35, No. 38, pp. 12338-12346, (1996).

Wecker, M., et al., "In vitro selection of a novel catalytic RNA: characterization of a sulfur alkylation reaction and interaction with a small peptide"., RNA, vol. 2, pp. 982-994, (1996).

Wedekind, J.E., et al., "Crystal structure of a lead-dependent ribozyme revealing metal binding sites relevant to catalysis"., Nature Structural Biology, vol. 6, No. 3, pp. 261-268, (1999).

Wedekind, J.E., et al., "Crystal structure of the leadzyme at 1.8 Å Resolution: Metal ion binding and the implications for catalytic mechanism and allo site ion regulation"., Biochemistry, vol. 42, No. 32, pp. 9554-9563, (2003).

Wells, R.D., "Unusual DNA structures"., Journal of Biological Chemistry, vol. 263, No. 3, pp. 1095-1098, (1998).

Werstuck, G., et al., "Controlling gene expression in living cells through small molecule-RNA interactions"., Science, vol. 282, pp. 296-298, (1998).

Whaley, S.R., et al., "Selection of peptides with semiconductor binding specificity for directed nanocrystal assembly"., Nature, vol. 405, pp. 665-668, (2000).

Whitesides, G.M., et al., "Self-assembled monolayers and lithography"., Proceedings of the Robert A. Welch Foundation 39th Conference On Chemical Research on Nanophase Chemistry, pp. 109-121, Houston, TX, Oct. 23-24, 1995.

Wiegand, T.W., et al., "High-affinity oligonucleotide ligands to human IgE inhibit binding to Fc epsilon receptor I"., The Journal of Immunology, vol. 157, pp. 221-230, (1996).

Wiegand, T.W., et al., "Selection of RNA amide synthases"., Chemistry & Biology, vol. 4, No. 9, pp. 675-683, (1997).

Williams, K.P., et al., "Bioactive and nuclease-resistant L-DNA ligand of vasopression"., Proc. Natl. Acad. Sci. USA, vol. 94, pp. 11285-11290, (1997).

Williams, K.P., et al., "Selection of novel $Mg^{2+}$-dependent self-cleaving ribozymes" The EMBO Journal, vol. 14, No. 18, pp. 4551-4557, (1995).

Wilson, C., et al., "Functional requirements for specific ligand recognition by a biotin-binding RNA Pseudoknot"., Biochemistry, vol. 37, No. 41, pp. 14410-14419, (1998).

Wilson, C., et al., "In vitro evolution of a self-alkylating ribozyme"., Nature, vol. 374, pp. 777-782, (1995).

Wilson, C., et al., "Isolation of a fluorophore-specific DNA aptamer with weak redox activity"., Chemistry & Biology, vol. 5, No. 11, pp. 609-617, (1998).

Wilson, D.S., et al., "In vitro selection of functional nucleic acids"., Annu. Rev. Biochem. vol. 68, pp. 611-647, (1999).

Winkler, J.D., et al., "Photodynamic Fluorescent Metal Ion Sensors with Parts per Billion Sensitivity"., J. Am. Chem. Soc., vol. 120, No. 13, pp. 3237-3242, (1998).

Wittmann, C., et al., "Microbial and Enzyme sensors for environmental monitoring"., Handbook of Biosensors and Electronic Noses: Medicine, Food, and the Environment, pp. 299-332, (1997).

Xia, P., et al., "Activation of Sphingosine Kinase by Tumor Necrosis Factor-α Inhibits Apoptosis in Human Endothelial Cells"., Journal of Biological Chemistry, vol. 274, No. 48, pp. 34499-34505, (1999).

Yan, H., et al., "DNA-Templated self-assembly of protein arrays and highly conductive nanowires"., Science, vol. 301, pp. 1882-1884, (2003).

Yang, Q., et al., "DNA ligands that bind tightly and selectively to cellobiose"., Proc. Natl. Acad. Sci. USA, vol. 95, pp. 5462-5467, (1998).

Yurke, B., et al., "A DNA-fuelled molecular machine made of DNA"., Nature, vol. 406, pp. 605-608, (2000).

Zhang, B., et al., "Peptide bond formation by in vitro selected ribozymes"., Nature, vol. 390, pp. 96-100, (1997).

Zhang, P., et al., "Design of a molecular beacon DNA probe with two fluorophores"., Angewandte Chemie International Edition, vol. 40, No. 2, pp. 402-405, (2001).

Zillmann, M., et al., "In vitro optimization of truncated stem-loop II variants of the hammerhead ribozyme for cleavage in low concentrations of magnesium under non-turnover conditions"., RNA, vol. 3, pp. 734-747, (1997).

Zimmerman, J.M., et al., "In vivo selection of spectinomycin-binding RNAs"., Nucleic Acids Research, vol. 30, No. 24, pp. 5425-5435, (2002).

Zimmermann, G.R., et al., "Molecular interactions and metal binding in the theophylline-binding core of an RNA aptamer"., RNA, vol. 6, pp. 659-667, (2000).

International Search Report dated Nov. 21, 2005 for corresponding PCT application No. PCT/US2005/001060.

Supplemental International Search Report dated Nov. 21, 2005 for corresponding PCT application No. PCT/US2005/001060.

Liu, J., et al., "Size control, metal substitution, and catalytic application of cryptomelane nanomaterials prepared using cross-linking reagents"., Chem. Mater., vol. 16, No. 2, pp. 276-285, (2004).

Cake, K.M., et al., "Partition of circulating lead between serum and red cells is different for internal and external sources of lead"., American Journal of Industrial Medicine, vol. 29, pp. 440-445, (1996).

Tanner, F.C., et al., "Transfection of human endothelial cells"., Cardiovascular Research, vol. 35, pp. 522-528, (1997).

European Search Report dated Jul. 10, 2006 for PCT application No. PCT/US2003/12576.

Hazarika, P., et al., "Reversible switching of DNA-Gold nanoparticle aggregation"., Angewandte Chemie International Edition, vol. 43, No. 47, pp. 6469-6471, (2004).

International Search Report dated May 29, 2006 for PCT application No. PCT/US2005/037896 (related application).

Liu, J., et al., "Improving fluorescent DNAzyme biosensors by combining Inter- and Intramolecular quenchers"., Analytical Chemistry, vol. 75, No. 23, pp. 6666-6672, (2003).

Liu, J., et al., "Stimuli-responsive disassembly of nanoparticle aggregates for light-up colorimetric sensing"., Journal of the American Chemical Society, vol. 127, No. 36, pp. 12677-12683, (2005).

Abstract of: Iwasaki, K., Mizota, T., Kenkyu Hokoku—Kanagawa-ken Kogyo Shikensho 1991, 62, 57.

Storhoff, J.J., et al., "Facile colorimetric detection of polynucleotides based on gold nanoparticle probes"., Proceedings of the 1998 ERDEC Scientific Conference on Chemical and Biological Defense Research, Nov. 17-20, 1998, Aberdeen Proving Ground, pp. 221-226, (1999).

Yang, Y., et al., "Measurement of lead and magnesium in distilled spirits using inductively coupled plasma optical emission spectrometry viewed from the end"., Analytical Chemistry (Fenxi Huaxue), Chinese Journal of Analytical Chemistry, vol. 25, No. 9, pp. 1114-1117, (1997).

International Search Report dated Aug. 31, 2004 for corresponding PCT application No. PCT/US2004/002946.

International Search Report dated Nov. 17, 2006 for PCT application No. PCT/US2006/001627.

Liu, J., et al., "DNAzyme-directed assembly of gold nanoparticles as colorimetric sensor for a broad range of analytes", pp. 1-3, located at http://ieeenano2003.arc.nasa.gov/THM@.pdf, (2003).

Wang, D.Y., et al., "A general approach for the use of oligonucleotide effectors to regulate the catalysis of RNA-cleaving ribozymes and DNAzymes", Nucleic Acids Research, vol. 30, No. 8, pp. 1735-1742, (2002).

Levy, M., et al., "Exponential growth by cross-catalytic cleavage of deoxyribozymogens",PNAS, vol. 100, No. 11, pp. 6416-6421, (2003).

Beyer, S., et al., "A modular DNA signal translator for the controlled release of a protein by an aptamer", Nucleic Acids Research, vol. 34, No. 5, pp. 1581-1587, (2006).

Frauendorf, C., et al., "Detection of small organic analytes by fluorescing molecular switches", Bioorganic & Medicinal Chemistry, vol. 9, pp. 2521-2524, (2001).

Glynou, K., et al., "Oligonucleotide-functionalized gold nanoparticles as probes in a dry-reagent strip biosensor for DNA analysis by hybridization", Anal. Chem, vol. 75, No. 16, pp. 4155-4160, (2003).

Liu, J., et al., "Optimization of a $Pb^{2+}$-directed gold nanoparticle/ DNAzyme assembly and its application as a colorimetric biosensor for $Pb^{2+}$", Chem. Mater., vol. 16, No. 17, pp. 3231-3238, (2004).

Jones, K.D., et al., "Anniversary Essays, 3. Assay development, Changes in the development of rapid assays since 1995", Medical Devicelink, found at: http://www.devicelink.com/ivdt/archive/05/04/005.html, 3 pages, (2005).

Product Description: Pall Corporation, "Immunochromatographic, lateral flow or strip tests development ideas", found at: http://www.pall.com/34445_4154.asp, 7 pages, (1998).

Liu, J., et al., "Fast colorimetric sensing of adenosine and cocaine based on a general sensor design involving aptamers and nanoparticles", Angew. Chem. Int. Ed., vol. 45, pp. 90-94, (2006).

Liu, J., et al., "A simple and sensitive "dipstick" test in serum based on lateral flow separation of aptamer-linked nanostructures", Angewandte Chemie International Edition, vol. 45, pp. 7955-7959, (2006).

Jiang, P. et al., "Fluorescent detection of zinc in biological systems: recent development on the design of chemosensors and biosensors", Coordination Chemistry Reviews, vol. 248, pp. 205-229, (2004).

Lim, M.H., et al., "Metal-based turn-on fluorescent probes for sensing nitric oxide", Accounts of Chemical Research, vol. 40, No. 1, pp. 41-51, (2007).

Yoon, S. et al., "Screening mercury levels in fish with a selective fluorescent chemosensor", Journal of the American Chemistry Society, vol. 127, pp. 16030-16031, (2005).

Yang, L., et al., "Imaging of the intracellular topography of copper with a fluorescent sensor and by synchrotron x-ray fluorescence microscopy", Proceedings of the National Academy of Science, vol. 102, No. 32, pp. 11179-11184, (2005).

He, Q. et al., "A selective fluorescent sensor for detecting lead in living cells", Journal of the American Chemical Society, vol. 128, pp. 9316-9317, (2006).

Zeng, L. et al., "A selective turn-on fluorescent sensor for imaging copper in living cells", Journal of the American Chemical Society, vol. 128, pp. 10-11, (2006).

Wegner, S.V., et al., "Design of an emission ratiometric biosensor from MerR family proteins: A sensitive and selective sensor for Hg2+", Journal of the American Chemical Society, vol. 129, pp. 3474-3475, (2007).

Nolan, E.M., et al., "Turn-on and ratiometric mercury sensing in water with a red-emitting probe", Journal of the American Chemical Society, vol. 129, pp. 5910-5918, (2007).

Sasaki, D.Y., et al., "Metal-induced dispersion of lipic aggregates: A simple, selective, and sensitive fluorescent metal ion sensor", Angew. Chem. Int. Ed., England, vol. 34, No. 8, pp. 905-907, (1995).

Torrado, A., et al., "Exploiting polypeptide motifs for the design of selective Cu(II) ion chemosensors" Journal of the American Chemical Society, vol. 120, pp. 609-610, (1998).

Grandini, P., et al., "Exploiting the self-assembly strategy for the design of selective CuII ion chemosensors", Angew. Chem. Int. Ed, vol. 38, No. 20, pp. 3061-3064, (1999).

Klein, G. et al., "A fluorescent metal sensor based on macrocyclic chelation", Chem. Comm., pp. 561-562, (2001).

Zheng, Y. et al., "A new fluorescent chemosensor for copper ions based on tripeptide glycyl-histidyl-lysine (GHK)", Organic Letters, vol. 3, No. 21, pp. 3277-3280, (2001).

Boiocchi, M. et al., "A two-channel molecular dosimeter for the optical detection of copper(II)" Chem. Comm, pp. 1812-1813, (2003).

Zheng, Y. et al., "Peptidyl fluorescent chemosensors for the detection of divalent copper", Analytical Chemistry, vol. 75, No. 7, pp. 1706-1712, (2003).

Zheng, Y., et al., "Development of fluorescent film sensors for the detection of divalent copper", Journal of the American Chemical Society, vol. 125, pp. 2680-2686, (2003).

Roy, B.C., et al., "Synthesis of new, pyrene-containing metal-chelating lipids and sensing of cupric ions", Organic Letters, vol. 5, No. 1, pp. 11-14, (2003).

Kaur, S. et al., "Photoactive chemosensors 4: a Cu2+ protein cavity mimicking fluorescent chemosensor for selective Cu2+ recognition", Tetrahedron Letters, vol. 45, pp. 5081-5085, (2004).

Mei, Y. et al., "A selective and sensitive chemosensor for Cu2+ based on 8-hydroxyquinoline", Tetrahedron Letters, vol. 47, pp. 2447-2449, (2006).

Zhang, X-B. et al., "A highly selective fluorescent sensor for Cu2+ based on 2-(2'-hydroxyphenyl) benzoxazole in a poly(vinyl chloride) matrix", Analytica Chimica Acta, vol. 567, pp. 189-195, (2006).

Comba, P. et al., "Synthesis of new phenanthroline-based heteroditopic ligands—highly efficient and selective fluorescence sensors for copper (II) ions", European Journal of Inorganic Chemistry, pp. 4442-4448, (2006).

Kim, S. H. et al., "Hg2+-selective off-on and Cu2+-selective on-off type fluoroionophore based upon cyclam", Organic Letters, vol. 8, No. 3, pp. 371-374, (2006).

White, B. R. et al., "Fluorescent peptide sensor for the selective detection of Cu2+", Talanta, vol. 71, pp. 2015-2020, (2007).

Oter, O. et al., "Spectral characterization of a newly synthesized fluorescent semicarbazone derivative and its usage as a selective fiber optic sensor for copper(II)", Analytica Chimica Acta, vol. 584, pp. 308-314, (2007).

Dujols, V. et al., "A long-wavelength fluorescent chemodosimeter selective for Cu(II) ion in water", Journal of the American Chemical Society, vol. 119, pp. 7386-7387, (1997).

Yang, J-S. et al., "Cu2+-induced blue shift of the pyrene excimer emission: a new signal transduction mode of pyrene probes", Organic Letters, vol. 3, No. 6, pp. 889-892, (2001).

Kaur, S., et al., "Photoactive chemosensors 3: a unique case of fluorescence ehnancement with Cu(II)", Chem. Comm. pp. 2840-2841, (2002).

Wu, Q. et al., "Catalytic signal amplification using a heck reaction. An example in the fluorescence sensing of Cu(II)", Journal of the American Chemical Society, vol. 126, pp. 14682-14683, (2004).

Royzen, M. et al., "Ratiometric displacement approach to Cu(II) sensing by fluorescence", Journal of the American Chemical Society, vol. 127, pp. 1612-1613, (2005).

Xu, Z. et al., "Ratiometric and selective fluorescent sensor for CuII based on internal charge transfer (ICT)", Organic Letters, vol. 7, No. 5, pp. 889-892, (2005).

Wen, Z-C. et al., "A highly selective charge transfer fluoroionophore for Cu2+", Chem. Commun., pp. 106-108, (2006).

Yang, H. et al., "Highly selective ratiometric fluorescent sensor for Cu(II) with two urea groups", Tetrahderon Letters, vol. 47, pp. 2911-2914, (2006).

Martinez, R. et al., "2-aza-1,3-butadiene derivatives featuring an anthracene or pyrene unit: highly selective colorimetric and fluorescent signaling of Cu2+ cation", Organic Letters, vol. 8, No. 15, pp. 3235-3238, (2006).

Navani, N.K. et al., "Nucleic acid aptamers and enzymes as sensors", Current Opinion in Chemical Biology, vol. 10, pp. 272-281, (2006).

Liu, J. et al., "A catalytic beacon sensor for uranium with parts-per-trillion sensitivity and millionfold selectivity", Proceedings of the National Academy of Science, vol. 104, No. 7, pp. 2056-2061, (2007).

Georgopoulos, P.G. et al., "Environmental copper: its dynamics and human exposure issues", Journal of Toxicology and Environmental Health, Part B, vol. 4, pp. 341-394, (2001).

Hertzberg, R.P. et al., "Cleavage of DNA with methidiumpropyl-EDTA-iron(II): reaction conditions and product analyses", Biochemistry, vol. 23, pp. 3934-3945, (1984).

Yazzie, M. et al., "Uranyl acetate causes DNA single strand breaks in vitro in the presence of ascorbate (Vitamin C)", Chem. Res. Toxicol., vol. 16, pp. 524-530, (2003).

Bolletta, F., et al., "A [RuII (bipy)3]-[1,9-diamino-3,7-diazanonane-4,6-dione] two-component system as an efficient on-off luminescent chemosensor for Ni2+ and Cu2+ in water, based on an ET (energy transfer) mechanism", Journal of the Chemical Society, Dalton Transactions, pp. 1381-1385, (1999).

Carmi, N. et al., "Characterization of a DNA-cleaving deoxyribozyme", Bioorganic & Medicinal Chemistry, vol. 9, issue 10, pp. 2589-2600, (2001).

Liu, J. et al., "A DNAzyme catalytic beacon sensor for paramagnetic Cu2+ ions in aqueous solution with high sensitivity and selectivity", Journal of the American Chemical Society, 2 pages, (2007), ASAP Web Release Date: Jul. 24, 2007.

Tanaka, K. et al., "Programmable self-assembly of metal ions inside artificial DNA duplexes", Nature Nanotechnology, vol. 1, pp. 190-194, (2006).

Achenbach, J.C. et al., "DNAzymes: From creation in vitro to application in vivo", Current Pharmaceutical Biotechnology, vol. 5, pp. 321-336, (2004).

Balaji, T. et al., "Optical sensor for the visual detection of mercury using mesoporous silica anchoring porphyrin moiety", The Analyst, vol. 130, pp. 1162-1167, (2005).

Caballero, A. et al., "Highly selective chromogenic and redox or fluorescent sensors of Hg2+ in aqueous environment based on 1,4-disubstituted azines", Journal of the American Chemical Society, vol. 127, pp. 15666-15667, (2005).

Chan, W.H. et al., "Development of a mercury ion-selective optical sensor based on fluorescence quenching of 5,10,15,20-tetraphenylporphyrin", Analytica Chimica Acta, vol. 444, pp. 261-269, (2001).

Chen, P. et al., "A general strategy to convert the merR family proteins into highly sensitive and selective fluorescent biosensors for metal ions", Journal of the American Chemical Society, vol. 126, pp. 728-729, (2004).

Chiuman, W. et al., "Efficient signaling platforms built from a small catalytic DNA and doubly labeled fluorogenic substrates", Nucleic Acids Research, vol. 35, No. 2, pp. 401-405, (2007).

Cruz, R.P.G. et al., "Dinucleotide junction cleavage versatility of 8-17 deoxyribozyme", Chemistry & Biology, vol. 11, pp. 57-67, (2004).

Frasco, M.F. et al., "Mechanisms of cholinesterase inhibition by inorganic mercury", the FEBS Journal, vol. 274, pp. 1849-1861, (2007).

Guo, X. et al., "A highly selective and sensitive fluorescent chemosensor for Hg2+ in neutral buffer aqueous solution", The Journal of the American Chemical Society, vol. 126, pp. 2272-2273, (2004).

Harris, H.H. et al., "The chemical form of mercury in fish", Science, vol. 301, pp. 1203, (2003).

Ha-Thi, M-H. et al., "Highly selective and sensitive phosphane sulfide derivative for the detection of Hg2+ in an organoaqueous medium", Organic Letters, vol. 9, No. 6, pp. 1133-1136, (2007).

Joyce, G.F. et al., "Directed evolution of nucleic acid enzymes", Annual Review Biochem., vol. 73, pp. 791-836, (2004).

Ko, S-K. et al., "In vivo monitoring of mercury ions using a rhodamine-based molecular probe", Journal of the American Chemical Society, vol. 128, pp. 14150-14155, (2006).

Kuswandi, B. et al., "Capillary optode: determination of mercury(II) in aqueous solution", Analytical Letters, vol. 32, No. 9. 4, pp. 649-664, (1999).

Kuswandi, B. et al., "Selective pool optode for mercury ion sensing in aqueous solution", Sensors and Actuators B, vol. 74, pp. 131-137, (2001).

Lee, J-S. et al., "Colorimetric detection of mercuric ion (Hg2+) in aqueous media using DNA-functionalized gold nanoparticles", Angewandte Chemie International Edition, vol. 46, pp. 4093-4096, (2007).

Liu, B. et al., "A selective fluorescent ratiometric chemodosimeter for mercury ion", Chem. Communications, pp. 3156-3158, (2005).

Liu, J. et al., "Fluorescent DNAzyme biosensors for metal ions based on catalytic molecular beacons", Methods in Molecular Biology, vol. 335, pp. 275-288, (2006).

Matsushita, M. et al., "A blue fluorescent antibody-cofactor sensor for mercury", Organic Letters, vol. 7, No. 22, pp. 4943-4946, (2005).

Miyake, Y. et al., "MercuryII-mediated formation of thymine-HgII-thymine base pairs in DNA duplexes", Journal of the American Chemical Society, vol. 128, No. 7, pp. 2172-2173, (2006).

Nolan, E.M. et al., "A "turn-on" fluorescent sensor for the selective detection of mercuric ion in aqueous media", Journal of the American Chemical Society, vol. 125, pp. 14270-14271, (2003).

Ono, A. et al., "highly selective oligonucleotide-based sensor for mercury (II) in aqueous solutions", Angew. Chem. Int. Ed., vol. 43, pp. 4300-4302, (2004).

Ostanta, V., et al., "Self-assembled monolayers of thiol-end-labeled DNA at mercury electrodes", Langmuir, vol. 22, pp. 6481-6484, (2006).

Prodi, L. et al., "An effective fluorescent achemosensor for mercury ions", Journal of the American Chemical Society, vol. 122, No. 28, pp. 6769-6770, (2000).

Silverman, S.K., "Survey and Summary: In vitro selection, characterization, and application of deoxyribozymes that cleave RNA", Nucleic Acids Research, vol. 33, No. 19, pp. 6151-6163, (2005).

Song, K.C. et al., "Fluorogenic Hg2+-selective chemodosimeter derived from 8-hydroxyquinoline", Organic Letters, vol. 8, No. 16, pp. 3413-3416, (2006).

Szurdoki, F. et al., "A combinatorial approach to discover new chelators for optical metal ion sensing", Analytical Chemistry, vol. 72, No. 21, pp. 5250-5257, (2000).

Tanaka, Y. et al., "15N-15N J-coupling across HgII: Direct observation of HgII-mediated T-T base pairs in a DNA duplex" Journal of the American Chemical Society, vol. 129, No. 2, pp. 244-245, (2007).

Jacoby, M. "Mercury Sensor—Analytical Chemistry: Colorimetric method is sensitive and selective", Chemical & Engineering News, pp. 15, May 7, 2007.

Vannela, R. et al., "In vitro selection of Hg (II) and as (V)-dependent RNA-cleaving DNAzymes", Environmental Engineering Science, vol. 24, No. 1, pp. 73-84, (2007).

Vaughan, A.A., et al., "Optical fibre reflectance sensors for the detection of heavy metal ions based on immobilized Br-PADAP", Snesors and Actuators B, vol. 51, pp. 368-376, (1998).

Virta, M. et al., "A luminescence-based mercury biosensor", Analytical Chemistry, vol. 67, No. 3, pp. 667-669, (1995).

Wang, J. et al., "Detecting Hg2+ ions with an ICT fluorescent sensor molecule: Remarkable emission spectra shift and unique selectivity", Journal of Organic Chemistry, vol. 71, pp. 4308-4311, (2006).

Wang, J. et al., "A series of polyamide receptor based PET fluorescent sensor molecules: Positively cooperative Hg2+ ion binding with high sensitivity", Organic Letters, vol. 8, No. 17, pp. 3721-3724, (2006).

Widmann, A. et al., "Mercury detection in seawater using a mercaptoacetic acid modified gold microwire electrode", Electroanalysis, vol. 17, No. 10, pp. 825-831, (2005).

Xiao, Y. et al., "Electrochemical detection of parts-per-billion lead via an electrode-bound DNAzyme assembly", Journal of the American Chemical Society, vol. 129, pp. 262-263, (2007).

Yang, W. et al., "Solid phase extraction and spectrophotometric determination of mercury in tobacco and tobacco additives with 5-(p-aminobenzylidene)-thiothiorhodanine", Journal of the Brazilian Chemical Society, vol. 17, No. 5, pp. 1039-1044, (2006).

Yang, Y-K. et al., "A rhodamine-based fluorescent and colorimetric chemodosimeter for the rapid detection of Hg2+ ions in aqueous media", Journal of the American Chemical Society, vol. 127, pp. 16760-16761, (2005).

Zhang, X-B. et al "An optical fiber chemical sensor for mercury ions based on a porphyrin dimmer", Analytical Chemistry, vol. 74, No. 4, pp. 821-825, (2002).

Zhao, Y. et al., "A "turn-on" fluorescent sensor for selective Hg(II) detection in aqueous media based on metal-induced dye formation", Inorganic Chemistry, vol. 45, No. 25, pp. 10013-10015, (2006).

Zhao, Y. et al., "Tuning the sensitivity of a foldamer-based mercury sensor by its folding energy", Journal of the American Chemical Society, vol. 128, No. 31, pp. 9988-9989, (2006).

Zhao, Y. et al., "Detection of Hg2+ in aqueous solutions with a foldamer-based fluorescent sensor modulated by surgactant micelles", Organic Letters, vol. 8, No. 21, pp. 4715-4717, (2006).

Zuker, M., "Mfold web server for nucleic acid folding and hybridization prediction", Nucleic Acids Research, vol. 31, No. 13, pp. 3406-3415, (2003).

International Search Report dated May 10, 2007 for PCT application No. PCT/US2006/030617.

Liu, J. et al., "Adenosine-dependent assembly of aptazyme-functionalized gold nanoparticles and its application as a colorimetric biosensor", Analytical Chemistry, vol. 76, No. 6, pp. 1627-1632, (2004).

Liu, J. et al., "Smart nanomaterials responsive to multiple chemical stimuli with controllable cooperativity", Advanced Materials, vol. 18, No. 13, pp. 1667-1671, (2006).

Nutiu, R. et al., "Signaling aptamers for monitoring enzymatic activity and for inhibitor screening", Chembiochem—A European Journal of Chemical Biology, vol. 5, No. 8, pp. 1139-1144, (2004).

Nutiu, R. et al., "Structure-switching signaling aptamers: Transducing molecular recognition into fluorescence signaling", Chemistry—A European Journal, vol. 10, No. 8, pp. 1868-1876, (2004).

International Search Report dated Jul. 31, 2007 for PCT application No. PCT/US2007/064055.

Ahern, H., "Biochemical, reagent kits offer scientists good return on investment", The Scientist, vol. 9, No. 15, pp. 20-22, (1995).

Homann, M. et al., "Dissociation of long-chain duplex RNA can occur via strand displacement in vitro: biological implication", Nucleic Acids Research, vol. 24, No. 22, pp. 4395-4400, (1996).

Alivisatos, A.P. et al., "Quantum dots as cellular probes", Annual Review Biomed. Eng, vol. 7, pp. 55-76, (2005).

Dyadyusha, L. et al., "Quenching of CdSe quantum dot emission, a new approach for biosensing", Chemical Communication, pp. 3201-3203, (2005).

Ellington, A.D. et al., "In vitro selection of RNA molecules that bind specific ligands", Nature, vol. 346, pp. 818-822, (1990).

Gerion, D. et al., "Room-temperature single-nucleotide polymorphism and multiallele DNA detection using fluorescent nanocrystals and microarrays", Analytical Chemistry, vol. 75, No. 18, pp. 4766-4772, (2003).

Goldman, E.R. et al., "Multiplexed toxin analysis using four colors of quantum dot fluororeagents", Analytical Chemistry, vol. 76, No. 3, pp. 684-688, (2004).

Gueroui, Z. et al., "Single-molecule measurements of gold-quenched quantum dots", Physical Review Letters, vol. 93, No. 16, pp. 166108/1-166108/4, (2004).

Han, M. et al., "Quantum-dot-tagged microbeads for multiplexed optical coding of biomolecules", Nature Biotechnology, vol. 19, pp. 631-635, (2001).

Hansen, J.A. et al., "Quantum-dot/Aptamer-based ultrasensitive multi-analyte electrochemical biosensor", Journal of the American Chemical Society, vol. 128, No. 7, pp. 2228-2229, (2006).

Hartig, J.S. et al., "Protein-dependent ribozymes report molecular interactions in real time", Nature Biotechnology, vol. 20, pp. 717-722, (2002).

Herman, T. et al., "Adaptive recognition by nucleic acid aptamers", Science, vol. 287, pp. 820-825, (2000).

Kurreck, J., "Antisense technologies Improvement through novel chemical modifications", Eur. J. Biochem, vol. 270, pp. 1628-1644, (2003).

Lee, J.F. et al., "Aptamer database", Nucleic Acids Research, vol. 32, Database Issue, pp. D95-D100, (2004).

Levy, M. et al., "Quantum-dot aptamer beacons for the detection of proteins", ChemBioChem, vol. 6, pp. 2163-2166, (2005).

Liu, J. et al., "Preparation of aptamer-linked gold nanoparticle purple aggregates for colorimetric sensing of analytes", Nature Protocols, vol. 1, No. 1, pp. 246-252, (2006).

Medintz, I.L. et al., "Quantum dot bioconjugates for imaging, labeling and sensing", Nature Materials, vol. 4, pp. 435-446, (2005).

Miduturu, C. V. et al., "Modulation of DNA constraints that control macromolecular folding", Angew. Chem. Int. Ed., vol. 45, pp. 1918-1921, (2006).

Mitchell, G.P. et al., "Programmed assembly of DNA functionalized quantum dots", Journal of the American Chemical Society, vol. 121, No. 35, pp. 8122-8123, (1999).

Nutiu, R. et al., "Structure-switching signaling aptamers: Transducing molecular recognition into fluorescence signaling", Chem. Eur. J., vol. 10, pp. 1868-1876, (2004).

Oh, E. et al., "Inhibition assay of biomolecules based on fluorescence resonance energy transfer (FRET) between quantum dots and gold nanoparticles", Journal of the American Chemical Society, vol. 127, No. 10, pp. 3270-3271, (2005).

Rajendran, M. et al., "In vitro selection of molecular beacons", Nucleic Acids Research, vol. 31, No. 19, pp. 5700-5713, (2003).

Vet, J.A.M. et al., "Multiplex detection of four pathogenic retroviruses using molecular beacons", Proceedings of the National Academy of Science, USA., vol. 96, pp. 6394-6399, (1999).

Wargnier, R., et al., "Energy transfer in aqueous solutions of oppositely charged CdSe/ZnS core/shell quantum dot-nanogold assemblies", Nano Letters, vol. 4, No. 3, pp. 451-457, (2004).

Wilson, R. et al., "Encoded microcarriers for high-throughput multiplexed detection", Angewandte Chemie International Edition, vol. 45, pp. 6104-6117, (2006).

Winkler, W.C. et al., "Regulation of bacterial gene expression by riboswitches", The Annual Review of Microbiology, vol. 59, pp. 487-517, (2005).

Yang, C.J. et al., "Light-switching excimer probes for rapid protein monitoring in complex biological fluids", PNAS, vol. 102, No. 48, pp. 17278-17283, (2005).

Liu, J. et al., "Quantum dot encoding of aptamer-linked nanostructures for one-pot simultaneous detection of multiple analytes", Analytical Chemistry, vol. 79, No. 11, pp. 4120-4125, (2007).

Lu, Y. et al., "Smart nanomaterials inspired by biology: Dynamic assembly of error-free nanomaterials in response to multiple chemical and biological stimuli", Accounts of Chemical Research, vol. 40, No. 5, pp. 315-323, (2007).

Allen, M.J. et al., "Magnetic resonance contrast agents for medical and molecular imaging", Met. Ions Biol. Syst., vol. 42, pp. 1-38, (2004).

Artemov, D. et al., "MR molecular imaging of the Her-2/neu receptor in breast cancer cells using targeted iron oxide nanoparticles", Magnetic Resonance in Medicine, vol. 49, pp. 403-408, (2003).

Buerger, C. et al., "Sequence-specific peptide aptamers, interacting with the intracellular domain of the epidermal growth factor receptor, interfere with stat3 activation and inhibit the growth of tumor cells", The Journal of Biological Chemistry, vol. 278, No. 39, pp. 37610-37621, (2003).

Buerger, C. et al., "Bifunctional recombinant proteins in cancer therapy: cell penetrating peptide aptamers as inhibitors of growth factor signaling", J. Cancer Research Clin. Oncol., vol. 129, pp. 669-675, (2003).

Carr, D.H. et al., "Gadolinium-DTPA as a contrast agent in MRI: initial clinical experience in 20 patients", American Journal of Roentfenol., vol. 143, pp. 215-224, (1984).

Chen, Y. et al., "An autonomous DNA nanomotor powered by a DNA enzyme", Angew. Chem. Int. Ed., vol. 43, pp. 3554-3557, (2004).

Corot, C. et al., "Macrophage imaging in central nervous system and in carotid atherosclerotic plaque using ultrasmall superparamagnetic iron oxide in magnetic resonance imaging", Investigative Radiology, vol. 39, No. 10, pp. 619-625, (2004).

Dodd, C.H. et al., "Normal T-cell response and in vivo magnetic resonance imaging of T cells loaded with HIV transactivator-peptide-derived superparamagnetic nanoparticles", Journal of Immunological Methods, vol. 256, pp. 89-105, (2001).

Drolet, D.W. et al., "An enzyme-linked oligonucleotide assay", Nature Biotechnology, vol. 14, pp. 1021-1025, (1996).

Enochs, W.S. et al., "Improved delineation of human brain tumors on MR images using a long-circulating, superparamagnetic iron oxide agent", Journal of Magnetic Resonance Imaging, vol. 9, pp. 228-232, (1999).

Famulok, M. et al., "Nucleic acid aptamers-from selection in vitro to applications in vivo", Accounts of Chemical research, vol. 33, No. 9, pp. 591-599, (2000).

Fang, X. et al., "Molecular aptamer for real-time oncoprotein platelet-derived growth factor monitoring by fluorescence anisotropy", Analytical Chemistry, vol. 73, No. 23, pp. 5752-5757, (2001).

Frullano, L. et al., "Synthesis and characterization of a doxorubicin-Gd(III) contrast agent conjugate: A new approach toward prodrug-procontrast complexes", Inorganic Chemistry, vol. 45, No. 21, pp. 8489-8491, (2006).

Hamaguchi, N. et al., "Aptamer beacons for the direct detection of proteins", Analytical Biochemistry, vol. 294, pp. 126-131, (2001).

Harisinghani, M.G. et al., "Noninvasive detection of clinically occult lymph-node metastases in prostate cancer", The New England Journal of Medicine, vol. 348, No. 25, pp. 2491-2499, (2003).

Hermann, T. et al., "Adaptive recognition by nucleic acid aptamers", Science, vol. 287, pp. 820-825, (2000).

Hoppe-Seyler, F. et al., "Peptide aptamers: Specific inhibitors of protein function", Current Molecular Medicine, vol. 4, pp. 529-538, (2004).

Huang, C-C. et al., "Aptamer-modified gold nanoparticles for colorimetric determination of platelet-derived growth factors and their receptors", Analytical Chemistry, vol. 77, No. 17, pp. 5735-5741, (2005).

Josephson, L. et al., "High-efficiency intracellular magnetic labeling with novel superparamagnetic-tat peptide conjugates", Bioconjugate Chem., vol. 10, No. 2, pp. 186-191, (1999).

Josephson, L. et al., "The effects of iron oxides on proton relaxivity", Magnetic Resonance Imaging, vol. 6, pp. 647-653, (1988).

Josephson, L. et al., "Magnetic nanosensors for the detection of oligonucleotide sequences", Angew, Chem. Int. Ed., vol. 40, No. 17, pp. 3204-3206, (2001).

Kabalka, G. et al., "Gadolinium-labeled liposomes: Targeted MR contrast agents for the liver and spleen", Radiology, vol. 163, pp. 255-258, (1987).

Kooi, M.E. et al., "Accumulation of ultrasmall superparamagnetic particles of iron oxide in human atherosclerotic plaques can be detected by in vivo magnetic resonance imaging", Circulation, vol. 107, pp. 2453-2458, (2003).

Kresse, M. et al., "Targeting of ultrasmall superparamagnetic iron oxide (USPIO) particles to tumor cells in vivo by using transferring receptor pathways", Magn. Reson. Med., vol. 40, pp. 236-242, (1998).

Lee, J. et al., "A steroid-conjugated contrast agent for magnetic resonance imaging of cell signaling", Journal of American Chemical Society, vol. 127, No. 38, pp. 13164-13166, (2005).

Lewin, M. et al., "Tat peptide-derivatized magnetic nanoparticles allow in vivo tracking and recovery of progenitor cells", Nature Biotechnology, vol. 18, pp. 410-414, (2000).

Li, J.J. et al., "Molecular aptamer beacons for real-time protein recognition", Biochemical and Biophysical Research Communications, vol. 292, No. 1, pp. 31-40, (2002).

Li, W-H. et al., "A calcium-sensitive magnetic resonance imaging contrast agent", Journal of the American Chemical Society, vol. 121, No. 6, pp. 1413-1414, (1999).

Lin, C.H. et al., "Structural basis of DNA folding and recognition in an AMP-DNA aptamer complex: distinct architectures but common recognition motifs for DNA and RNA aptamers complexed to AMP", Chemistry and Biology, vol. 4, pp. 817-832, (1997).

Liss, M. et al., "An aptamer-based quartz crystal protein biosensor", Analytical Chemistry, vol. 74, No. 17, pp. 4488-4495, (2002).

Liu, Y. et al., "Aptamer-directed self-assembly of protein arrays on a DNA nanostructure", Angew. Chem. Int. Ed., vol. 44, pp. 4333-4338, (2005).

Macaya, R.F., et al., "Thrombin-binding DNA aptamer forms a unimolecular quadruplex structure in solution", Proceedings of the National Academy of Science USA, vol. 90, pp. 3745-3749, (1993).

Nagel-Wolfrum, K. et al., "The interaction of specific peptide aptamers with the DNA binding domain and the dimerization domain of the transcription factor stat3-inhibits transactivation and induces apoptosis in tumor cells", Molecular Cancer Research, vol. 2, pp. 170-182, (2004).

Nitin, N. et al., "Functionalization and pepride-based delivery of magnetic nanoparticles as an intracellular MRI contrast agent", J. Biol. Inorg. Chem., vol. 9, pp. 706-712, (2004).

Nutiu, R. et al., "Engineering DNA aptamers and DNA enzymes with fluorescence-signaling properties", Pure Appl. Chem., vol. 76, Nos. 7-8, pp. 1547-1561, (2004).

Padmanabhan, K. et al., "The structure of a-thrombin inhibited by a 15-mer single-stranded DNA aptamer", The Journal of Biological Chemistry, vol. 268, No. 24, pp. 17651-17654, (1993).

Pavlov, V. et al., "Aptamer-functionalized au nanoparticles for the amplified optical detection of thrombin", The Journal of the American Chemical Society, vol. 126, No. 38, pp. 11768-11769, (2004).

Pendergrast, P.S. et al., "Nucleic acid aptamers for target validation and therapeutic applications", Journal of Biomolecular Techniques, vol. 16, issue 3, pp. 224-234, (2005).

Perez, J.M. et al., "Use of magnetic nanoparticles as nanosensors to probe for molecular interactions", ChemBioChem, vol. 5, pp. 261-264, (2004).

Perez, J.M. et al., "Viral-induced self-assembly of magnetic nanoparticles allows the detection of viral particles in biological media", Journal of the American Chemical Society, vol. 125, No. 34, pp. 10192-10193, (2003).

Radi, A-E. et al., "Reagentless, reusable, ultrasensitive electrochemical molecular beacon aptasensor", Journal of the American Chemical Society, vol. 128, No. 1, pp. 117-124, (2006).

Saeed, M. et al., "Occlusive and reperfused myocardial infarcts: differentiation with Mn-DPDP-enhanced MR imaging", Radiology, vol. 172, pp. 59-64, (1989).

Shen, T. et al., "Monocrystalline iron oxide nanocompounds (MION): Physicochemical properties", Magn. Reson. Med., vol. 29, pp. 599-604, (1993).

Soriaga, M.P. et al., "Determination of the orientation of adsorbed molecules at solid-liquid interfaces by thin-layer electrochemistry: Aromatic compounds at platinum electrodes", Journal of the American Chemical Society, vol. 104, pp. 2735-2742, (1982).

Soriaga, M.P. et al., "Determination of the orientation of aromatic molecules adsorbed on platinum electrodes: The influence of iodide a surface-active anion", Journal of the American Chemical Society, vol. 104, pp. 2742-2747, (1982).

Soriaga, M.P. et al., "Determination of the orientation of aromatic molecules adsorbed on platinum electrodes: The effect of solute concentration", Journal of the American Chemical Society, vol. 104, pp. 3937-3945, (1982).

Sosnovik, D.E. et al., "Emerging concepts in molecular MRI", Current Opinion in Biotechnology, vol. 18, pp. 4-10, (2007).

Taboada, E. et al., "Relaxometric and magnetic characterization of ultrasmall iron oxide nanoparticles with high magnetization. Evaluation as potential T1 magnetic resonance imaging contrast agents for molecular imaging", Langmuir, vol. 23, No. 8, pp. 4583-4588, (2007).

Tasset, D.M. et al., "Oligonucleotide inhibitors of human thrombin that bind distinct epitopes", J. Mol. Biol., vol. 272, pp. 688-698, (1997).

Tian, Y. et al., "DNAzyme amplification of molecular beacon signal", Talanta, vol. 67, pp. 532-537, (2005).

Tompkins, H.G. et al., "The study of the gas-solid interaction of acetic acid with a cuprous oxide surface using reflection-absorption spectroscopy", Journal of colloid and interface science, vol. 49, No. 3, pp. 410-421, (1974).

Tsourkas, A. et al., "Magnetic relaxation switch immunosensors detect enantiomeric impurities", Angew. Chem. Int. Ed., vol. 43, pp. 2395-2399, (2004).

Wang, S. et al., "Core/shell quantum dots with high relaxivity and photoluminescence for multimodality imaging", Journal of the American Chemical Society, vol. 129, No. 13, pp. 3848-3856, (2007).

Weissleder, R. et al., "MR imaging of splenic metastases: Ferrite-enhanced detection in rats", American Journal Roentgenol., vol. 149, pp. 723-726, (1987).

Xiao, Y. et al., "Label-free electronic detection of thrombin in blood serum by using an aptamer-based sensor", Angew. Chem. Int. Ed., vol. 44, pp. 5456-5459, (2005).

Xiao, Y. et al., "A reagentless signal-on architecture for electronic, aptamer-based sensors via target-induced strand displacement", Journal of the American Chemical Society, vol. 127, No. 51, pp. 17990-17991, (2005).

Xu, D. et al., "Label-free electrochemical detection for aptamer-based array electrodes", Analytical Chemistry, vol. 77, No. 16, pp. 6218-6224, (2005).

Yamamoto, R. et al., "Molecular beacon aptamer fluoresces in the presence of Tat protein of HIV-1", Genes to Cells, vol. 5, pp. 389-396, (2000).

Zhao, M. et al., "Magnetic sensors for protease assays", Angew. Chem. Int. Ed., vol. 42, No. 12, pp. 1375-1378, (2003).

Zhao, M. et al., "Differential conjugation of tat peptide to superparamagnetic nanoparticles and its effect on cellular uptake", Bioconjugate Chem., vol. 13, pp. 840-844, (2002).

Liu, J. et al., "Colorimetric Cu2+ detection with a ligation DNAzyme and nanoparticles", Chemical Communications, Advance Articles, DOI: 10.1039/b712421j, 6 pages, Oct. 24, 2007.

Liu, J. et al., "Non-Base pairing DNA provides a new dimension for controlling aptamer-linked nanoparticles and sensors", Journal of the American Chemical Society, vol. 129, No. 27, pp. 8634-8643, (2007).

Liu, J. et al., "Supporting Information for Colorimetric Cu2+ detection with a ligation DNAzyme and nanoparticles", Chemical Communications, Advance Articles, 4 pages, Oct. 24, 2007.

Stratagene Catalog, "Gene Characterization Kits", 2 pages, (1988).

* cited by examiner

HEAD-TO-TAIL

TAIL-TO-TAIL

```
                      SEQUENCE LISTING

<160> NUMBER OF SEQ ID NOS: 16

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
catctcttct ccgagccggt cgaaatagtg agt                                 33

<210> SEQ ID NO 2
<211> LENGTH: 20
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: Any single ribonucleotide

<400> SEQUENCE: 2
actcactatn ggaagagatg                                                20

<210> SEQ ID NO 3
<211> LENGTH: 4
<212> TYPE: DNA
<213> ORGANISM: Artificial Sequence
<220> FEATURE:
<223> OTHER INFORMATION: Description of Artificial Sequence: Synthetic
      nucleotide variable region

<400> SEQUENCE: 3 tatt                                                                  4

<210> SEQ ID NO 4
<211> LENGTH: 19
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
```

```
       oligonucleotide
<220> FEATURE:
<221> NAME/KEY: modified_base
<222> LOCATION: (11)
<223> OTHER INFORMATION: Any single ribonucleotide

<400> SEQUENCE: 4
gactcactat nggaagaga                                                   19

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tctcttctcc gagccggtcg aaatattgga ggaagctc                               38

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gagctggagg aaaaagtgag tc                                               22

<210> SEQ ID NO 7
<211> LENGTH: 43
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)
<223> OTHER INFORMATION: Any single ribonucleotide

<400> SEQUENCE: 7
actcatctgt gagactcact atnggaagag atgtcaactc gtg                        43

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tctcttctcc gagccggtcg aaatattgga ggaagctc                               38

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
```

```
gagctggagg aaaaagtgag tc                                              22
```

<210> SEQ ID NO 10
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)
<223> OTHER INFORMATION: Any single ribonucleotide

<400> SEQUENCE: 10

```
actcactata nggaagagat g                                               21
```

<210> SEQ ID NO 11
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

```
cacgagttga ca                                                         12
```

<210> SEQ ID NO 12
<211> LENGTH: 45
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)
<223> OTHER INFORMATION: Any single ribonucleotide

<400> SEQUENCE: 12

```
tgtcaactcg tgactcacta tnaggaagag atgtgtcaac tcgtg                     45
```

<210> SEQ ID NO 13
<211> LENGTH: 44
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)
<223> OTHER INFORMATION: Any single ribonucleotide

<400> SEQUENCE: 13

```
actcatctgt gagactcact atanggaaga gatgtcaact cgtg                      44
```

<210> SEQ ID NO 14
<211> LENGTH: 50

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cacgagttga catctcttct ccgagccggt cgaaatattg gaggaagctc                50

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gagctggagg aaaaagtgag tctcacagat gagt                                 34

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tctcttccat tttttttaat agtgagtc                                        28
```

BIOSENSORS BASED ON DIRECTED ASSEMBLY OF PARTICLES

FEDERALLY SPONSORED RESEARCH OR DEVELOPMENT

The subject matter of this application may in part have been funded by the Department of Energy (DEFG02-01ER63179) and the National Science Foundation (DMR-0117792). The government may have certain rights in this invention.

BACKGROUND

Besides proteins, nucleic acids have also been found to have catalytic activities in recent years. The catalytic active nucleic acids can be catalytic DNA/RNA, also known as DNAzymes/RNAzymes, deoxyribozymes/ribozymes, and DNA enzymes/RNA enzymes. Catalytic active nucleic acids can also contain modified nucleic acids. The catalytic activities of nucleic acid-based enzymes always depend on the presence of certain cofactors, for example, metal ions. Therefore, nucleic acid enzyme-based biosensors for these cofactors (e.g. biosensors for metal ions) can be designed based on the activities of the corresponding nucleic acid enzymes. On the other hand, nucleic acids may be selected to bind to a wide range of analytes with high affinity and specificities. These binding nucleic acids are known as aptamers.

Aptamers are nucleic acids (such as DNA or RNA) that recognize targets with high affinity and specificity (Ellington and Szostak 1990, Jayasena 1999). Aptazymes (also called allosteric DNA/RNAzymes or allosteric (deoxy) ribozymes) are DNA/RNAzymes regulated by an effector (the target molecule). They typically contain an aptamer domain that recognizes an effector and a catalytic domain (Hesselberth et al. 2000, Soukup and Breaker 2000, Tang and Breaker 1997). The effector can either decrease or increase the catalytic activity of the aptazyme through specific interactions between the aptamer domain and the catalytic domain. Therefore, the activity of the aptazyme can be used to monitor the presence and quantity of the effector. This strategy has been used to select and design aptazyme sensors for diagnostic and sensing purposes (Breaker 2002, Robertson and Ellington 1999, Seetharaman et al. 2001). DNAzymes and DNA aptazymes are the most attractive candidate for sensor development because DNA is much less expensive to synthesize and more stable than RNA. In addition, general strategies to design DNA aptazymes, by introducing aptamer motifs close to the catalytic core of DNAzymes, are available (Wang et al. 2002). High cleavage activity requires the presence of effector molecules that upon binding to the aptamer motif, can allosterically modulate the activity of the catalytic core part of the aptazyme.

In vitro selection methods can be used to obtain aptamers for a wide range of target molecules with exceptionally high affinity, having dissociation constants as high as in the picomolar range (Brody and Gold 2000, Jayasena 1999, Wilson and Szostak 1999). For example, aptamers have been developed to recognize metal ions such as Zn(II) (Ciesiolka et al. 1995) and Ni(II) (Hofmann et al. 1997); nucleotides such as adenosine triphosphate (ATP) (Huizenga and Szostak 1995); and guanine (Kiga et al. 1998); co-factors such as NAD (Kiga et al. 1998) and flavin (Lauhon and Szostak 1995); antibiotics such as viomycin (Wallis et al. 1997) and streptomycin (Wallace and Schroeder 1998); proteins such as HIV reverse transcriptase (Chaloin et al. 2002) and hepatitis C virus RNA-dependent RNA polymerase (Biroccio et al. 2002); toxins such as cholera whole toxin and staphylococcal enterotoxin B (Bruno and Kiel 2002); and bacterial spores such as the anthrax (Bruno and Kiel 1999). Compared to antibodies, DNA/RNA based aptamers are easier to obtain and less expensive to produce because they are obtained in vitro in short time periods (days vs. months) and with limited cost. In addition, DNA/RNA aptamers can be denatured and renatured many times without losing their biorecognition ability. These unique properties make aptamers an ideal platform for designing highly sensitive and selective biosensors (Hesselberth et al. 2000).

To assay DNA/RNAzyme or aptazyme activity, detectable labels are used. However, many of these suffer from significant drawbacks. Radioisotopes incur safety and disposal concerns, whereas fluorophores may undergo photo-bleaching and may also inhibit the biological activity trying to be assayed; organic dyes, such as that used in a cocaine-detecting aptamer system (Stojanovic and Landry, 2002) require high concentrations for visual detection and are matched to a specific aptamer only after costly trial and error.

Metallic particles overcome all of these difficulties. They can be used in small (nanomolar) amounts as detection agents with aptamers without any of the disadvantages of organic dyes. In sensors based on aptamers using metallic particles for color detection, the cleavage of a nucleic acid substrate by the aptazyme (upon binding of an effector) may be detected by color changes.

Typically, a DNA/RNAzyme- or aptazyme-based sensor has three parts:

(1) a nucleic acid enzyme (in the following description, nucleic acid enzymes will be referred to DNA/RNAzymes and aptazymes) and a co-factor, such as a metal ion that catalyzes substrate cleavage;

(2) a nucleic acid substrate for the nucleic acid enzyme, wherein interior portions of the substrate sequence is complementary to portions of the enzyme sequence; and (3) particles attached to polynucleotides that are complementary to the 3'- and 5'-termini of the substrate.

To detect the target cofactor or effector, the complementary portions of the polynucleotides (the polynucleotides attached to the particles complementary to the 3'- and 5'-termini of the substrate strand, and the 5'- and 3'-termini of the nucleic acid enzyme complementary to interior substrate strand sequences) are annealed in the presence of a sample suspected of containing the targeted cofactor or effector. If the cofactor or effector is absent, the aptazyme is either inactive or shows substantially reduced activity, resulting in no or little substrate cleavage and thus aggregation of the particles. If the cofactor or effector is present, the enzyme becomes active and cleaves the substrate, preventing aggregate formation because the link between the particles is broken by enzymatic cleavage. Table 1 exemplifies such a system.

| Cleavage | Aggregation | Color* |
| --- | --- | --- |
| YES (the target effector is present) | DISPERSED | RED |
| NO | NON-DISPERSED | BLUE |

*When gold particles are used for detection.

In the case of gold particles, the aggregated state displays a blue color, while the dispersed state (or the non-aggregate state) is red in color. The presence of the target analyte as a cofactor or effector can be detected based on the appearance of the color of the sensor system.

Since the degree of cleavage is reflected in the degree of color change, the target cofactor or effector concentration can be quantified. For example, simple spectrometry may be used for sensitive detection. Not only can color change be used for detection and quantifying, other results of the cleavage may be employed, such as precipitation. By replacing the aptamer domain with aptamers recognizing pre-selected effectors, calorimetric sensors for any desired effector can be easily made and used.

Based on previous work, a colorimetric biosensor for Pb(II) based on the DNAzyme-directed assembled of gold nanoparticles and a calorimetric biosensor for adenosine based on the aptazyme-directed assembled of gold nanoparticles have been designed (see, for example, U.S. application Ser. Nos. 09/605,558; 10/144,094; 10/144,679; and 10/384, 497). Though highly sensitive and selective, this type of analytical sensor requires heating to above 50° C. for several minutes and cooling slowly to room temperature in 2 hours for detection.

SUMMARY

In a first aspect, the invention is a sensor system for detecting an effector or cofactor, comprising (a) a nucleic acid enzyme, comprising a cofactor binding site and optionally an effector binding site; (b) substrates for the nucleic acid enzyme, comprising first polynucleotides; (c) a first set of particles comprising second polynucleotides, where the polynucleotides are attached to the particles at the 3' terminus; and (d) a second set of particles comprising third polynucleotides, where the polynucleotides are attached to the particles at the 5' terminus. The first polynucleotides comprise or are at least partially complementary to the second polynucleotides, and the first polynucleotides comprise or are at least partially complementary to the third polynucleotides.

In a second aspect, the present invention is sensor system for detecting an effector or cofactor, comprising (a) a nucleic acid enzyme, comprising a cofactor binding site and optionally an effector binding site; (b) substrates for the nucleic acid enzyme, comprising first polynucleotides; (c) a first set of particles comprising second polynucleotides; and (d) a second set of particles comprising third polynucleotides. The first polynucleotides comprise or are at least partially complementary to the second polynucleotides, and the first polynucleotides comprise or are at least partially complementary to the third polynucleotides. The second set of particles have a diameter of at least 20 nm.

In a third aspect, the present invention is a method of detecting an effector or cofactor in a sample, comprising mixing together at least (a) a nucleic acid enzyme, comprising a cofactor binding site and optionally an effector binding site; (b) substrates for the nucleic acid enzyme, comprising first polynucleotides; (c) a first set of particles comprising second polynucleotides; (d) a second set of particles comprising third polynucleotides; and (e) the sample; to form a mixture. The first polynucleotides comprise or are at least partially complementary to the second polynucleotides, and the first polynucleotides comprise or are at least partially complementary to the third polynucleotides. The mixture produces a color change indicating the presence of the effect or cofactor in the sample within 10 minutes of forming the mixture, without heating.

DETAILED DESCRIPTION

The present invention avoids the heating required for previous DNAzyme- and aptazyme-metal particle sensor systems, allowing these sensors to be used not only in laboratories, but by consumers in their homes, or by technicians in the field. The invention uses the following discoveries that influence the performance of particle-based colorimetric biosensors: (1) altering the alignment of the particles from head-to-tail to tail-to-tail; (2) using larger particles; and (3) controlling ionic strength, aptamer concentration and pH.

Figure 3A:
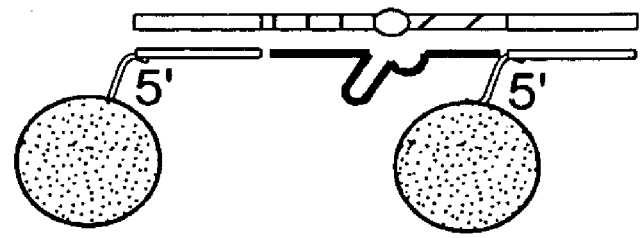
FIG. 3. The two alignments of DNA linked gold particles. (A) "head-to-tail" aligned particles, where only one kind of thiol-modified DNA is needed. (B) "tail-to-tail" aligned particles FIG. 4. The effect of particle alignment and particle size on the rate of color change.
Figure 3B:
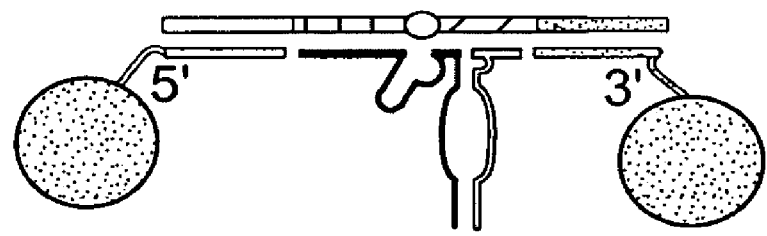
Figure 5:
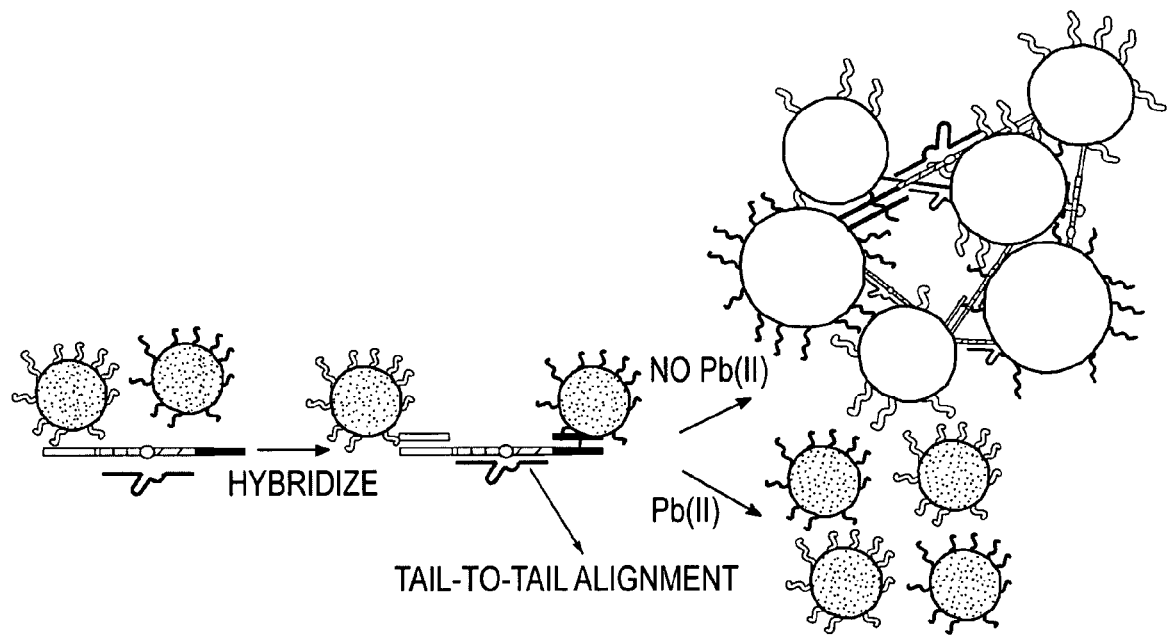
FIG. 5. A $Pb^{2+}$ calorimetric biosensor where the diameter of particles is ~35 nm and the particles are aligned in the "tail-to-tail" manner.

The aggregation of particles is influenced by their alignment with respect to each other. Particles may be aligned in two ways, "head-to-tail" or "tail-to-tail" (FIG. 3). In an earlier DNAzyme-based $Pb^{2+}$ sensor, for example, the particles are aligned in the "head-to-tail" fashion. If the particles are aligned in the "head-to-tail" manner, only one kind of thiol-modified DNA is needed to attach the DNA to the particle. In this configuration, it is difficult for the particles to aggregate, possibly due to steric effects. Heating and cooling is thus necessary to promote the assembly of particles. However, it has now been discovered that when a "tail-to-tail" alignment is used, the particles can aggregate at ambient temperature (FIG. 5). For "tail-to-tail" aligned particles, both 3'- and 5'-thiol-modified polynucleotides are needed.

The color of particle aggregates is mainly governed by the size of the aggregates. Thus, the rate of aggregation being equal, the rate of color change increases using larger particles. As illustrated in the examples below, when a mixture of 13 and 35 nm diameter particles is used, the rate of color change is faster than with particles of 13 nm diameter only. The rate of color change further increases if only particles of 35 nm diameter are used.

The ionic strength of the solution influences the performance of the system as well. Higher salt concentration favors aggregation, likely due to the salt reducing the electrostatic repulsion between the negatively charged polynucleotide strands. Though only the substrate strand is needed to link two particles, in the absence of the enzyme strand the substrate is too "floppy" to assemble particles. Thus the concentration of the enzyme is an important parameter.

pH also influences aggregation. The influence of pH is likely due to protonation of the bases of the polynucleotide, which affects base pairing and thus the rate of aggregation.

DEFINITIONS

A "co-factor" is an ion or molecule involved in the catalytic process of nucleic acid enzyme-catalyzed reactions and is required for catalytic activity.

An "effector" is a molecule that, when bound to an enzyme having an effector binding site, can enhance or inhibit enzyme catalysis. An "effector binding site" may be "specific," that is, binding only one effector molecule in the presence of other effector molecules. An example of effector binding site specificity is when only an adenosine molecule binds in the presence of other similar molecules, such as cytidine, gaunosine and uridine. Alternatively, an effector binding site may be "partially" specific (binding only a class of molecules), or "non-specific" (having molecular promiscuity). Examples of effectors include environmental pollutants, such as nitrogen fertilizers, pesticides, dioxin, phenols, or 2,4-dichlorophenoxyacetic acid; heavy metal ions, such as Pb(II), Hg(II), As(III), $UO_2$(II), Fe(III), Zn(II), Cu(II), or Co(II); biological molecules, such as glucose, insulin, hCG-hormone, HIV or HIV proteins; chemical and biological terrorism agents, such as anthrax, small pox, or nerve gases; explosives, such as TNT or DNT; drugs, such as cocaine or antibiotics.

A "nucleic acid enzyme" is an enzyme that principally contains nucleic acids, such as ribozymes (RNAzymes), deoxyribozymes (DNAzymes), and aptazymes. Nucleic acids may be natural, unnatural or modified nucleic acids. Peptide nucleic acids (PNAs) are also included. A nucleic acid enzyme requires a "co-factor" for efficient substrate cleavage and/or specific effector binding. Common co-factors include Mg(II), Ca(II), Zn(II), Mn(II), Co(II) and Pb(II).

"Polynucleotide" refers to a nucleic acid sequence having at least two or more nucleotides. Polynucleotides may contain naturally-occurring nucleotides and synthetic nucleotides. PNA molecules are also embraced by this term.

"Sensitivity" refers to the smallest increase of a cofactor or effector concentration that can be detected by the sensor.

"Detection limit" refers to the limits of detection of an analytical device. In the context of the DNAzyme- and aptazyme-based sensors of the present invention, detection limit refers to the lowest concentration of a cofactor or effector that the sensor can differentiate from the background.

"Base-pairing" refers to the ability of a polynucleotide to form at least one hydrogen bond with a nucleotide under low stringency conditions. The nucleotide may be part of a second polynucleotide or to a nucleotide found within the first polynucleotide. A polynucleotide is partially complementary to a second polynucleotide when the first polynucleotide is capable of forming at least one hydrogen bond with the second polynucleotide. To be partially complementary, a polynucleotide may have regions wherein base pairs may not form surrounded by those regions that do, forming loops, stem-loops, and other secondary structures.

"Aptamer" refers a polynucleotide which contains an effector binding cite. An "effector binding site" may be "specific," that is, binding only one effector molecule in the presence of other effector molecules. An example of effector binding site specificity is when only an adenosine molecule binds in the presence of many other similar molecules, such as cytidine, gaunosine and uridine. Alternatively, an effector binding site may be "partially" specific (binding only a class of molecules), or "non-specific" (having molecular promiscuity).

"Aptazyme" refers to a nucleic acid enzyme that includes an aptamer region which binds an effector. The binding of the effector can enhance or inhibit catalysis.

A Nucleic Acid Enzyme Having an Effector (or Effectors) Binding Site

A number of nucleic acid enzymes have been discovered or developed, having diverse catalytic activities (Tables 1 and 2). For catalytic function, the enzymes usually depend on one or more co-factors. In vitro selection may be used to "enhance" selectivity and sensitivity for a particular ion. Nucleic acid enzymes that catalyze molecular association (ligation, phosphorylation, and amide bond formation) or dissociation (cleavage or transfer) are particularly useful in the present invention.

A nucleic acid enzyme that catalyzes the cleavage of a nucleic acid in the presence of an effector is used. The nucleic acid enzyme may be RNA (ribozyme), DNA (deoxyribozyme), a DNA/RNA hybrid enzyme, or a peptide nucleic acid (PNA) enzyme. PNAs comprise a polyamide backbone and nucleoside bases (available from, e.g., Biosearch, Inc. (Bedford, Mass.)). Ribozymes that may be used include group I and group II introns, the RNA component of the bacterial ribonuclease P, hammerhead, hairpin, hepatitis delta virus and Neurospora VS ribozymes. Also included are in vitro selected ribozymes, such as those previously isolated (Tang and Breaker 2000). Ribozymes tend to be less stable than deoxyribozymes; thus deoxyribozymes are preferred. Deoxyribozymes with extended chemical functionality are also desirable (Santoro et al., 2000).

TABLE 1

Reactions catalyzed by ribozymes that were isolated from in vitro selection experiments.

| Reaction | $k_{cat}$ (min$^{-1}$) | $K_m$ (µM) | $k_{cat}/k_{uncat}$[a] | Reference |
|---|---|---|---|---|
| Phosphoester centers | | | | |
| Cleavage | 0.1 | 0.03 | $10^5$ | (Vaish et al. 1998) |
| Transfer | 0.3 | 0.02 | $10^{13}$ | (Tsang and Joyce 1996) |
| Ligation | 100 | 9 | $10^9$ | (Ekland et al. 1995) |
| Phosphorylation | 0.3 | 40 | $>10^5$ | (Lorsch and Szostak 1994) |

TABLE 1-continued

Reactions catalyzed by ribozymes that were isolated from in vitro selection experiments.

| Reaction | $k_{cat}$ (min$^{-1}$) | $K_m$ (μM) | $k_{cat}/k_{uncat}$[a] | Reference |
|---|---|---|---|---|
| Mononucleotide polymerization | 0.3 | 5000 | >10$^7$ | (Ekland and Bartel 1996) |
| Carbon centers | | | | |
| Aminoacylation | 1 | 9000 | 10$^6$ | (Illangasekare and Yarus 1997) |
| Aminoacyl ester hydrolysis | 0.02 | 0.5 | 10 | (Piccirilli et al. 1992) |
| Aminoacyl transfer | 0.2 | 0.05 | 10$^3$ | (Lohse and Szostak 1996) |
| N-alkylation | 0.6 | 1000 | 10$^7$ | (Wilson and Szostak 1995) |
| S-alkylation | 4 × 10$^{-3}$ | 370 | 10$^3$ | (Wecker et al. 1996) |
| Amide bond cleavage | 1 × 10$^{-5}$ | | 10$^2$ | (Dai et al. 1995) |
| Amide bond formation | 0.04 | 2 | 10$^5$ | (Wiegand et al. 1997) |
| Peptide bond formation | 0.05 | 200 | 10$^6$ | (Zhang and Cech 1997) |
| Diels-Alder cycloaddition | >0.1 | >500 | 10$^3$ | (Tarasow et al. 1997) |
| Others | | | | |
| Biphenyl isomerization | 3 × 10$^{-5}$ | 500 | 10$^2$ | (Prudent et al. 1994) |
| Porphyrin metallation | 0.9 | 10 | 10$^3$ | (Conn et al. 1996) |

[a]Reactions catalyzed by ribozymes that were isolated from in vitro selection experiments. $k_{cat}/k_{uncat}$ is the rate enhancement over uncatalyzed reaction.

TABLE 2

Deoxyribozymes isolated through in vitro selection.

| Reaction | C factor | $k_{max}$ (min$^{-1}$)[b] | $k_{cat}/k_{uncat}$ | Reference |
|---|---|---|---|---|
| RNA transesterification | Pb$^{2+}$ | 1 | 10$^5$ | (Breaker and Joyce 1994) |
| | Mg$^{2+}$ | 0.01 | 10$^5$ | (Breaker et al. 1995) |
| | Ca$^{2+}$ | 0.08 | 10$^5$ | (Faulhammer and Famulok 1997) |
| | Mg$^{2+}$ | 10 | >10$^5$ | (Santoro and Joyce 1997) |
| | None | 0.01 | 10$^8$ | (Geyer and Sen 1997) |
| | L-histidine | 0.2 | 10$^6$ | (Roth and Breaker 1998) |
| | Zn$^{2+}$ | ~40 | >10$^5$ | (Li et al. 2000) |
| DNA cleavage | Cu$^{2+}$ | 0.2 | >10$^6$ | (Carmi et at. 1996) |
| DNA ligation | Cu$^{2+}$ or Zn$^{2+}$ | 0.07 | 10$^5$ | (Cuenoud and Szostak 1995) |
| DNA phosphorylation | Ca$^{2+}$ | 0.01 | 10$^9$ | (Li and Breaker 1999) |
| 5',5'-pyrophosphate formation | Cu$^{2+}$ | 5 × 10$^{-3}$ | >10$^{10}$ | (Li et at. 2000) |
| Porphyrin metalation | None | 1.3 | 10$^3$ | (Li and Sen 1996) |

[b]$k_{max}$ is the maximal rate constant obtained under optimized conditions.

Methods of producing ribozymes and deoxyribozymes include chemical oligonucleotide synthesis, polymerase chain reaction (PCR), DNA cloning and replication. Preferably the nucleic acid enzymes are DNA/RNA hybrids and PNAs. Nucleotides containing modified bases, phosphates, or sugars may also be used; in some instances, these modified nucleotides may be advantageous for stability or confer effector specificity. Examples of modified bases include inosine, nebularine, 2-aminopurine riboside, N$^7$-deazaadenosine, and O$^6$-methylguanosine (Earnshaw and Gait 1998). Modified sugars and phosphates include 2'-deoxynucleoside, abasic, propyl, phosphorothioate, and 2'-O-allyl nucleoside (Earnshaw and Gait 1998).

Figure 1A:
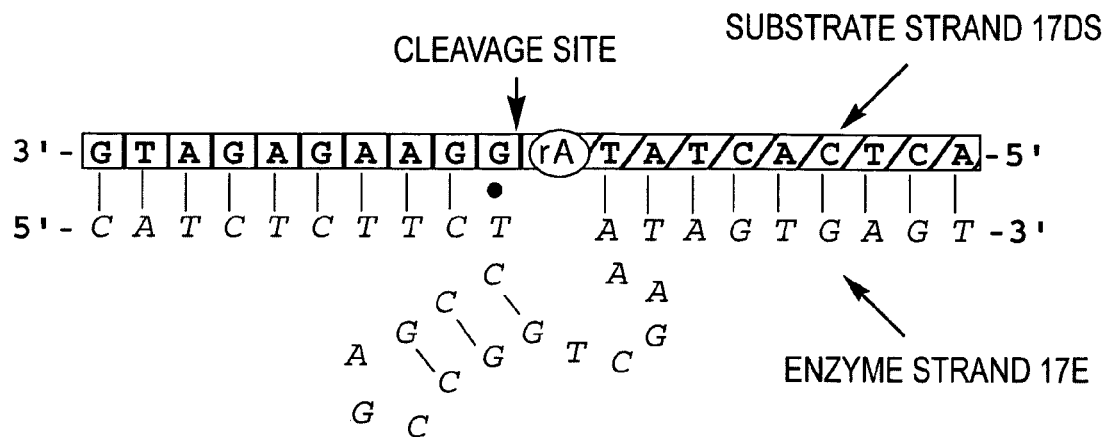
FIG. 1. (A) Secondary structure of the "8-17" DNAzyme system that consists of an enzyme strand (17E, SEQ ID NO: 1) and a substrate strand (17DS. SEQ ID NO: 10). (B) Cleavage of 17DS by 17E in the presence of Pb(II). (C) Schematics of DNAzyme-directed assembly of gold particles and their application as biosensors for metal ions such as Pb(II). The oligonucleotide functionalized to the gold nanoparticle ($DNA_{Au}$) is disclosed as SEQ ID NO: 11, while the 17DS substrate strand extended with nucleotides complimentary to the particles ($Sub_{Au}$) is disclosed as SEQ ID NO:12.
Figure 1B:
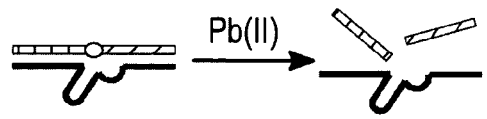
Figure 1C:
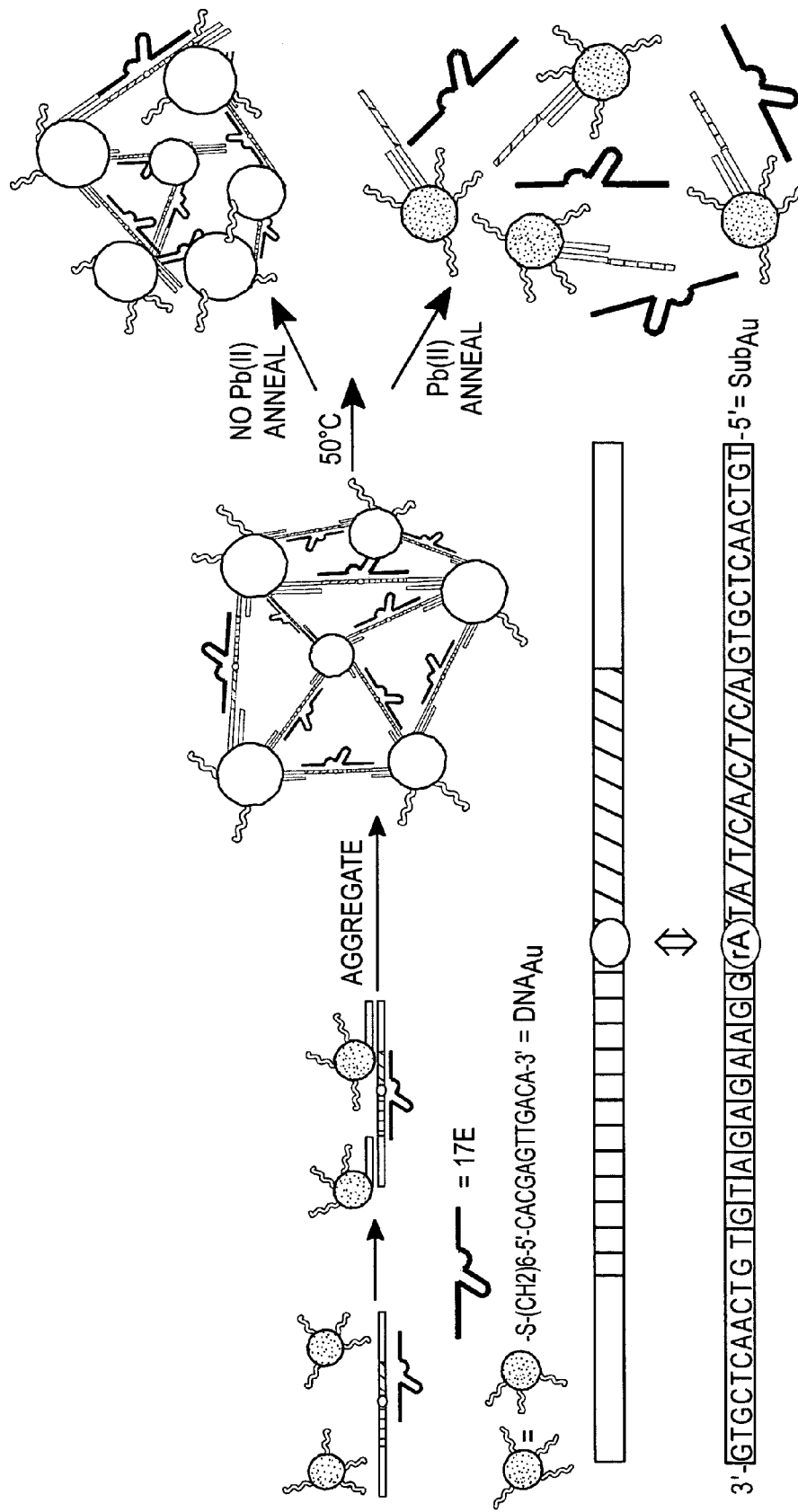

A nucleic acid enzyme that cleaves a nucleic acid strand separate from the strand comprising the enzyme is a trans-acting enzyme. Using trans-acting enzymes allows for multiple rounds of substrate cleavages, since the enzymatic product is removed. An example of such a nucleic acid enzyme is 17E (SEQ ID NO:1); the corresponding substrate is 17DS (SEQ ID NO:2; r denotes a single ribonucleotide); both are presented in Table 3A and illustrated in FIG. 1. The secondary structure of the "8-17" DNAzyme system, including an enzyme strand (17E) and a substrate strand (17DS), is illustrated in FIG. 1a. The cleavage site is indicated by an arrow. Except for a ribonucleoside adenosine at the cleavage site (rA), all other nucleosides are deoxyribonucleosides. In the presence of Pb(II), the enzyme strand cleaves the substrate strand (FIG. 1b). Thus, as illustrated in FIG. 1c, the enzyme strand and the substrate strand may be used in the DNAzyme-directed assembly of gold particles and in its application as a biosensor for metal ions such as Pb(II). In this system, the 17DS has been extended on both the 3' and 5' ends for 12 bases, which are complementary to the 12-mer DNA attached to the 13 nm gold particles (DNA$_{Au}$). Other examples are also given in Table 3B.

TABLE 3A

DNA enzymes and substrates

| Molecule | SEQ ID NO: | Sequence | # of nucleotides |
|---|---|---|---|
| Enzyme (17E) | 1 | 5'-catctcttct ccgagccggt cgaaatagtg agt-3' | 33 |
| Substrate for 17E (17DS)[c] | 2 | 5'-actcactatr ggaagagatg-3' | 20 |
| Enzyme: JLYL1 "8-17" half | 5 | 5'-tctcttctcc gagccggtcg aaatattgga ggaagctc-3' | 38 |
| ATP half | 6 | 5'-gagctggagg aaaaagtgag tc-3' | 22 |
| Sustrate for JLYL1 | 4 | 5'-gactcactat rggaagaga-3' | 19 |
| Enzyme: JLYL2 "8-17" half | 8 | 5'-tctcttct ccgagccggt cgaaatattg gaggaagctc-3' | 38 |
| ATP half | 9 | 5'-gagctggagg aaaaagtgag tc-3' | 22 |
| Substrate for JLYL2 | 7 | 5'-actcatctgt gagactcact atrggaagag atgtcaactc gtg-3' | 43 |

[c]"r" denotes a single ribonucleotide

TABLE 3B

RNA/DNA based aptamers and RNA/DNAzymes

| RNA/DNA based aptamers and their targets[1-4] | | RNA/DNAzymes[5,6-10] |
|---|---|---|
| Organic dyes[11,12] | Xanthene[59] | 8-17 DNAzyme[13-15] |
| Theophyllin[16] | Kanamycin A[60] | 10-23 DNAzymes[13,17] |
| Dopamine[18] | Lividomycin[60] | Hammerhead[19,20] |
| Hoechst 33258[21] | Tobramycin[61] | Hairpin[19,22] |
| Sulforhodamine B[23,24] | Neomycin B[62,63] | Leadzyme[25] |
| Cellobiose[26] | Viomycin[64] | Hepatitis Delta Virus[27,28] |
| D-tryptophan[29] | Chloramphenicol[65] | Group I Intron[30,31] |
| L-arginine[32-27] | Streptomycin[66] | Spliceosome[38] |
| L-citrullin[32,36] | HIV-1 Rev peptide[67,68] | Ribosome[39] |
| L-argininamide[40] | Vasopressin[69] | DNA nuclease activity[41] |
| L-valine[42] | Spectinomycin[70] | Ligase activity[43] |
| L-isoleucine[44] | L-tyrosinamide[71] | Kinase activity[45] |
| AMP/ATP[46-50] | HIV-1 RNase H[72] | Phosphoramidate bond cleavage[51] |
| Guanosine[52] | Chitin[73] | Porphyrin metallation[53] |
| FMN[47,54] | Human Thrombin[74] | Peroxidase activity[55] |
| NAD[54] | cAMP[75] | |
| Vitamin $B_{12}$[56] | Cholic acid[76] | |
| 8-oxo-dG[57] | Hematoporphyrin[77] | |
| 5'-cap58 | HIV-1 Tat/$Zn^{2+}$[78] | |
| | Anthrax spores[79] | |

Directed mutagenesis can be used to change one or more properties of a nucleic acid enzyme or its substrate. Using 17E and 17DS as an example, one may wish to alter the avidity of the two arms of the hybridized enzyme and substrate. The "arms" are those areas displaying Watson-Crick base-pairing in FIG. 1. To alter avidity, the length of the arms is changed. Increasing the length of the arms increases the number of Watson-Crick base pairings, thus increasing avidity; decreasing the length decreases avidity. Decreasing the avidity of the arms facilitates the removal of substrate from the enzyme, thus allowing for faster enzymatic turnover.

Another method of decreasing avidity includes creating mismatches between the enzyme and the substrate. Alternatively, the G-C content of the arms may be altered. The effect of any directed change should be monitored to ensure that the enzyme retains the desired activity, including ion sensitivity and selectivity. For example, to ensure that the mutated enzyme maintains sensitivity and selectivity for adenosine, one would test to determine if the mutated enzyme remained reactive in the presence of adenosine (sensitivity) and maintained its lower level of activity in the presence of other effectors (selectivity).

In Vitro Selection of Aptamers

Aptamers and aptazymes that bind a desired effector can be isolated by in vitro selection. In vitro selection is a technique in which RNA or DNA molecules with certain functions are isolated from a large number of sequence variants through multiple cycles of selection and amplification (Chapman and Szostak 1994, Joyce 1994). DNAzymes and RNAzymes with maximized activities or novel catalytic abilities, as well as aptamers, can be obtained using, for example, the technique of systematic evolution of ligands by exponential enrichment (SELEX) (Tuerk and Gold 1990).

In vitro selection is typically initiated with a large collection (pool) of randomized sequences, usually containing $10^{13}$-$10^{16}$ sequence variants. Chemical synthesis of a set of degenerated polynucleotides using standard phosphoramidite chemistry can be used to generate such randomized pools. The 3'-phosphoramidite compounds of the four nucleosides (adenosine, cytosine, guanine, thymidine) are premixed and used to synthesize the polynucleotides; randomness is generated by controlling the ratio of the four phosphoroamidites. Biases can also be achieved, as well as holding a phosphoramidite constant at a specific position. Other strategies for creating randomized DNA libraries include mutagenic polymerase chain reaction (PCR) and template-directed mutagenesis (Cadwell and Joyce 1992, Cadwell and Joyce 1994, Tsang and Joyce 1996). If in vitro selection of RNA molecules is desired, randomized DNA libraries are first converted to an RNA library by in vitro transcription.

The randomized libraries are then screened for molecules possessing a desired function, such as binding the targeted effector, and are isolated. Separation may be achieved using affinity column chromatography (using, e.g., the targeted effector), gel electrophoresis, or selective amplification of a tagged reaction intermediate. The selected molecules are amplified, using, for example, PCR for DNA, or isothermal amplification reaction for RNA. These selected, amplified molecules are then mutated (reintroducing diversity) using, for example, mutagenic PCR to attempt to select for molecules with yet higher activity. These three steps, selection, amplification and mutation, are repeated, often with increasing selection stringency, until sequences with the desired activity dominate the pool.

Novel nucleic acid enzymes isolated from random sequences in vitro have extended the catalytic repertoire of RNA and DNA (Table 1). Deoxyribozymes catalyze fewer types of reactions compared to ribozymes (Table 2). The catalytic rate ($k_{cat}$) of most deoxyribozymes is comparable to that of ribozymes catalyzing the same reaction. In certain cases, the catalytic efficiency ($k_{cat}/K_m$) of nucleic acid enzymes even exceeds protein enzyme catalytic efficiency. (Santoro and Joyce 1997).

In vitro selection can be used to change the ion specificity or binding affinity of existing nucleic acid enzymes, or to obtain nucleic acid enzymes specific for desired substrates. For example, the $Mg^{2+}$ concentration required for optimal hammerhead ribozyme activity has been lowered using in vitro selection to improve the enzyme performance under physiological conditions (Conaty et al. 1999, Zillmann et al. 1997).

Often nucleic acid enzymes developed for a specific cofactor by in vitro selection will have activity in the presence of other molecules. For example, 17E deoxyribozyme was developed by in vitro selection for activity in the presence of $Zn^{2+}$. However, the enzyme showed greater activity in the presence of $Pb^{2+}$ than $Zn^{2+}$. Although produced in a process looking for $Zn^{2+}$-related activity, 17E may be used as a sensitive and selective sensor for $Pb^{2+}$. To produce nucleic acid enzymes with greater selectivity, a negative selection step may be introduced. (Peter J. Bruesehoff, Jing Li, Anthony J. Augustine III, and Yi Lu, "Improving Metal Ion Specificity During In Vitro Selection of Catalytic DNA" *Combinatorial Chemistry and High Throughput Screening* 5, 327-355 (2002)).

Other polynucleotide sequences are useful, including those described in U.S. patent application Ser. No. 09/605,558, filed Jun. 27t, 2000, the contents of which are incorporated by reference (Lu and Li).

Adenosine Sensor

Figure 2A:
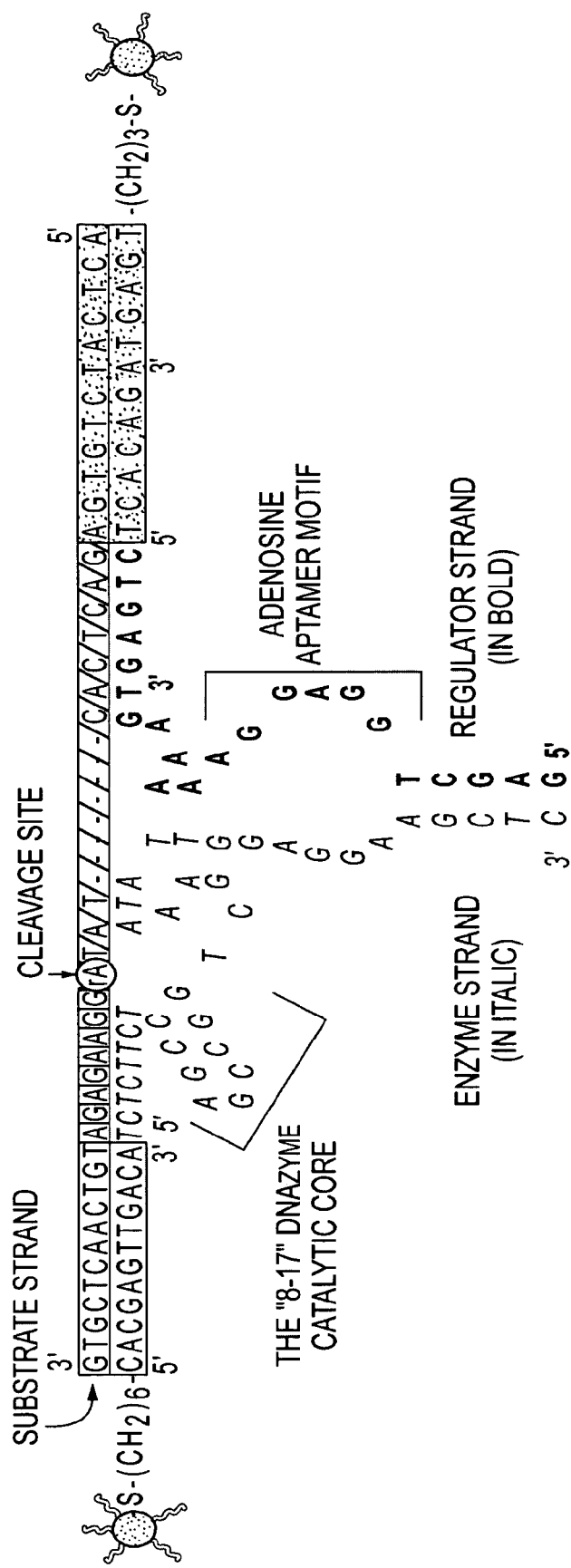
FIG. 2. (A) The primary and the proposed secondary structure of the adenosine aptazyme built on the "8-17" DNAzyme platform. The proposed secondary substrate is disclosed as SEQ ID NO: 13. The aptazyme sequence is disclosed as SEQ ID NOS 14 (left) and 15 (right). (B) Schematic representation of the colorimetric detection of adenosine.

The aptazyme shown in FIG. 2A is specific for adenosine. The catalytic core of the aptazyme is adapted from the "8-17" DNAzyme and has been optimized for high activity in the presence of $Pb^{2+}$. The 3'-end of the DNAzyme is linked to the adenosine aptamer motif. Therefore, the presence of adenosine can promote formation of the active tertiary DNAzyme structure. In an aptazyme-based sensor, this complex promotes cleavage of the substrate strand at the single riboadenosine position. Without adenosine, even though the three components may still be able to come together by Watson-Crick base-paring, the cleavage activity is dramatically reduced. Also shown are two DNA-functionalized 13 nm diameter gold particles, hybridized to both ends of the aptazyme.

Figure 2B:
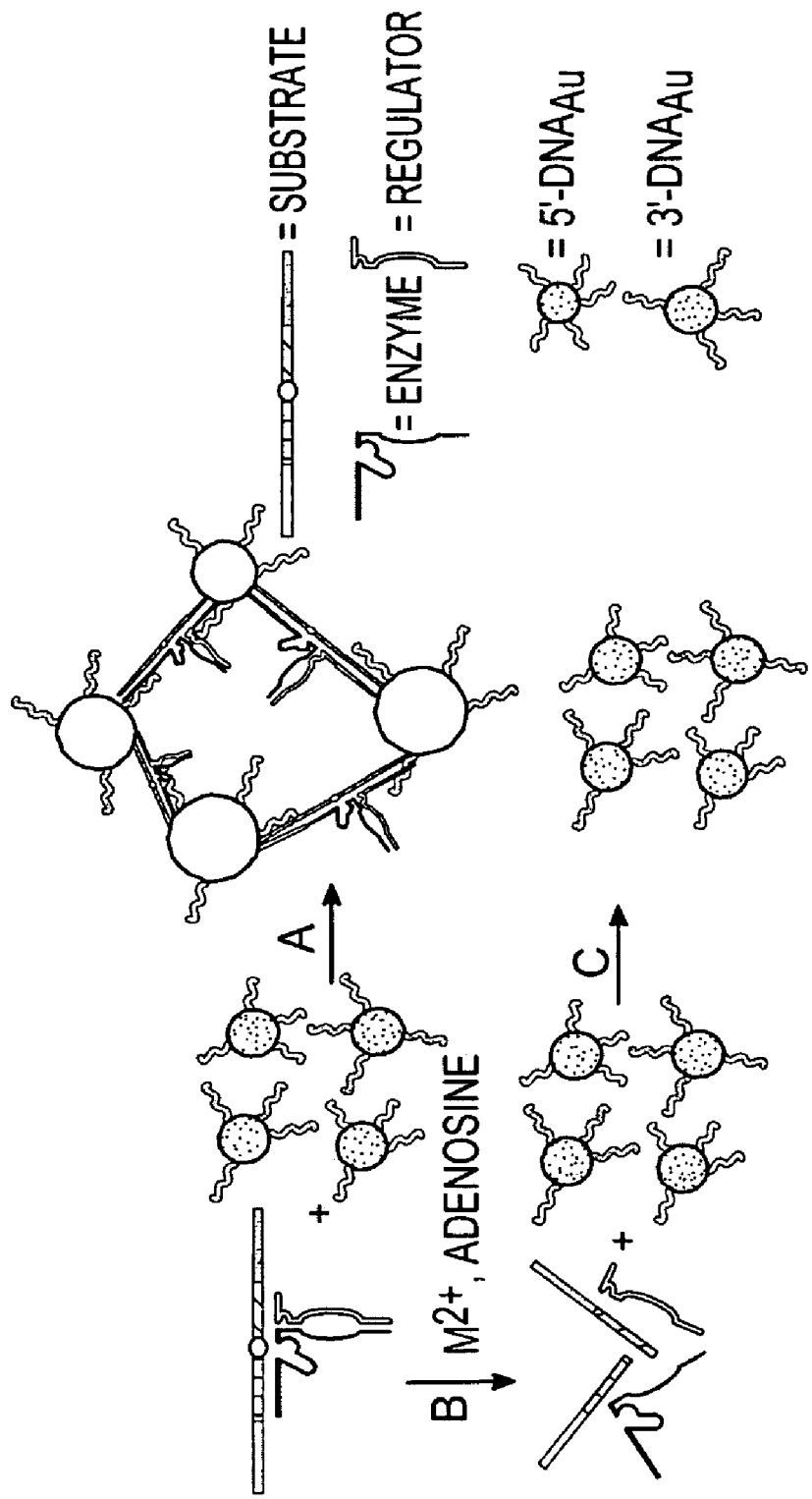

As illustrated in FIG. 2B, The substrate strands (both free substrate and substrate hybridized with the enzyme and regulator strands) can act as linkers for the DNA-functionalized gold particles to form aggregates, which have a blue color (reaction A). In the presence of adenosine and metal ions, the substrate can be cleaved (reaction B). The cleaved substrate can no longer act as linkers for particles and the color remains red (reaction C).

Figure 8:
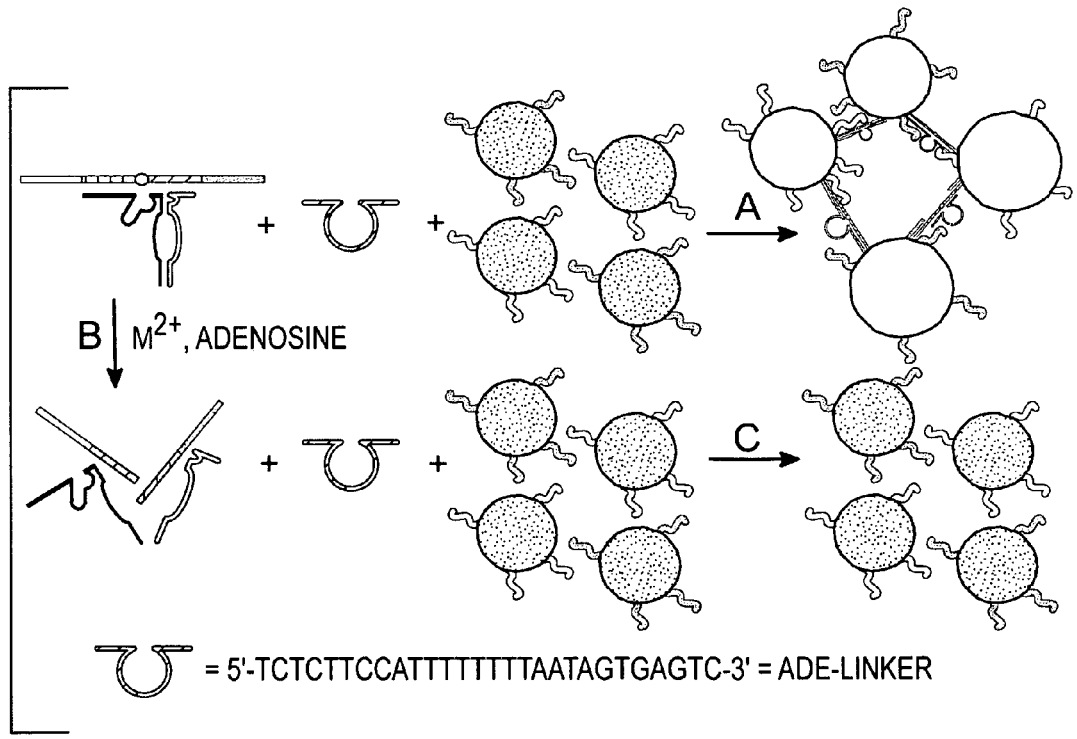
FIG. 8. A new design of an aptazyme-based adenosine sensor (SEQ ID NO: 16). Reaction A: formation of blue aggregates in the absence of adenosine. Reaction B: the substrate is cleaved in the presence of adenosine. Reaction C: the cleaved substrate cannot assemble gold particles, yielding red-colored, separated particles.

In this type of sensor, the presence of the substrate, enzyme and regulator strands is insufficient for aggregate formation at room temperature. It is difficult for all the three strands to hybridize and act as linkers without heating. To solve this problem, another DNA strand ("Ade-linker") is introduced (FIG. 8). The purpose of Ade-linker is to hybridize to the substrate strand with high efficiency and facilitate the aggregation of particles at room temperature. After hybridization, the Ade-linker forms a bulged secondary structure with 10 nucleotides. The bulge prevents the Ade-linker from using cleaved substrate as linkers to assemble particles. With the bulge, even if some Ade-linkers hybridize to the cleaved substrate, the whole structure is still floppy, and incapable of assembling particles.

If no adenosine is present, the substrate of the aptazyme hybridizes with Ade-linker, and the hybridized product can assemble particles to form blue aggregates (reaction A). In the presence of adenosine, the substrate strand is cleaved (reaction B), and the cleaved substrate cannot assemble gold particles, yielding red-colored, separated particles (reaction C).

Particles Tagged with Polynucleotides Complementary to the 3' and 5' Termini of the Nucleic Acid Enzyme Substrate For the sensor to register enzymatic activity, a detectable change must occur upon a change in aggregation of the particles to which the polynucleotides are attached. In addition, the composition of the particles must be such that they do not interfere with substrate cleavage. Particles may be made of, for example, metals, semiconductors and magnetic materials; ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs (e.g., (Mirkin et al. 2002)); and preferably gold particles (commercially available; e.g., Amersham Biosciences; Piscataway, N.J. and Nanoprobes, Inc; Yaphank, N.Y.). Non-metal particles may also be used, including ceramics and polymers, such as polystyrene latex particles or latex particles containing dye. Preferably the particles have an average particle diameter of at least 20 nm, more preferably at least 30 nm, even more preferably at least 35 nm, including 15-500 nm, 20-200 nm, and 35-100 nm.

Gold colloidal particles with a diameter of at least 35 nm are preferred. Gold colloidal particles have high extinction coefficients for the bands that give rise to their intense colors. These colors vary with particle size, concentration, interparticle distance, extent of aggregation and shape of the aggregates. For instance, the aggregation of gold particles driven by the hybridization of polynucleotides attached to the particles results in an immediate color change visible to the naked eye (see, e.g., (Mirkin et al. 2002)).

The particles, polynucleotides or both are derivatized for the attachment. For instance, polynucleotides derivatized with alkanethiols at their 3'- or 5'-termini readily attach to gold particles (Whitesides 1995). A method of attaching 3' thiol DNA to flat gold surfaces can also be used to attach polynucleotides to particles (Mucic et al. 1996). Alkanethiol-derivatized particles can be used to attach polynucleotides. Other functional groups for attaching polynucleotides to solid surfaces include phosphorothioates, which attach polynucleotides to gold surfaces (Beebe and Rabke-Clemmer 1995), substituted alkylsiloxanes for binding polynucleotides to silica and glass surfaces, aminoalkylsiloxanes and mercaptoaklylsiloxanes (Grabar et al. 1995). Polynucleotides terminating in a 5'-thionucleoside or a 3'-thionucleoside may also be used for attaching polynucleotides to solid surfaces. Some methods of attaching polynucleotides are presented in Table 4.

TABLE 4

Systems for attaching polynucleotides to particles

| System | Reference |
| --- | --- |
| biotin-streptavidin | (Shaiu et al. 1993) |
| carboxylic acids on aluminum | (Allara and Nuzzo 1985) |
| disulfides on gold | (Nuzzo et al. 1987) |
| carboxylic acids on silica | (Iler 1979, Tompkins and Allara 1974) |
| carboxylic acids on platinum | (Timmons and Zisman 1965) |
| aromatic ring compounds on platinum | (Soriaga and Hubbard 1982) |
| silanes on silica | (Maoz and Sagiv 1987) |

Particle Alignment

In order for the particles to align in the "tail-to-tail" manner, the particles are functionalized in the following fashion. Particles that bind to the substrate at a site 5' of the substrate are functionalized with complementary polynucleotide strands that are linked at their 3' termini to the particles, whereas particles that bind to the substrate at a site 3' of the substrate are functionalized with complementary polynucleotide strands that are linked at their 5' termini to the particles. The substrate-particle complex has the structure illustrated in FIG. 3B, rather than the structure illustrated in FIG. 3A.

Preferably, the substrate is modified to facilitate annealing to the complementary polynucleotide strand attached to the particles, for example, by extension of the 3'- and 5'-ends by a number of bases that act as "sticky ends". Substrate modification allows complexes comprising substrate-linked particles to be formed without inhibiting the nucleic acid enzyme/substrate interaction. However, where the substrate contains regions not critical for interaction with the nucleic acid enzyme, modification may not be necessary.

It is also possible for the particles to be attached directly to the substrate, or alternatively, for one end of the substrate to be attached to a particle, and for the other end to be complementary to a polynucleotide which is attached a particle. Therefore, the complementary polynucleotides are optional.

To detect the target cofactor or effector, the nucleic acid enzyme, substrate, and labeled particles are combined in the presence of a sample suspected of containing a target cofactor or effector, such as adenosine, to which the enzyme is sensitive (FIG. 3). In the presence of the cofactor or effector, the enzyme cleaves the substrate, preventing aggregate formation.

Different aggregation states of the particles results in different colors. For example, a large degree of gold particle aggregation displays blue colors while a small degree of particle aggregation displays red colors. Furthermore, the amount of substrate cleavage and thus the degree of aggregation depends on the concentration of the cofactor or effector.

A low cofactor or effector concentration results in only partial substrate cleavage that produces a mixture of single particles and aggregates, allowing for semi-quantitative or qualitative assays. The color difference can be amplified to improve sensitivity. For a quantitative measurement, the optical spectra of the assay mixture are determined. In addition to color change, the formation of aggregates of the particles, or precipitation of aggregated particles may also be monitored. Color changes can be observed with the naked eye or spectroscopically. The formation of aggregates can be observed by electron microscopy or by nephelometry; precipitation of aggregated particles can be observed with the naked eye or microscopically.

To facilitate the observation of a color change, the color may be observed on a background of a contrasting color. When gold particles are used, the observation of a color change is facilitated by spotting a sample of the hybridization solution on a solid white surface (such as silica or alumina TLC plates, filter paper, cellulose nitrate membranes, and nylon membranes) and allowing the spot to dry. Initially, the spot retains the color of the hybridization solution (which ranges from pink/red, in the absence of aggregation, to purplish-red/purple, if there has been aggregation of gold particles). On drying, a blue spot develops if aggregation is present prior to spotting; a pink spot develops if dispersion occurred. The blue and the pink spots are stable and do not change on subsequent cooling or heating or over time. They provide a convenient permanent record of the test. No other steps are necessary to observe the color change.

Alternatively, assay results may be visualized by spotting a sample onto a glass fiber filter for use with 35 nm gold particles. After rinsing with water, a spot comprising the aggregates is observed. Additional methods are also available for visualizing assay results (Mirkin et al. 2002).

The targeted cofactor or effector can be detected in a variety of samples, including biological samples. Standards containing known amounts of the cofactor or effector may be assayed along side the unknown sample, and the color changes compared. Alternatively, standard color charts, similar to those used with pH papers, may be provided.

Kits

The invention also provides kits for detecting analytes as cofactors or effectors. In one embodiment, the kit includes at least one container, the container holding at least two types of particles having polynucleotides attached thereto; a substrate, the substrate having at least three portions, the first portion being 5' to the second portion, the second portion being cleaved by the nucleic acid enzyme in the presence of the analyte, and the third portion being 3' to the second portion; and a nucleic acid enzyme. The polynucleotides attached to the first particles have a sequence complementary to the sequence of at least the first portion of the substrate and are attached to the particles at their 5' termini. The polynucleotides attached to the second particles have a sequence complementary to the sequence of at least the third portion of the substrate, and are attached to the particles at their 3' termini.

When a kit is supplied, the different components of the composition may be packaged in separate containers and admixed immediately before use. Such packaging of the components separately permits long-term storage of the active components. For example, one of more of the particles having polynucleotides attached thereto; the substrate; and the nucleic acid enzyme are supplied in separate containers.

The reagents included in the kits can be supplied in containers of any sort such that the life of the different components are preserved and are not adsorbed or altered by the materials of the container. For example, sealed glass ampules may contain one of more of the reagents, or buffers that have been packaged under a neutral, non-reacting gas, such as nitrogen. Ampules may consist of any suitable material, such as glass, organic polymers, such as polycarbonate, polystyrene, etc.; ceramic, metal or any other material typically employed to hold similar reagents. Other examples of suitable containers include simple bottles that may be fabricated from similar substances as ampules; and envelopes that may comprise foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to be mixed. Removable membranes may be glass, plastic, rubber, etc.

The kits may also contain other reagents and items useful for detecting the targeted cofactor or effector. The reagents may include standard solutions containing known quantities of the cofactor or effector, dilution and other buffers, pretreatment reagents, etc. Other items which may be provided as part include a backing (for visualizing aggregate break down), such as a TLC silica plate; microporous materials, syringes, pipettes, cuvettes and containers. Standard charts indicating the appearance of the particles in various aggregation states, corresponding to the presence of different amounts of the cofactor or effector being tested, may be provided.

Kits may also be supplied with instructional materials. Instructions may be printed on paper or other substrate, and/or may be supplied as an electronic-readable medium, such as a floppy disc, CD-ROM, DVD-ROM, Zip disc, videotape, audiotape, etc. Detailed instructions may not be physically associated with the kit; instead, a user may be directed to an internet web site specified by the manufacturer or distributor of the kit, or supplied as electronic mail.

EXAMPLES

Example 1 Colorimetric $Pb^{2+}$ Biosensor

Polynucleotides and Reagents

All polynucleotides were purchased from Integrated DNA Technology Inc. (Coralville, Iowa). Adenosine and other nucleosides were purchased from Sigma-Aldrich (St. Louis, Mo.). Thirty-five nm diameter gold particles were prepared and 3'- and 5'-thiol-modified 12-mer DNA was attached (Storhoff et al. 1998). The substrates and the enzymes were purified by HPLC.

Preparation and Functionalization of Gold Particles

Thirty-five nm diameter gold particles were prepared by the reduction of $HAuCl_4$ by sodium citrate. Glassware used in the preparation was soaked in aqua regia and rinsed thoroughly with Millipore water. In a 250 mL two-neck flask, 200 mL 0.3 mM $HAuCl_4$ was heated to reflux under stirring. Two mL 38.8 mM sodium citrate was then added. Within several minutes, the color changed from pale yellow to deep red. After the color change, the system was allowed to reflux for another half hour for reduction to complete. Then the system was cooled slowly to room temperature, and the particles were filtered with a Pyrex funnel. The particles were characterized using transmission electron microscopy (TEM) on a JEOL 2010 electron microscope, and the size was determined to be 35±6 nm. Most of the particles had a spherical shape, and a small portion of particles were rods with aspect ratios less than two. The gold colloid had an extinction peak at 532 nm of ~1, and the concentration was calculated to be approximately 0.23 nM by assuming all particles were spherical with radii of 35 nm; all HAuCl$_4$ was reacted and the density of particles were the same as bulk gold. This gave an extinction coefficient of $4.4 \times 10^9$ M$^{-1}$ cm$^{-1}$ at 532 nm.

Functionalization of Particles with 3'- and 5'-thiol Modified DNA

Thiol-modified DNA was activated by incubating with 50 mM dithiotreitol (DTT). Typically, 60/L of 1 mM DNA were incubated with 60 μL 100 mM DTT at room temperature (20-22° C.) for 2 hours. The mixture was then placed onto a Sep-Pak C18 column to remove DTT. The column was treated with 10 mL 95% CH$_3$CN, 10 mL mixture of CH$_3$CN, methanol and water with 1:1:1 volume ratio, 20 mL water and 10 mL 2 M NH$_4$OAc. DNA and DTT mixture were then loaded into the column. DTT was washed away by 20 mL de-ionized water, and DNA was eluted by 1 mL of 95% CH$_3$CN, 10 mL mixture of CH$_3$CN, methanol and water with 1:1:1 volume. The eluted DNA was added to 12 mL of gold particles (0.23 nM). After incubation for one day, 1.4 mL of buffer containing 1 M NaCl and 0.1 M Tris-acetate (TA), pH 7.2 was added. After another incubation of 2 days, the particles were collected by centrifugation at 8000 rpm for 10 minutes. Supernatants were removed, and the DNA-functionalized particles were redispersed in 25 mM TA buffer, pH 7.2, 100 mM NaCl. The process was repeated three times to ensure that free DNA was removed; and finally, the particles were dispersed in the same buffer and the extinction coefficient at 532 nm was adjusted to ~2.2 (corresponding to a concentration of ~0.5 nM).

Aggregation of Particles by the DNAzyme

In a typical experiment, 20 μL of 3'-thiol modified and 20 μL of 5'-thiol modified DNA functionalized gold particles, both at a concentration of ~0.5 nM, were mixed. NaCl, the enzyme (17E) and Pb$^{2+}$ were added, and the final volume was adjusted to 100 μL upon addition of the substrate. The aggregation was initiated by adding the substrate strand, and the extinction was monitored on a Hewlett-Packard 8453 spectrophotometer. The buffer was pH 7.2 TA for all experiments, except for pH-dependent studies. The time between substrate addition to the monitoring of the first spectrum was controlled to be 15 seconds for all samples.

Figure 4:
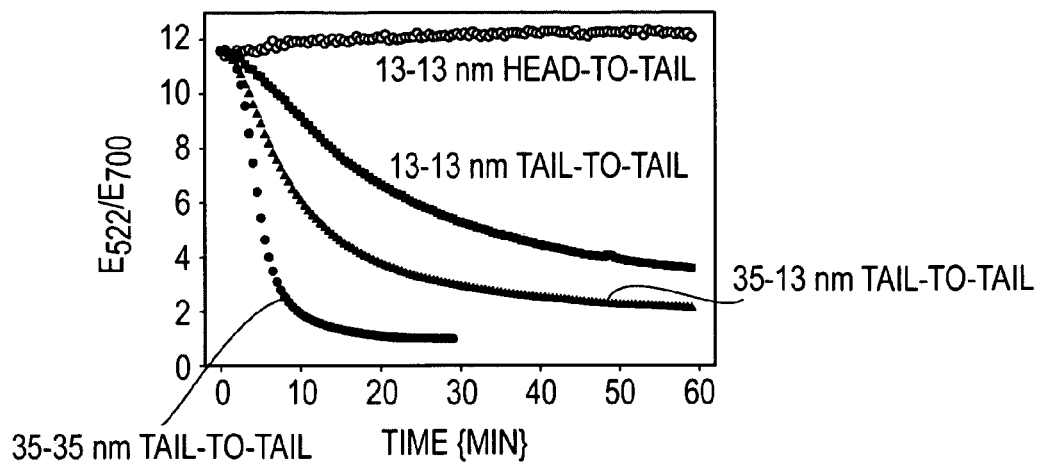

In the experiments illustrated in FIG. 4, the extinction ratio was normalized for better comparison. These experiments were run with 2 μM enzyme, the substrate concentration was 160 nM for 13 nm particles and 120 nM for 13 nm-35 nm mixed particles and 3 nM for 35 nm-35 nm particles. The buffer was pH 7.2, 25 mM TA.

Optimization of the new Pb$^{2+}$ sensor system (f) The extinction ratio after 10 minutes of aggregation.

Figure 6A:
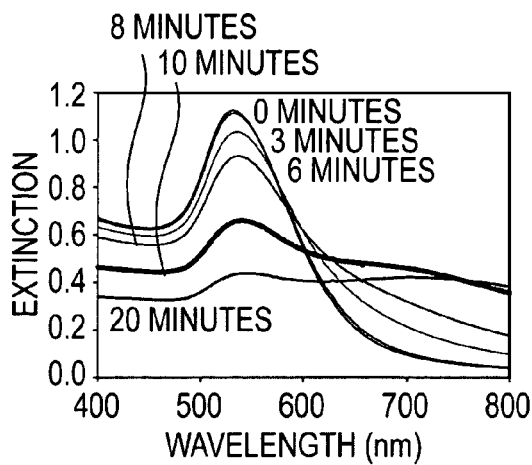
FIG. 6. A new $Pb^{2+}$ sensor system. (A). The extinction spectra of 35 nm gold particles at different times. (B) Effect of substrate concentration on the rate of aggregation. (C) Effect of NaCl concentration on the rate of aggregation. (D) Effect of 17E concentration on the rate of aggregation. (E) Aggregation of particles in different pH buffers. (f) Extinction ratio after 10 minutes of aggregation.

Clear red to blue color changes can be observed upon aggregation of the 35 nm gold particles, thus the aggregation process can be conveniently monitored by UV-visible spectroscopy. Shown in FIG. 6A are several spectra of the new sensor system with 3 nM of the linking substrate, NaCl 250 mM, and enzyme (17E) 1 μM, at different time points after the addition of the substrate strand. Before the substrate strand was added, the system showed a red color with an extinction peak at 532 nm, which was 10 nm red shifted compared to 13 nm diameter particles. In the first 3 minutes, the color change was very small. During this period it was thought that the substrate strands were base pairing with the enzyme strand, and the hybridized DNAzymes were linking to gold particles. In the next several minutes, the rate of color change was very fast, suggesting that the particles were cross-linking to form large aggregates. With the formation of aggregates, the extinction at the 532 nm peak decreased, while it increased in the 700 nm region, yielding the red-to-blue color transition. After 10 minutes, the aggregates began to precipitate, resulting in the decrease of observed extinction at all wavelengths. To minimize the effects of differences in sample preparations and concentration of particles, the extinction ratio of 532 nm and 700 nm was used to monitor the rate of color change, with a higher ratio associated with red color, and a lower ratio associated with blue color.

Figure 6B:
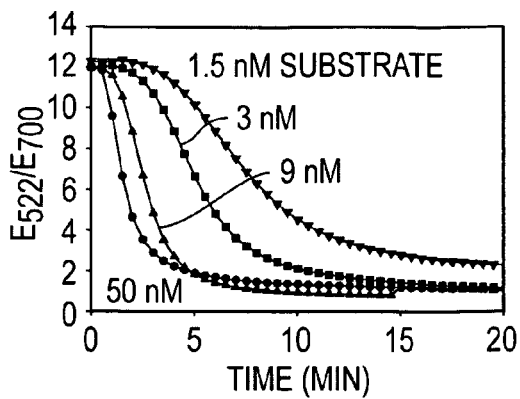

Illustrated in FIG. 6B are the rates of color change in the presence of different substrate concentrations. Higher substrate concentrations yielded higher rates of color change. Thus, the decrease of substrate concentration resulted in a "less blue" or a "more red" color at a set time. Different Pb$^{2+}$ concentrations cleaved the substrate at different rates; thus, by inspecting the color displayed by the sensor, Pb$^{2+}$ was detected and quantified. The experiments were performed using 3 nM substrate, NaCl 250 mM and 17E 1 μM.

Additional Factors Influencing Aggregation.

Figure 6C:
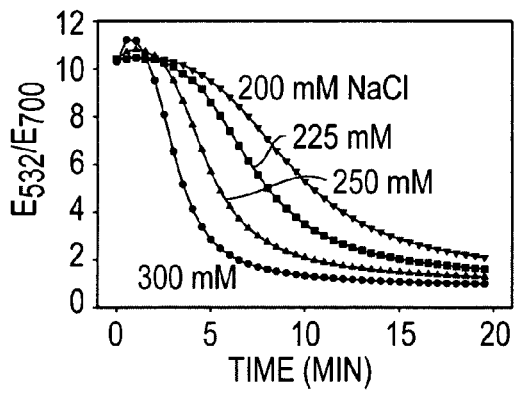

As outlined above, other factors were found to affect the rate of aggregation of particles, such as the enzyme concentration, salt concentration and pH values. The experiments illustrated in FIG. 6C were all run with 3 nM substrate concentration and 1 μM 17E enzyme concentration, and with varying NaCl concentrations. Higher NaCl concentrations favored aggregation, likely because NaCl reduced the electrostatic repulsion between the negative charges of the negatively charged DNA.

Figure 6D:
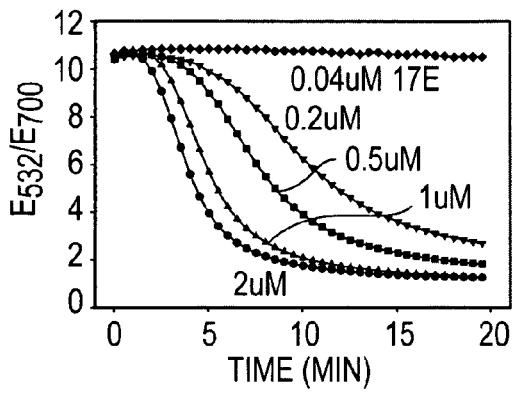

The enzyme concentration also had significant effect on the aggregation of particles. The experiments illustrated in FIG. 6D were all run at 0.3 nM substrate concentration and 250 mM NaCl concentration, and with varying 17E enzyme concentrations. Higher concentrations of the enzyme strand yielded faster aggregation rates. In the absence of the enzyme or when the enzyme concentration was very low (FIG. 6D, topmost curve), aggregation was inhibited. Although physically only the substrate strand was acting as linkers to assemble particles, the presence of the enzyme strand appears to be optional. From these observations, it was hypothesized that the first step of aggregation is the hybridization of the substrate strand to the enzyme strand. Then the hybridized DNAzyme can assemble gold particles. In the absence of the enzyme strand, the substrate by itself is likely to be too floppy to assemble gold particles.

Figure 6E:
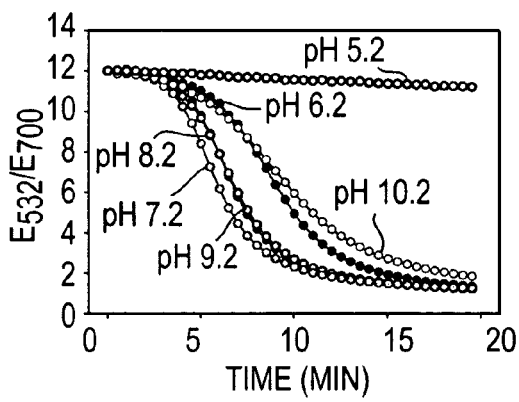
Figure 6F:
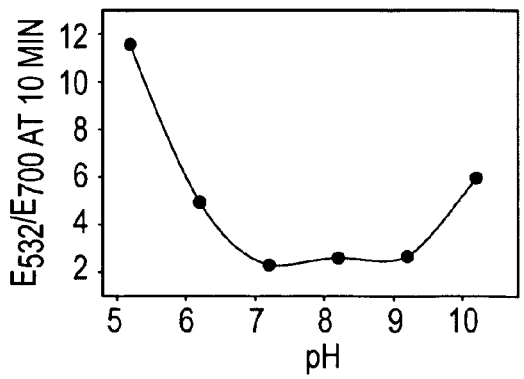

Different pH values also influenced aggregation. As shown in FIG. 6E, from pH 5.2 to pH 10.2 (pH 5.2, acetate buffer, pH 6.2 MES buffer, pH 7.2-10.2, TA buffer), all the samples gave a sigmoidal curve, which was characteristic for the DNAzyme directed assembly of gold particles at room temperature (20-22° C.). For the pH 5.2 sample, the aggregation of particles appeared inhibited. The extinction ratio after 10 minutes aggregation was plotted and is presented in FIG. 6F. From pH 7.2 to 9.2, similar extinction properties have been observed, suggesting a similar rate of aggregation, while the rate of aggregation decreases for both higher and lower pH. The sensor may thus be used in the pH range from about 6.2 to about 10.2, with optimal performance from about pH 7.2 to about 9.2. The change of rate of particle aggregation was likely due to protonation and deprotonation of the DNA bases at low or high pH, which affected the base pairing, thus leading to a change in aggregation rate.

Aggregation at Room Temperature

Figure 7A:
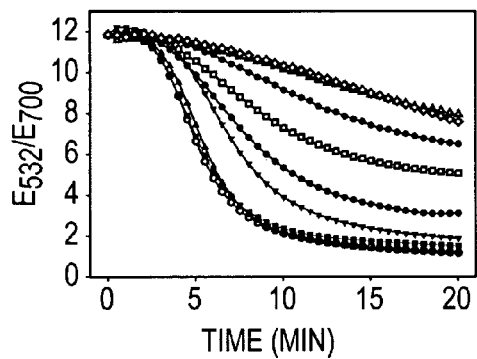
FIG. 7. Sensitivity and selectivity of a new $Pb^{2+}$ sensor. (A) Kinetics of gold particle aggregation with different $Pb^{2+}$ concentrations. (B) The extinction ratio at 10 minutes after the initiation.
Figure 7B:
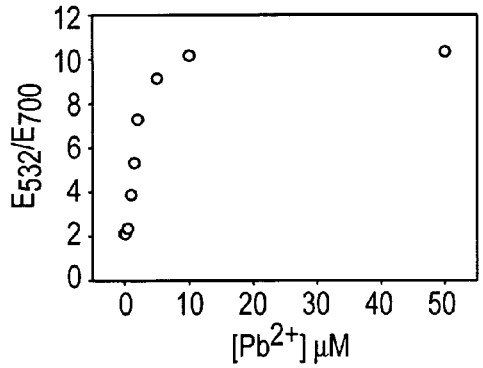

The kinetics of aggregation at room temperature (20-22° C.) of the new sensor with different Pb$^{2+}$ concentrations was monitored by UV-visible spectroscopy. It is hypothesized that in the presence of Pb$^{2+}$, after the hybridization of the substrate to the enzyme strand, the substrate strand could be either cleaved by the enzyme strand or be a linker to assemble particles. The relative rate of the two processes depends on the concentration of $Pb^{2+}$. As shown in FIG. 7A, as $Pb^{2+}$ concentration increased, the rate of aggregation was suppressed. For the sample without $Pb^{2+}$ added, the aggregation was almost complete after 10 minutes. The extinction ratio at 10 minutes was used to quantify $Pb^{2+}$ concentration (FIG. 7B).

Example 2 Colorimetric Adenosine Biosensor

Aggregation of Particles by the Aptazyme

To determine the optimal concentration of the substrate strand for the aptazyme-based sensor, 20 µL of each particle solution ($E_{532}$=2.2) were mixed and Ade-linker was added to a final concentration of 5 µM, NaCl to a final concentration of 250 mM, and the volume was adjusted to 100 µL after adding the substrate. The solution was in 25 mM TA buffer, at pH 7.2.

The solution was used to prepare a second solution with a final concentration of 0.15 µM substrate strand, 3 µM enzyme and regulator strand, 5 mM adenosine, 250 mM NaCl and 25 mM TA buffer, pH 7.2. Ninety-eight µL of the second solution were transferred in a reaction tube, and this moment was set as the 0 point. Two µL of metal ions stock solution was added to the reaction tube to initiate the cleavage reaction, and 2/L aliquots were transferred into detection tubes at different time points. Once each aliquot was transferred from the reaction tube to a detection tube, the cleavage reaction was quenched by the addition of EDTA in the detection tube. A 2 mL aliquot from the reaction tube contained 0.3 pmol substrate and would have given a substrate concentration of 3 nM in the detection tube if no cleavage occurred. The extinction spectrum of each sample in the reaction tube was monitored at 20 minutes after the transfer of the aliquot from the reaction tube.

To test of the sensitivity and selectivity of the sensor, different reaction tubes were prepared with different concentrations of adenosine or other nucleosides. After 30 minutes of incubation, 2 µL aliquots was transferred to detection tubes, and the extinction spectra of the detection tubes were measured after 20 minutes of incubation.

Figure 9A:
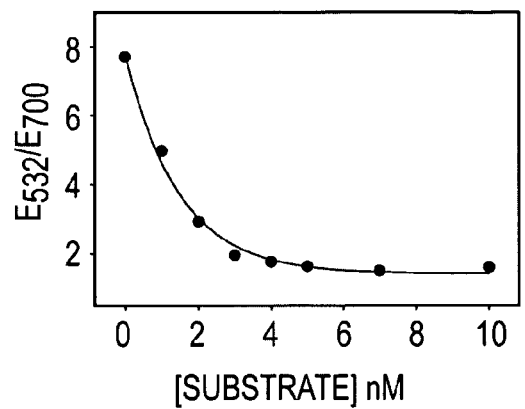
FIG. 9. (A) Substrate concentration-dependent aggregation of particles. (B) Kinetics of the cleavage of the substrate by the aptazyme. (C) Sensitivity and selectivity of an aptazyme-based sensor for adenosine.
Figure 9B:
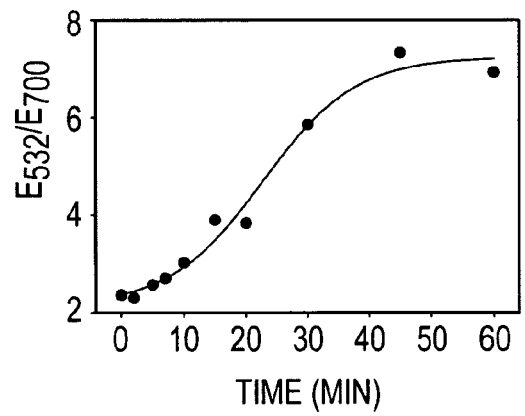
Figure 9C:
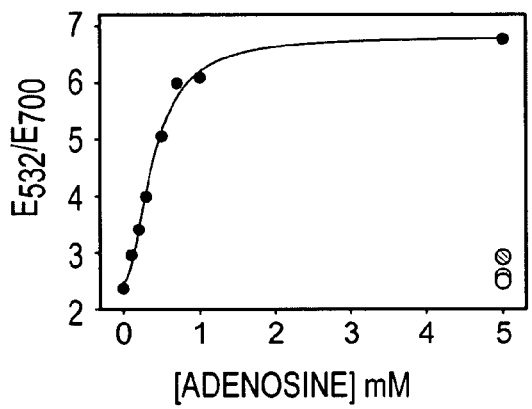

FIG. 9A illustrates the substrate concentration-dependent aggregation of particles, measured by the extinction spectra after 20 minutes of aggregation. FIG. 9B illustrates the kinetics of the cleavage of the substrate by the aptazyme. FIG. 9C shows the sensitivity and selectivity of the newly designed aptazyme-based sensor for adenosine. The pink, red and blue dots are the extinction ratio of 5 mM of cytidine, gaunosine and uridine, respectively.

REFERENCES (References for Table 3B are Found Below, Separately)

Allara D, Nuzzo R. (1985) Spontaneously organized molecular assemblies. 1. Formation, dynamics and physical properties of n-alkanoic acids adsorbed from solution on an oxidized aluminum surface. *Langmuir* 1: 45-52.
Beebe T, Rabke-Clemmer C, (1995) Thiol labeling of DNA for attachment to gold surfaces. U.S. Pat. No. 5,472,881 USA.
Biroccio A, Hamm J, Incitti I, De Francesco R, Tomei L. (2002) Selection of RNA aptamers that are specific and high-affinity ligands of the hepatitis C virus RNA-dependent RNA polymerase. *J Virol* 76: 3688-3696.
Breaker R R, Joyce G F, Breaker R R, Joyce G F. (1995) A DNA enzyme with Mg(2+)-dependent RNA phosphoesterase activity. A DNA enzyme that cleaves RNA. *Chem Biol; Chem Biol* 2; 1: 223-229.
Breaker R R, Joyce G F. (1994) A DNA enzyme that cleaves RNA. *Chem Biol* 1: 223-229.
Breaker R R. (2002) Engineered allosteric ribozymes as biosensor components. *Curr Opin Biotechnol* 13: 31-39.
Brody E N, Gold L. (2000) Aptamers as therapeutic and diagnostic agents. *J Biotechnol* 74: 5-13.
Brown A, Pavot C, Li J, Lu Y. A lead-dependent DNAzyme with a two-step mechanism. submitted.
Bruno J G, Kiel J L. (1999) In vitro selection of DNA aptamers to anthrax spores with electrochemiluminescence detection. *Biosens Bioelectron* 14: 457-464.
Bruno J G, Kiel J L. (2002) Use of magnetic beads in selection and detection of biotoxin aptamers by electrochemiluminescence and enzymatic methods. *Biotechniques* 32: 178-80, 182-3.
Cadwell R C, Joyce G F. (1992) Randomization of genes by PCR mutagenesis. *PCR Methods Appl* 2: 28-33.
Cadwell R C, Joyce G F. (1994) Mutagenic PCR. *PCR Methods Appl* 3: S136-40.
Cao Y, Jin R, Mirkin C A. (2001) DNA-modified core-shell Ag/Au particles. *J Am Chem Soc* 123: 7961-7962.
Carmi N, Shultz L A, Breaker R R. (1996) In vitro selection of self-cleaving DNAs. *Chem Biol* 3:1039-1046.
Chaloin L, Lehmann M J, Sczakiel G, Restle T. (2002) Endogenous expression of a high-affinity pseudoknot RNA aptamer suppresses replication of HIV-1. *Nucleic Acids Res* 30: 4001-4008.
Chapman K B, Szostak J W. (1994) In vitro selection of catalytic RNAs. *Curr Opin Struct Biol* 4: 618-622.
Ciesiolka J, Gorski J, Yarus M. (1995) Selection of an RNA domain that binds Zn2+. *RNA* 1: 538-550.
Conaty J, Hendry P, Lockett T. (1999) Selected classes of minimised hammerhead ribozyme have very high cleavage rates at low Mg2+ concentration. *Nucleic Acids Res* 27: 2400-2407.
Conn M, Prudent J, Schultz P. (1996) Porphyrin Metallation Catalyzed by a Small RNA Molecule. *J Am Chem Soc* 118: 7012-7013.
Cuenoud B, Szostak J W. (1995) A DNA metalloenzyme with DNA ligase activity. *Nature* 375: 611-614.
Dai X, De Mesmaeker A, Joyce G F. (1995) Cleavage of an amide bond by a ribozyme. *Science* 267: 237-240.
Earnshaw, Gait. (1998) Modified oligoribonucleotides as site-specific probes of RNA structure and function. *Biopolymers* 48: 39-55.
Ekland E H, Bartel D P. (1996) RNA-catalysed RNA polymerization using nucleoside triphosphates. *Nature* 382: 373-376.
Ekland E H, Szostak J W, Bartel D P. (1995) Structurally complex and highly active RNA ligases derived from random RNA sequences. *Science* 269: 364-370.
Ellington A D, Szostak J W. (1990) In vitro selection of RNA molecules that bind specific ligands. *Nature* 346: 818-822.
Faulhammer D, Famulok M. (1997) *Angew Chem Int Ed Engl* 35: 2837-2841.
Geyer C R, Sen D. (1997) Evidence for the metal-cofactor independence of an RNA phosphodiester-cleaving DNA enzyme. *Chem Biol* 4: 579-593.
Grabar K, Freeman R, Hommer M, Natan M. (1995) Preparation and characterization of Au colloid Monolayers. *Anal. Chem.* 67: 735-743.
Hesselberth J, Robertson M P, Jhaveri S, Ellington A D. (2000) In vitro selection of nucleic acids for diagnostic applications. *J Biotechnol* 74: 15-25.

Hofmann H P, Limmer S, Hornung V, Sprinzi M. (1997) Ni2+binding RNA motifs with an asymmetric purine-rich internal loop and a G-A base pair. *RNA* 3: 1289-1300.

Huizenga D E, Szostak J W. (1995) A DNA aptamer that binds adenosine and ATP. *Biochemistry* 34: 656-665.

Iler R. (1979) Chapter 6. In: anonymous (eds) *The chemistry of silica*. Wiley, New York.

Illangasekare M, Yarus M. (1997) Small-molecule-substrate interactions with a self-aminoacylating ribozyme. *J Mol Biol* 268: 631-639.

Jayasena S D. (1999) Aptamers: an emerging class of molecules that rival antibodies in diagnostics. *Clin Chem* 45: 1628-1650.

Jhaveri S, Kirby R, Conrad R, Maglott E, Bowser M, Kennedy R, Glick G, Ellington A. (2000) Designed signaling aptamers that transduce molecular recognition to changes in fluorescence intensity. *J. Am. Chem. Soc.* 122: 2469-2473.

Jhaveri S, Rajendran M, Ellington A D. (2000) In vitro selection of signaling aptamers. *Nat Biotechnol* 18: 1293-1297.

Joyce G F. (1994) In vitro evolution of nucleic acids. *Curr Opin Struct Biol* 4: 331-336.

Kiga D, Futamura Y, Sakamoto K, Yokoyama S. (1998) An RNA aptamer to the xanthine/guanine base with a distinctive mode of purine recognition. *Nucleic Acids Res* 26: 1755-1760.

Lauhon C T, Szostak J W. (1995) RNA aptamers that bind flavin and nicotinamide redox cofactors. *J Am Chem Soc* 117: 1246-1257.

Li J, Lu Y. (2000) A highly sensitive and selective catalytic DNA biosensor for lead ions. *J Am Chem Soc* 122: 10466-10467.

Li J, Zheng W, Kwon A H, Lu Y. (2000) In vitro selection and characterization of a highly efficient Zn(II)-dependent RNA-cleaving deoxyribozyme. *Nucleic Acids Res* 28: 481-488.

Li Y, Breaker R R. (1999) Phosphorylating DNA with DNA. *Proc Natl Acad Sci USA* 96: 2746-2751.

Li Y, Sen D. (1996) A catalytic DNA for porphyrin metallation. *Nat Struct Biol* 3: 743-7.

Link S, Wang Z, El-Sayed M. (1999) Alloy formation of gold-silver particles and the dependence of the plasmon absorption on their compositions. *J Phys Chem B* 103: 3529-3533.

Lohse P A, Szostak J W. (1996) Ribozyme-catalysed amino-acid transfer reactions. *Nature* 381: 442-444.

Lorsch J R, Szostak J W. (1994) In vitro evolution of new ribozymes with polynucleotide kinase activity. *Nature* 371: 31-36.

Lu Y. (2002) New transition-metal-dependent DNAzymes as efficient endonucleases and as selective metal biosensors. *Chemistry* 8: 4589-4596

Lu Y, Liu J, SIMPLE CATALYTIC DNA BIOSENSORS FOR IONS BASED ON COLOR CHANGES, application Ser. No. 09/605,558, USA.

Maoz R, Sagiv J. (1987) Penetration-controlled reactions in organized monolayer assemblies. 1. Aqueous permanganate interaction with monolayer and multilayer films of long-chain surfactants. *Langmuir* 3: 1034-1044.

Mirkin C A, Letsinger R L, Mucic R C, Storhoff J J. (1996) A DNA-based method for rationally assembling particles into macroscopic materials. *Nature* 382: 607-609.

Mirkin, C. A., Letsinger, L. R, Mucic, C. R, Storhoff, J. J, Elghanian R, (2002) Particles having polynucleotides attached thereto and uses therefor. U.S. Pat. No. 6,361,944 USA.

Mucic R, Herrlein M, Mirkin, C. A., Letsinger R. (1996) Synthesis and characterization of DNA with ferrocenyl groups attached to their 5'-termini: Electrochemical characterization of a redox-active nucleotide monolayer. *Chem. Commun.* 555.

Nuzzo R, Fusco F, Allara D. (1987) Spontaneously organized molecular assemblies, 3. Preparation and properties of solution adsorbed monolayers of organic disulfides on gold surfaces. *J Am Chem Soc* 109: 2358.

Piccirilli J A, McConnell T S, Zaug A J, Noller H F, Cech T R. (1992) Aminoacyl esterase activity of the Tetrahymena ribozyme. *Science* 256: 1420-1424.

Prudent J R, Uno T, Schultz P G. (1994) Expanding the scope of RNA catalysis. *Science* 264: 1924-1927.

Rakow N A, Suslick K S. (2000) A colorimetric sensor array for odour visualization. *Nature* 406: 710-713.

Robertson M P, Ellington A D. (1999) In vitro selection of an allosteric ribozyme that transduces analytes to amplicons. *Nat Biotechnol* 17: 62-66.

Roth A, Breaker R R. (1998) An amino acid as a cofactor for a catalytic polynucleotide. *Proc Natl Acad Sci USA* 95: 6027-6031.

Rusconi C P, Scardino E, Layzer J, Pitoc G A, Ortel T L, Monroe D, Sullenger B A. (2002) RNA aptamers as reversible antagonists of coagulation factor IXa. *Nature* 419: 90-94.

Santoro S W, Joyce G F. (1997) A general purpose RNA-cleaving DNA enzyme. *Proc Natl Acad Sci USA* 94: 4262-4266.

Seetharaman S, Zivarts M, Sudarsan N, Breaker R R. (2001) Immobilized RNA switches for the analysis of complex chemical and biological mixtures. *Nat Biotechnol* 19: 336-341.

Shaiu W L, Larson D D, Vesenka J, Henderson E. (1993) Atomic force microscopy of oriented linear DNA molecules labeled with 5 nm gold spheres. *Nucleic Acids Res* 21: 99-103.

Sillén L G, (1964) Stability constants of metal-ion complexes. Edition: 2d ed.

Smith J, Olson D, Armitage B. (1999) Molecular recognition of PNA-containing hybrids: Spontaneous assembly of helical cyanine dye aggregates on PNA templates. *J. Am. Chem. Soc.* 121: 2686-2695.

Soriaga M, Hubbard A. (1982) Determination of the orientation of aromatic molecules adsorbed on platinum electrodes: The influence of solute concentration. *J Am Chem Soc* 104.

Soukup G A, Breaker R R. (2000) Allosteric nucleic acid catalysts. *Curr Opin Struct Biol* 10: 318-325.

Stojanovic M N, Landry D W. (2002) Aptamer-based colorimetric probe for cocaine. *J Am Chem Soc* 124: 9678-9679.

Storhoff J, Elghanian R, Mucic R, Mirkin C, Letsinger R L. (1998) One-pot calorimetric differentiation of polynucleotides with single base imperfections using gold particle probes. *J Am Chem Soc* 120: 1959-1964.

Tang J, Breaker R R. (1997) Rational design of allosteric ribozymes. *Chem Biol* 4: 453-459.

Tang J, Breaker R R. (2000) Structural diversity of self-cleaving ribozymes. *Proc Natl Acad Sci USA* 97: 5784-5789.

Tarasow T M, Tarasow S L, Eaton B E. (1997) RNA-catalysed carbon-carbon bond formation. *Nature* 389: 54-57.

Timmons, Zisman. (1965) *J. Phys. Chem.* 69: 984-990.

Tompkins H, Allara D. (1974) The study of the gas-solid interaction of acetic acid with a cuprous oxide surface using reflection-absorption spectroscopy. *J. Colloid and Interface Sci.* 49410.

Tsang J, Joyce G F. (1996) In vitro evolution of randomized ribozymes. *Methods Enzymol* 267: 410-426.

Tuerk C, Gold L. (1990) Systematic evolution of ligands by exponential enrichment: RNA ligands to bacteriophage T4 DNA polymerase. Science 249: 505-510.

Vaish N K, Heaton P A, Fedorova O, Eckstein F. (1998) In vitro selection of a purine nucleotide-specific hammerheadlike ribozyme. *Proc Natl Acad Sci USA* 95: 2158-2162.

Wallace S T, Schroeder R. (1998) In vitro selection and characterization of streptomycin-binding RNAs: recognition discrimination between antibiotics. *RNA* 4: 112-123.

Wallis M G, Streicher B, Wank H, von Ahsen U, Clodi E, Wallace S T, Famulok M, Schroeder R. (1997) In vitro selection of a viomycin-binding RNA pseudoknot. *Chem Biol* 4: 357-366.

Wang D Y, Lai B H, Sen D. (2002) Ai general strategy for effector-mediated control of RNA-cleaving ribozymes and DNA enzymes. *J Mol Biol* 318: 33-43.

Wecker M, Smith D, Gold L. (1996) In vitro selection of a novel catalytic RNA: characterization of a sulfur alkylation reaction and interaction with a small peptide. *RNA* 2: 982-994.

Whitesides, (1995) Proceedings of the Robert A. Welch Foundation 39th Conference On Chemical Research Nanophase Chemistry., Houston, Tex.

Wiegand T W, Janssen R C, Eaton B E. (1997) Selection of RNA amide synthases. *Chem Biol* 4: 675-683.

Wilson C, Szostak J W. (1995) In vitro evolution of a self-alkylating ribozyme. *Nature* 374: 777-782.

Wilson D S, Szostak J W. (1999) In vitro selection of functional nucleic acids. *Annu Rev Biochem* 68: 611-647.

Zhang B, Cech T R. (1997) Peptide bond formation by in vitro selected ribozymes. *Nature* 390: 96-100.

Zillmann M, Limauro S E, Goodchild J. (1997) In vitro optimization of truncated stem-loop II variants of the hammerhead ribozyme for cleavage in low concentrations of magnesium under non-turnover conditions. *RNA* 3: 734-747.

REFERENCES FOR TABLE 3B

1. Ellington, A. D. & Conrad, R. (1995). Aptamers as potential nucleic acid pharmaceuticals. *Biotechnol. Annu. Rev.* 1: 185-214.
2. Jayasena, S. D. (1999). Aptamers: an emerging class of molecules that rival antibodies in diagnostics. *Clin. Chem.* (Washington, D.C.) 45: 1628-50.
3. Sun, L. Q., Cairns, M. J., Saravolac, E. G., Baker, A. & Gerlach, W. L. (2000). Catalytic nucleic acids: From lab to applications. *Pharmacol. Rev.* 52: 325-47.
4. Hesselberth, J., Robertson, M. P., Jhaveri, S. & Ellington, A. D. (2000). In vitro selection of nucleic acids for diagnostic applications. *Rev. Mol. Biotechnol.* 74: 15-25.
5. Joyce, G. F. (1999). Reactions Catalyzed by RNA and DNA Enzymes. In *The RNA World*, vol. 37 (Gesteland, R. F., Cech, T. R. & Atkins, J. F., ed.), pp. 687-9, Cold Spring Harbor Laboratory Press, Cold Spring Harbor, N.Y.
6. Breaker, R. R. (1997). DNA enzymes. *Nat. Biotechnol.* 15: 427-31.
7. Sen, D. & Geyer, C. R. (1998). DNA enzymes. *Curr. Opin. Chem. Biol.* 2: 680-7.
8. Breaker, R. R. (1999). Catalytic DNA: in training and seeking employment. *Nat. Biotechnol.* 17: 422-3.
9. Breaker, R. R. (2000). Making catalytic DNAs. *Science* (Washington, D.C.) 290: 2095-6.
10. Derose, V. J. (2002). Two Decades of RNA Catalysis. *Chemistry & Biology* 9: 961-9.
11. Ellington, A. D. & Szostak, J. W. (1990). In vitro selection of RNA molecules that bind specific ligands. *Nature* (London) 346: 818-22.
12. Ellington, A. D. & Szostak, J. W. (1992). Selection in vitro of single-stranded DNA molecules that fold into specific ligand-binding structures. *Nature* (London) 355: 850-2.
13. Santoro, S. W. & Joyce, G. F. (1997). A general purpose RNA-cleaving DNA enzyme. *Proc. Natl. Acad. Sci. U.S.A.* 94: 4262-6.
14. Faulhammer, D. & Famulok, M. (1996). The Ca2+ ion as a cofactor for a novel RNA-cleaving deoxyribozyme. *Angew. Chem., Int. Ed. Engl.* 35: 2837-41.
15. Li, J., Zheng, W., Kwon, A. H. & Lu, Y. (2000). In vitro selection and characterization of a highly efficient Zn(II)-dependent RNA-cleaving deoxyribozyme. *Nucleic Acids Res.* 28: 481-8.
16. Jenison, R. D., Gill, S. C., Pardi, A. & Polisky, B. (1994). High-resolution molecular discrimination by RNA. *Science* (Washington, D.C., United States) 263: 1425-9.
17. Santoro, S. W. & Joyce, G. F. (1998). Mechanism and utility of an RNA-cleaving DNA enzyme. *Biochemistry* 37: 13330-42.
18. Mannironi, C., Di Nardo, A., Fruscoloni, P. & Tocchini-Valentini, G. P. (1997). In vitro selection of dopamine RNA ligands. *Biochemistry* 36: 9726-34.
19. Sigurdsson, S. T., Thomson, J. B. & Eckstein, F. (1998). Small ribozymes. *Cold Spring Harbor Monogr. Ser.* 35: 339-76.
20. Stage-Zimmermann, T. K. & Uhlenbeck, O. C. (1998). Hammerhead ribozyme kinetics. *RNA* 4: 875-89.
21. Werstuck, G. & Green, M. R. (1998). Controlling gene expression in living cells through small molecule-RNA interactions. *Science* (Washington, D.C.) 282: 296-8.
22. Walter, N. G. & Burke, J. M. (1998). The hairpin ribozyme: structure, assembly and catalysis. *Curr. Opin. Chem. Biol.* 2: 24-30.
23. Holeman, L. A., Robinson, S. L., Szostak, J. W. & Wilson, C. (1998). Isolation and characterization of fluorophore-binding RNA aptamers. *Folding Des.* 3: 423-31.
24. Wilson, C. & Szostak, J. W. (1998). Isolation of a fluorophore-specific DNA aptamer with weak redox activity. *Chem. Biol.* 5: 609-17.
25. Pan, T. & Uhlenbeck, O. C. (1992). A small metalloribozyme with a two-step mechanism. *Nature* 358: 560-3.
26. Yang, Q., Goldstein, I. J., Mei, H.-Y. & Engelke, D. R. (1998). DNA ligands that bind tightly and selectively to cellobiose. *Proc. Natl. Acad. Sci. U.S.A.* 95: 5462-7.
27. Been, M. D. & Wickham, G. S. (1997). Self-cleaving ribozymes of hepatitis delta virus RNA. *Eur. J. Biochem.* 247: 741-53.
28. Tanner, N. K. (1998). Biochemistry of hepatitis delta virus catalytic RNAs. *Ribozymes Gene Ther. Cancer* 23-38.
29. Famulok, M. & Szostak, J. W. (1992). Stereospecific recognition of tryptophan agarose by in vitro selected RNA. *J. Am. Chem. Soc.* 114: 3990-1.
30. Cech, T. R. (1993). Structure and mechanism of the large catalytic RNAs: group I and group II introns and ribonuclease P. In *The RNA World* (Gesteland, R. F. & Atkins, J. F., ed.), pp. 239-70, Cold Spring Harbor Laboratory Press, Cold Spring Harbor, N.Y.
31. Cech, T. R. & Herschlag, D. (1996). Group I ribozymes: substrate recognition, catalytic strategies, and comparative mechanistic analysis. *Nucleic Acids Mol. Biol.* 10:1-17.
32. Famulok, M. (1994). Molecular Recognition of Amino Acids by RNA-Aptamers: An L-Citrulline Binding RNA Motif and Its Evolution into an L-Arginine Binder. *J. Am. Chem. Soc.* 116: 1698-706.

33. Geiger, A., Burgstaller, P., Von Der Eltz, H., Roeder, A. & Famulok, M. (1996). RNA aptamers that bind L-arginine with sub-micromolar dissociation constants and high enantioselectivity. *Nucleic Acids Res.* 24: 1029-36.
34. Tao, J. & Frankel, A. D. (1996). Arginine-Binding RNAs Resembling TAR Identified by in Vitro Selection. *Biochemistry* 35: 2229-38.
35. Connell, G. J., Illangesekare, M. & Yarus, M. (1993). Three small ribooligonucleotides with specific arginine sites. *Biochemistry* 32: 5497-502.
36. Burgstaller, P., Kochoyan, M. & Famulok, M. (1995). Structural probing and damage selection of citrulline- and arginine-specific RNA aptamers identify base positions required for binding. *Nucleic Acids Res.* 23: 4769-76.
37. Nolte, A., Klussmann, S., Bald, R., Erdmann, V. A. & Fuerste, J. P. (1996). Mirror-design of L-oligonucleotide ligands binding to L-arginine. *Nature Biotechnology* 14: 1116-9.
38. Valadkhan, S. & Manley, J. L. (2001). Splicing-related catalysis by protein-free snRNAs. *Nature* (London, United Kingdom) 413: 701-7.
39. Nissen, P., Hansen, J., Ban, N., Moore, P. B. & Steitz, T. A. (2000). The structural basis of ribosome activity in peptide bond synthesis. *Science* (Washington, D.C.) 289: 920-30.
40. Harada, K. & Frankel, A. D. (1995). Identification of two novel arginine binding DNAs. *EMBO J.* 14: 5798-811.
41. Carmi, N., Balkhi, H. R. & Breaker, R. R. (1998). Cleaving DNA with DNA. *Proc. Natl. Acad. Sci. U.S.A.* 95: 2233-7.
42. Majerfeld, I. & Yarus, M. (1994). An RNA pocket for an aliphatic hydrophobe. *Nat. Struct. Biol.* 1: 287-92.
43. Cuenoud, B. & Szostak, J. W. (1995). A DNA metalloenzyme with DNA ligase activity. *Nature* 375: 611-4.
44. Majerfeld, I. & Yarus, M. (1998). Isoleucine: RNA sites with associated coding sequences. *Rna* 4: 471-8.
45. Li, Y. & Breaker, R. R. (1999). Phosphorylating DNA with DNA. *Proc. Natl. Acad. Sci. U.S.A.* 96: 2746-51.
46. Sassanfar, M. & Szostak, J. W. (1993). An RNA motif that binds ATP. *Nature* (London) 364: 550-3.
47. Burgstaller, P. & Famulok, M. (1994). Isolation of RNA aptamers for biological cofactors by in vitro selection. *Angew. Chem.* 1.06: 1163-6 (See also Angew. Chem., Int. Ed. Engl., 994, 33(10), 084-7).
48. Burke, D. H. & Gold, L. (1997). RNA aptamers to the adenosine moiety of S-adenosyl methionine: structural inferences from variations on a theme and the reproducibility of SELEX. *Nucleic Acids Res.* 25: 2020-4.
49. Huizenga, D. E. & Szostak, J. W. (1995). A DNA Aptamer That Binds Adenosine and ATP. *Biochemistry* 34: 656-65.
50. Klussmann, S., Nolte, A., Bald, R., Erdmann, V. A. & Fuerste, J. P. (1996). Mirror-image RNA that binds D-adenosine. *Nat. Biotechnol.* 14: 1112-5.
51. Burmeister, J., Von Kiedrowski, G. & Ellington, A. D. (1997). Cofactor-assisted self-cleavage in DNA libraries with a 3'-'5'-phosphoramidate bond. *Angew. Chem., Int. Ed. Engl.* 36: 1321-4.
52. Connell, G. J. & Yarus, M. (1994). RNAs with dual specificity and dual RNAs with similar specificity. *Science* (Washington, D.C.) 264: 1137-41.
53. Li, Y. & Sen, D. (1996). A catalytic DNA for porphyrin metallation. *Nat. Struct. Biol.* 3: 743-7.
54. Lauhon, C. T. & Szostak, J. W. (1995). RNA aptamers that bind flavin and nicotinamide redox cofactors. *J. Am. Chem. Soc.* 117: 1246-57.
55. Travascio, P., Bennet, A. J., Wang, D. Y. & Sen, D. (1999). A ribozyme and a catalytic DNA with peroxidase activity: active sites versus cofactor-binding sites. *Chemistry & Biology* 6: 779-87.
56. Lorsch, J. R. & Szostak, J. W. (1994). In vitro selection of RNA aptamers specific for cyanocobalamin. *Biochemistry* 33: 973-82.
57. Rink, S. M., Shen, J.-C. & Loeb, L. A. (1998). Creation of RNA molecules that recognize the oxidative lesion 7,8-dihydro-8-hydroxy-2'-deoxyguanosine (8-oxodG) in DNA. *Proc. Natl. Acad. Sci. U.S.A.* 95: 11619-24.
58. Hailer, A. A. & Sarnow, P. (1997). In vitro selection of a 7-methyl-guanosine binding RNA that inhibits translation of capped mRNA molecules. *Proc. Natl. Acad. Sci. U.S.A.* 94: 8521-6.
59. Kiga, D., Futamura, Y., Sakamoto, K. & Yokoyama, S. (1998). An RNA aptamer to the xanthine/guanine base with a distinctive mode of purine recognition. *Nucleic Acids Res.* 26: 1755-60.
60. Lato, S. M., Boles, A. R. & Ellington, A. D. (1995). In vitro selection of RNA lectins: Using combinatorial chemistry to interpret ribozyme evolution. *Chem. Biol.* 2: 291-303.
61. Wang, Y., Killian, J., Hamasaki, K. & Rando, R. R. (1996). RNA Molecules That Specifically and Stoichiometrically Bind Aminoglycoside Antibiotics with High Affinities. *Biochemistry* 35: 1233846.
62. Wallis, M. G., Von Ahsen, U., Schroeder, R. & Famulok, M. (1995). A novel RNA motif for neomycin recognition. *Chem. Biol.* 2: 543-52.
63. Famulok, M. & Huettenhofer, A. (1996). In Vitro Selection Analysis of Neomycin Binding RNAs with a Mutagenized Pool of Variants of the 16S rRNA Decoding Region. *Biochemistry* 35: 4265-70.
64. Wallis, M. G., Streicher, B., Wank, H., Von Ahsen, U., Clodi, E., Wallace, S. T., Famulok, M. & Schroeder, R. (1997). In vitro selection of a viomycin-binding RNA pseudoknot. *Chem. Biol.* 4: 357-66.
65. Burke, D. H., Hoffman, D. C., Brown, A., Hansen, M., Pardi, A. & Gold, L. (1997). RNA aptamers to the peptidyl transferase inhibitor chloramphenicol. *Chem. Biol.* 4: 833-43.
66. Wallace, S. T. & Schroeder, R. (1998). In vitro selection and characterization of streptomycin-binding RNAs: recognition discrimination between antibiotics. *Rna* 4: 112-23.
67. Giver, L., Bartel, D. P., Zapp, M. L., Green, M. R. & Ellington, A. D. (1993). Selection and design of high-affinity RNA ligands for HIV-1 Rev. *Gene* 137: 19-24.
68. Giver, L., Bartel, D., Zapp, M., Pawul, A., Green, M. & Ellington, A. D. (1993). Selective optimization of the Rev-binding element of HIV-1. *Nucleic Acids Res.* 21: 5509-16.
69. Williams, K. P., Liu, X.-H., Schumacher, T. N. M., Lin, H. Y., Ausiello, D. A., Kim, P. S. & Bartel, D. P. (1997). Bioactive and nuclease-resistant L-DNA ligand of vasopressin. *Proc. Natl. Acad. Sci. U.S.A.* 94: 11285-90.
70. Zimmerman, J. M. & Maher, L. J., Iii (2002). In vivo selection of spectinomycin-binding RNAs. *Nucleic Acids Res.* 30: 5425-35.
71. Vianini, E., Palumbo, M. & Gatto, B. (2001). In vitro selection of DNA aptamers that bind L-tyrosinamide. *Bioorganic & Medicinal Chemistry* 9: 2543-8.
72. Andreola, M.-L., Pileur, F., Calmels, C., Ventura, M., Tarrago-Litvak, L., Toulme, J.-J. & Litvak, S. (2001). DNA aptamers selected against the HIV-1 RNase H display in vitro antiviral activity. *Biochemistry* 40: 10087-94.

73. Fukusaki, E.-I., Kato, T., Maeda, H., Kawazoe, N., Ito, Y., Okazawa, A., Kajiyama, S.-I. & Kobayashi, A. (2000). DNA aptamers that bind to chitin. *Bioorg. Med. Chem. Lett.* 10: 423-5.
74. Bock, L. C., Griffin, L. C., Lathamoi, J. A., Vermaas, E. H. & Toole, J. J. (1992). Selection of single-stranded DNA molecules that bind and inhibit human thrombin. *Nature* (London) 355: 564-6.
75. Koizumi, M. & Breaker, R. R. (2000). Molecular Recognition of cAMP by an RNA Aptamer. *Biochemistry* 39: 8983-92.
76. Kato, T., Takemura, T., Yano, K., Ikebukuro, K. & Karube, I. (2000). In vitro selection of DNA aptamers which bind to cholic acid. *Biochim. Biophys. Acta* 1493: 12-8.
77. Okazawa, A., Maeda, H., Fukusaki, E., Katakura, Y. & Kobayashi, A. (2000). In vitro selection of hematoporphyrin binding DNA aptamers. *Bioorg. Med. Chem. Lett.* 10: 2653-6.
78. Kawakami, J., Imanaka, H., Yokota, Y. & Sugimoto, N. (2000). In vitro selection of aptamers that act with Zn2+. *J. Inorg. Biochem.* 82: 197-206.
79. Bruno, J. G. & Kiel, J. L. (1999). In vitro selection of DNA aptamers to anthrax spores with electrochemiluminescence detection. *Biosensors & Bioelectronics* 14: 457-64.

The invention claimed is:

1. A sensor system for detecting an effector or cofactor, comprising an aggregate, wherein the aggregate comprises a plurality of complexes, and each complex comprises:
   (a) a nucleic acid enzyme, comprising a cofactor binding site and optionally an effector binding site;
   (b) a substrate for the nucleic acid enzyme, comprising a first polynucleotide;
   (c) a first particle comprising a second polynucleotide, wherein the polynucleotide is attached to the particle at the 3' terminus; and
   (d) a second particle comprising a third polynucleotide, wherein the polynucleotide is attached to the particle at the 5' terminus;
   wherein the substrate hybridizes to the second polynucleotide and the third polynucleotide, so that the first particle and the second particle are in a tail-to-tail arrangement,
   the nucleic acid enzyme is hybridized to the substrate between the second polynucleotide and the third polynucleotide, and
   the nucleic acid enzyme cleaves the substrate in the presence of the cofactor and optionally the effector.

2. The sensor system of claim 1, wherein the nucleic acid enzyme comprises DNA.

3. The sensor system of claim 2, wherein the first particle and the second particle comprise gold.

4. The sensor of claim 2, wherein the first particle and the second particle comprise a material selected from the group consisting of metals, semiconductors and latex.

5. The sensor of claim 2, wherein the effector or cofactor is selected from the group consisting of nitrogen fertilizers, pesticides, dioxin, phenols, 2,4-dichlorophenoxyacetic acid, Pb(II), Hg(II), As(III), $UO_2$(II), Fe(III), Zn(II), Cu(II), Co(II), glucose, insulin, hCG-hormone, HIV, HIV proteins, anthrax, small pox, nerve gases, TNT, DNT, cocaine and antibiotics.

6. The sensor system of claim 2, wherein the second particle has an average diameter of at least 30 nm.

7. The sensor system of claim 2, wherein the second particle has an average diameter of at least 35 nm.

8. The sensor system of claim 2, further comprising a buffer.

9. The sensor system of claim 8, wherein the buffer is selected to have a pH of 6.2 to 10.2.

10. The sensor system of claim 9, wherein the buffer is selected to have a pH of 7.2 to 9.2.

11. The sensor system of claim 2, wherein components of the sensor system are in an aqueous solution having an ionic strength of at least 0.20.

12. The sensor system of claim 2, wherein the nucleic acid enzyme is present at a concentration of at least 0.2 µM.

13. The sensor system of claim 2, wherein the first polynucleotide is present at a concentration of at least 1.5 nM.

14. A sensor system for detecting an effector or cofactor, comprising an aggregate, wherein the aggregate comprises a plurality of complexes, and each complex comprises:
   (a) a nucleic acid enzyme, comprising a cofactor binding site and optionally an effector binding site;
   (b) a substrate for the nucleic acid enzyme, comprising a first polynucleotide;
   (c) a first particle comprising a second polynucleotide, wherein the polynucleotide is attached to the particle at the 3' terminus; and
   (d) a second particle comprising a third polynucleotide, wherein the polynucleotide is attached to the particle at the 5' terminus;

wherein the substrate hybridizes to the second polynucleotide and the third polynucleotide, so that the first particle and the second particle are in a tail-to-tail arrangement, the nucleic acid enzyme is hybridized to the substrate between the second polynucleotide and the third polynucleotide, the nucleic acid enzyme cleaves the substrates in the presence of the cofactor and optionally the effector, and the second particle has an average diameter of at least 30 nm.

15. The sensor system of claim 14, wherein the second particle has an average diameter of at least 35 nm.

16. The sensor system of claim 14, wherein the nucleic acid enzyme comprises DNA.

17. The sensor system of claim 14, wherein the first particle and the second particle comprise gold.

18. The sensor of claim 14, wherein the first particle and second particle comprise a material selected from the group consisting of metals, semiconductors and latex.

19. The sensor of claim 14, wherein the effector or cofactor is selected from the group consisting of nitrogen fertilizers, pesticides, dioxin, phenols, 2,4-dichlorophenoxyacetic acid, Pb(II), Hg(II), As(III), $UO_2$(II), Fe(III), Zn(II), Cu(II), Co(II), glucose, insulin, hCG-hormone, HIV, HIV proteins, anthrax, small pox, nerve gases, TNT, DNT, cocaine and antibiotics.

20. The sensor system of claim 14, further comprising a buffer.

21. The sensor system of claim 20, wherein the buffer is selected to have a pH of 6.2 to 10.2.

22. The sensor system of claim 21, wherein the buffer is selected to have a pH of 7.2 to 9.2.

23. The sensor system of claim 14, wherein components of the sensor system are in an aqueous solution having an ionic strength of at least 0.20.

24. The sensor system of claim 14, wherein the nucleic acid enzyme is present at a concentration of at least 0.2 μM.

25. The sensor system of claim 14, wherein the first polynucleotide is present at a concentration of at least 1.5 nM.

26. The sensor of claim 2, wherein the effector or cofactor is a heavy metal ion.

27. The sensor of claim 14, wherein the effector or cofactor is a heavy metal ion.

* * * * *